United States Patent
Uemura et al.

(10) Patent No.: US 10,578,853 B2
(45) Date of Patent: Mar. 3, 2020

(54) IMAGE FORMING OPTICAL SYSTEM, IMAGE PICKUP APPARATUS, OPTICAL APPARATUS, AND CAPSULE ENDOSCOPE

(71) Applicant: OLYMPUS CORPORATION, Hachioji-shi, Tokyo (JP)

(72) Inventors: Ryosuke Uemura, Kunitachi (JP); Takahiro Amanai, Hachioji (JP); Kyoko Iijima, Hino (JP)

(73) Assignee: OLYMPUS CORPORATION, Tokyo (JP)

(*) Notice: Subject to any disclaimer, the term of this patent is extended or adjusted under 35 U.S.C. 154(b) by 402 days.

(21) Appl. No.: 15/256,464

(22) Filed: Sep. 2, 2016

(65) Prior Publication Data

US 2017/0068087 A1 Mar. 9, 2017

(30) Foreign Application Priority Data

Sep. 4, 2015 (JP) ................................ 2015-174659
Sep. 4, 2015 (JP) ................................ 2015-174660
Sep. 16, 2015 (JP) ................................ 2015-182835

(51) Int. Cl.
*G02B 13/18* (2006.01)
*G02B 23/24* (2006.01)
(Continued)

(52) U.S. Cl.
CPC ........ *G02B 23/243* (2013.01); *A61B 1/00163* (2013.01); *A61B 1/041* (2013.01);
(Continued)

(58) Field of Classification Search
CPC ............ G02B 13/0045; G02B 27/0025; G02B 13/18; G02B 5/005; G02B 3/04;
(Continued)

(56) References Cited

U.S. PATENT DOCUMENTS 4,932,764 A 6/1990 Simpson
5,473,473 A * 12/1995 Estelle ................. G02B 15/161
359/691

(Continued)

FOREIGN PATENT DOCUMENTS

JP H05164965 A 6/1993
JP H08334684 A 12/1996
(Continued)

OTHER PUBLICATIONS

Japanese Office Action (and English language translation thereof) dated Mar. 6, 2019 issued in counterpart Japanese Application No. 2015-174659.

(Continued)

*Primary Examiner* — Robert E. Tallman
(74) *Attorney, Agent, or Firm* — Holtz, Holtz & Volek PC

(57) ABSTRACT

An image pickup apparatus includes an image forming optical system having lens components and an image pickup unit, and the lens component is a lens having an object-side surface and an image-side surface that are in contact with air in an effective optical path, and the image forming optical system includes in order from an object side to an image side, an object-side lens component and an image-side lens component, and the image pickup unit has an image pickup surface curved to be concave toward the object side, and a surface nearest to the object of the object-side lens component has a concave shape portion which is concave shape toward the object side in a meridional direction, in at least an off-axis effective surface, and a surface nearest to the image of the image-side lens component is a curved surface.

65 Claims, 25 Drawing Sheets

(51) Int. Cl.
  *G02B 13/00* (2006.01)
  *A61B 1/04* (2006.01)
  *A61B 1/00* (2006.01)
  *G02B 27/00* (2006.01)
  *G02B 5/00* (2006.01)
  *G02B 15/177* (2006.01)
  *G02B 9/04* (2006.01)
  *G02B 3/04* (2006.01)

(52) U.S. Cl.
  CPC .............. *G02B 13/003* (2013.01); *G02B 3/04* (2013.01); *G02B 5/005* (2013.01); *G02B 9/04* (2013.01); *G02B 13/002* (2013.01); *G02B 13/0045* (2013.01); *G02B 13/18* (2013.01); *G02B 15/177* (2013.01); *G02B 27/0025* (2013.01)

(58) Field of Classification Search
  CPC .... G02B 13/04; G02B 13/002; G02B 15/177; G02B 9/04; G02B 13/003; G02B 23/243
  USPC ................. 359/717, 713–716, 740, 793–795
  See application file for complete search history.

(56) References Cited

U.S. PATENT DOCUMENTS

| | | | |
|---|---|---|---|
| 5,502,597 A * | 3/1996 | Estelle | ............... G02B 13/06 359/717 |
| 5,552,936 A | 9/1996 | Ohno | |
| 5,689,376 A | 11/1997 | Lewis | |
| 5,739,965 A | 4/1998 | Ohno | |
| 6,072,636 A | 6/2000 | Sato | |
| 6,335,835 B1 | 1/2002 | Koike | |
| 6,873,473 B2 | 3/2005 | Lewis et al. | |
| 7,796,342 B2 | 9/2010 | Baba | |
| 8,953,071 B2 | 2/2015 | Yamano | |
| 2004/0036981 A1 | 2/2004 | Lewis et al. | |
| 2009/0141364 A1* | 6/2009 | Baba | ................ A61B 1/00096 359/648 |
| 2013/0063634 A1 | 3/2013 | Yamano | |
| 2013/0278714 A1 | 10/2013 | Hirose | |
| 2014/0015997 A1 | 1/2014 | Baba | |
| 2015/0077619 A1 | 3/2015 | Yamano | |

FOREIGN PATENT DOCUMENTS

| | | |
|---|---|---|
| JP | H08338944 A | 12/1996 |
| JP | 2000081568 A | 3/2000 |
| JP | 2000227547 A | 8/2000 |
| JP | 2000266997 A | 9/2000 |
| JP | 2004086215 A | 3/2004 |
| JP | 2009136385 A | 6/2009 |
| JP | 2012237966 A | 12/2012 |
| JP | 2013024892 A | 2/2013 |
| JP | 2013025202 A | 2/2013 |
| JP | 2013061476 A | 4/2013 |
| WO | 2012090729 A1 | 7/2012 |
| WO | 2014073685 A1 | 5/2014 |

OTHER PUBLICATIONS

Japanese Office Action (and English language translation thereof) dated Feb. 27, 2019 issued in Japanese Application No. 2015-182835.

Japanese Office Action (and English language translation thereof) dated Feb. 13, 2019 issued in counterpart Japanese Application No. 2015-174660.

* cited by examiner

SA       AS       DT       CC
FNO 3.405  ω 81.00  ω 81.00  ω 81.00

SA          AS        DT        CC
FNO 3.341   ω 81.00   ω 81.00   ω 81.00

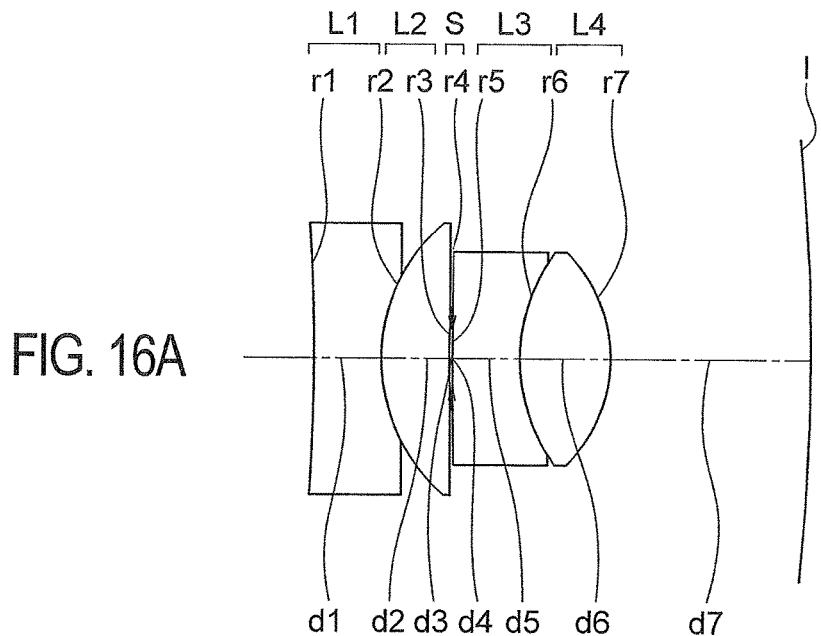
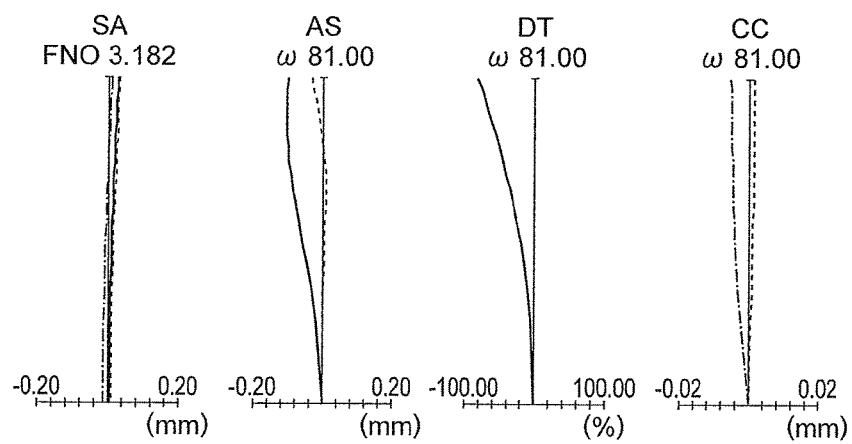

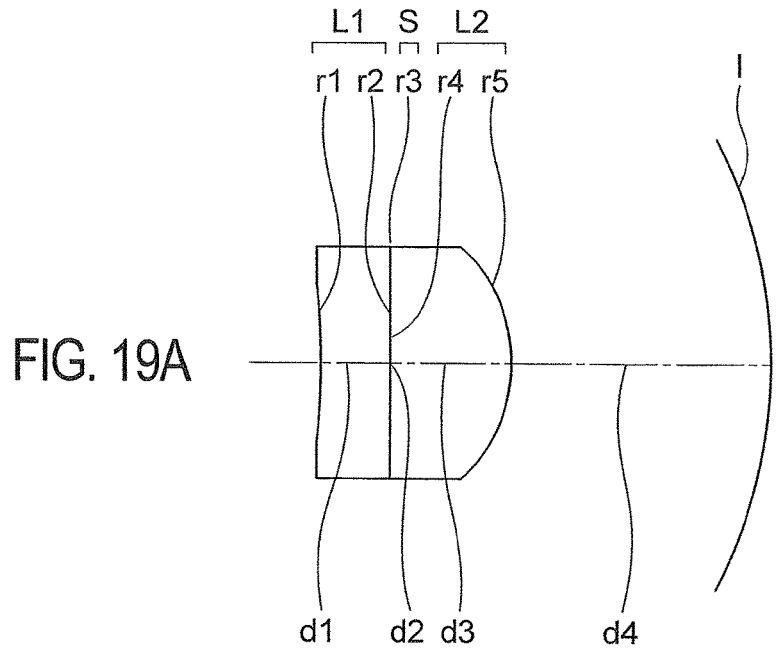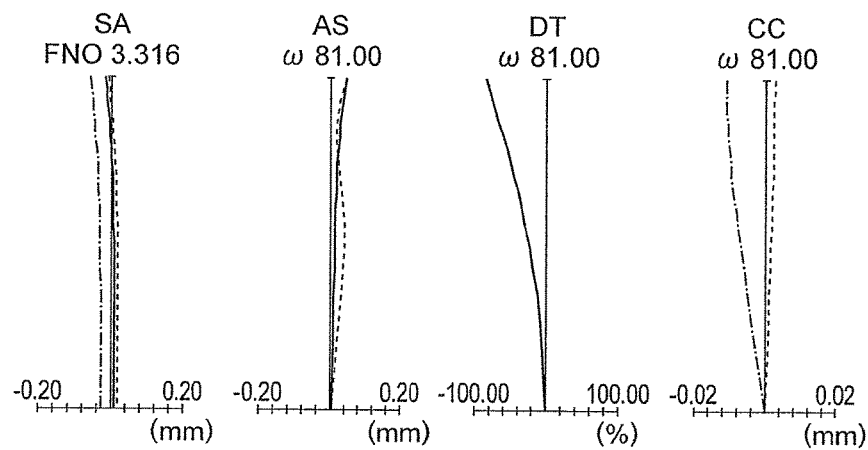

IMAGE FORMING OPTICAL SYSTEM, IMAGE PICKUP APPARATUS, OPTICAL APPARATUS, AND CAPSULE ENDOSCOPE

CROSS-REFERENCE TO RELATED APPLICATION

The present application is based upon and claims the benefit of priority from the prior Japanese Patent Application Nos. 2015-174659 filed on Sep. 4, 2015, 2015-174660 filed on Sep. 4, 2015 and 2015-182835 filed on Sep. 16, 2015; the entire contents of which are incorporated herein by reference.

BACKGROUND OF THE INVENTION

Field of the Invention

The present invention relates to an image forming optical system, an image pickup apparatus, an optical apparatus, and a capsule endoscope.

Description of the Related Art

As an optical system having a wide angle of view that forms a curved image, a wide-angle lens described in International Unexamined Patent Application Publication No. 2012/090729 is available. The wide-angle lens described in International Unexamined Patent Application Publication No. 2012/090729 includes in order from an object side, a first lens, a second lens, and a third lens. The first lens is a meniscus lens having a convex surface directed toward the object side, the second lens has a positive refractive power, and the third lens has a concave surface directed toward an image side.

SUMMARY OF THE INVENTION

An image pickup apparatus according to an aspect of the present invention comprises;
an image forming optical system having lens components, and
an image pickup unit, wherein
the lens component is a lens having an object-side surface and an image-side surface that are in contact with air in an effective optical path, and
the effective optical path is an optical path through which a light beam that contributes to image formation passes, and
the image forming optical system includes in order from an object side to an image side, an object-side lens component and an image-side lens component, and
the image pickup unit has an image pickup surface curved to be concave toward the object side, which is disposed on the image side of the image forming optical system, and
a surface nearest to an object of the object-side lens component is a surface having a concave shape portion which is concave shape toward the object side in a meridional direction, in at least an off-axis effective surface, and
a surface nearest to an image of the image-side lens component is a curved surface.

An image pickup apparatus according to another aspect of the present invention comprises;
an image forming optical system having lens components, and
an image pickup unit, wherein
the lens component is a lens having an object-side surface and an image-side surface that are in contact with air in an effective optical path, and
the effective optical path is an optical path through which a light beam that contributes to image formation passes, and
the image forming optical system includes in order from an object side to an image side, an object-side lens component and an image-side lens component, and
the image pickup unit has an image pickup surface curved to be concave toward the object side, which is disposed on the image side of the image forming optical system, and
a surface nearest to an object of the object-side lens component is one of a flat surface and a surface having a concave shape toward the object side, and
a surface nearest to an image of the image-side lens component is a curved surface, and
the following conditional expression (A1) is satisfied:

$$0 < L/TL \leq 0.4 \quad (A1),$$

where,
L denotes a distance on an optical axis from a surface nearest to the image of the object-side lens component up to a surface nearest to the object of the image-side lens component, and
TL denotes a distance on the optical axis from the surface nearest to the object of the object-side lens component up to the image pickup surface.

Moreover, an image forming optical system according to still another aspect of the present invention comprises;
a plurality of lens components, wherein
the lens component is a lens having an object-side surface and an image-side surface that are in contact with air in an effective optical path, and
the effective optical path is an optical path through which a light beam that contributes to image formation passes, and
the plurality of lens components include in order from an object side to an image side, an object-side lens component and an image-side lens component, and
an image is formed on an image pickup surface which is curved to be concave toward the object side, and
the following conditional expression (A5) is satisfied:

$$L_{1e}/R_{11} \leq 0 \quad (A5),$$

where,
$L_{1e}$ denotes a distance on an optical axis from a surface nearest to an object of the object-side lens component up to a surface nearest to the image of the image-side lens component, and
$R_{11}$ denotes a radius of curvature of the surface nearest to the object of the object-side lens component.

Moreover, an image forming optical system according to still another aspect of the present invention comprises
a plurality of lens components, wherein
the lens component is a lens having an object-side surface and an image-side surface that are in contact with air in an effective optical path, and
the effective optical path is an optical path through which a light beam that contributes to image formation passes, and
the plurality of lens components include in order from an object side to an image side, an object-side lens component and an image-side lens component, and
an image is formed on an image pickup surface which is curved to be concave toward the object side, and
the following conditional expression (A6) is satisfied:

$$PS_{inv}/R_{11} \leq 0 \quad (A6),$$

where,
$R_{11}$ denotes a radius of curvature of the surface nearest to an object of the object-side lens component, and
$PS_{inv}$ denotes an inverse number of Petzval's sum for the image forming optical system, and here Petzval's sum PS is expressed by the following expression:

$$PS = \sum_{i=1}^{k} \frac{1}{n_i \times f_i}$$

where, i denotes an order from the object side of lenses in the image forming optical system, k denotes total number of lenses in the image forming optical system, $n_i$ denotes a refractive index for a d-line of an $i^{th}$ lens, and $f_i$ denotes a focal length of the $i^{th}$ lens.

An image forming optical system according to still another aspect of the present invention comprises;

a plurality of lens components, and an aperture stop which limits an axial light beam, wherein the lens component is a lens having an object-side surface and an image-side surface that are in contact with air in an effective optical path, and the effective optical path is an optical path through which a light beam that contributes to image formation passes, and the plurality of lens components include in order from an object side to an image side, an object-side lens component and an image-side lens component, and an image is formed on an image pickup surface which is curved to be concave toward the object side, and the following conditional expression (5) is satisfied:

$$PS \times EXP < -0.7 \qquad (5),$$

where,

PS denotes Petzval's sum for the image forming optical system, and here

Petzval's sum PS is expressed by the following expression:

$$PS = \sum_{i=1}^{k} \frac{1}{n_i \times f_i}$$

where, i denotes an order of lenses from the object side in the image forming optical system, k denotes total number of lenses in the image forming optical system, $n_i$ denotes a refractive index for a d-line of the $i^{th}$ lens, $f_i$ denotes a focal length of the $i^{th}$ lens, and EXP denotes a distance along an optical axis from the image up to a paraxial exit pupil position of the image forming optical system, and is let to be negative when the paraxial exit pupil is on the object side of the image.

An image forming optical system according to still another aspect of the present invention comprises;

a plurality of lens components, and an aperture stop which limits an axial light beam, wherein the lens component is a lens having an object-side surface and an image-side surface that are in contact with air in an effective optical path, and the effective optical path is an optical path through which a light beam that contributes to image formation passes, and the plurality of lens components include in order from an object side to an image side, an object-side lens component and an image-side lens component, and an image is formed on an image pickup surface which is curved to be concave toward the object side, and the following conditional expression (6) is satisfied:

$$(EXP/f)/(\phi_e/\phi_1) < -1.3 \qquad (6),$$

where,

EXP denotes a distance along an optical axis from the image up to a paraxial exit pupil position of the image forming optical system, and is let to be negative when the paraxial exit pupil position is on the object side of the image, f denotes a focal length of the image forming optical system, $\phi_e$ denotes a maximum diameter of an area on the surface nearest to the object of the object-side lens component, through which an effective light beam that contributes to image formation at a maximum image height position passes, when measured perpendicularly with respect to the optical axis, and $\phi_1$ denotes a maximum diameter of an area on the surface nearest to object of the object-side lens component through which an axial light beam of the image forming optical system passes, when measured perpendicularly with respect to the optical axis.

An image forming optical system according to still another aspect of the present invention which forms an image curved to be concave toward an object side, comprises;

an object-side optical surface which is positioned nearest to an object, and an image-side optical surface which is positioned nearest to the image, wherein the following conditional expressions (B1), (B2), (B3), and (B4) are satisfied:

$$0 \leq |R_e/R_1| < 0.8 \qquad (B1),$$

$$R_e/TL' < 0 \qquad (B2),$$

$$EXP_{60}/f < 0 \qquad (B3), \text{ and}$$

$$0 < Y_1 \times 2/f < 2 \qquad (B4),$$

where, $R_1$ denotes a paraxial radius of curvature of the object-side optical surface, $R_e$ denotes a paraxial radius of curvature of the image-side optical surface, TL' denotes a distance on an optical axis from the object-side optical surface up to the image, $EXP_{60}$ denotes an exit-pupil position by a light ray incident on the image forming optical system at a half angle of view of 60 degrees, f denotes a focal length of the image forming optical system, and $Y_1$ denotes a maximum light ray height in a predetermined area, and here the predetermined area is an area of the object-side optical surface through which an effective light beam passes.

An optical apparatus according to the present invention comprises;

the abovementioned image forming optical system, and an image pickup unit having an image pickup surface which is curved to be concave toward the object side.

A capsule endoscope according to still another aspect of the present invention comprises the abovementioned image forming optical system, an image pickup unit having an image pickup surface curved to be concave toward the object side, which is disposed on an image side of the image forming optical system, and a cover portion having a dome shape, which is disposed on an object side of the image forming optical system.

BRIEF DESCRIPTION OF THE DRAWINGS

FIG. 16A is a cross-sectional view of an image forming optical system according to an example 12, and FIG. 16B, FIG. 16C, FIG. 16D, and FIG. 16E are aberration diagrams according to the example 12;

FIG. 19A is a cross-sectional view of an image forming optical system according to an example 15, and FIG. 19B, FIG. 19C, FIG. 19D, and FIG. 19E are aberration diagrams according to the example 15;

DETAILED DESCRIPTION OF THE INVENTION

Figure 1:
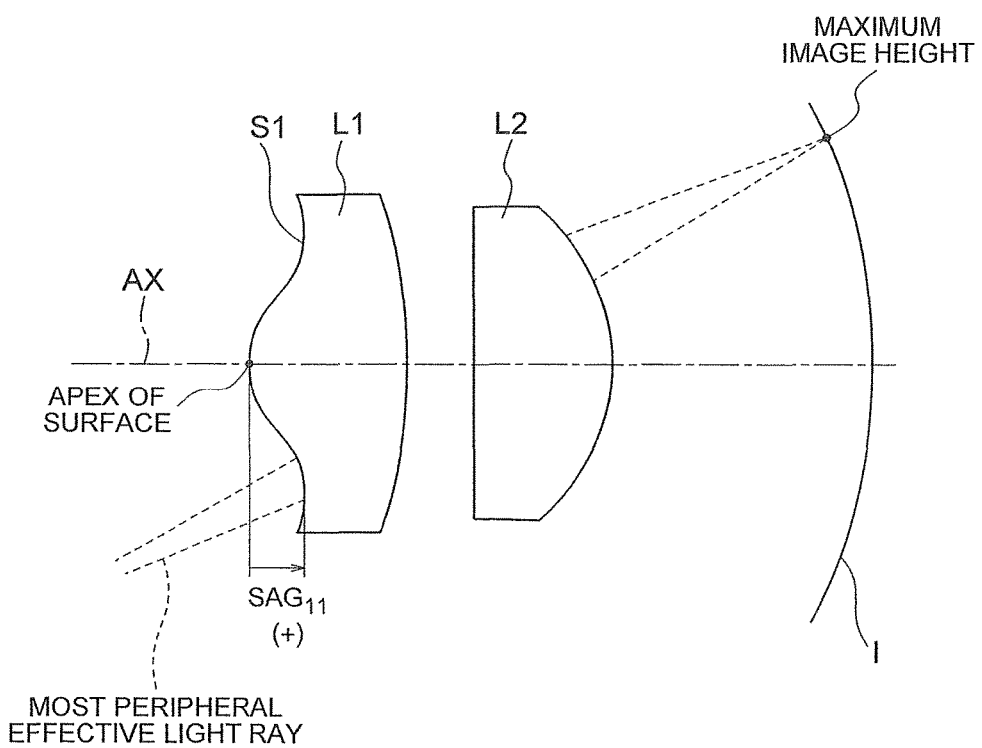
FIG. 1 is a diagram illustrating parameters used in conditional expressions.

Embodiments and examples of an image pickup apparatus will be described below in detail by referring to the accompanying diagrams. However, the present invention is not restricted to the embodiments and the examples described below.

An image pickup apparatus according to a first embodiment includes an image forming optical system having lens components, and an image pickup unit, wherein the lens component is a lens having only two surfaces that are in contact with air in an effective optical path namely, an object-side surface and an image-side surface, and the effective optical path is an optical path through which a light beam that contributes to image formation passes, and the image forming optical system includes in order from an object side to an image side, two lens components namely, an object-side lens component and an image-side lens component, and the image pickup unit has an image pickup surface curved to be concave toward the object side, which is disposed on the image side of the image forming optical system, and a surface nearest to an object of the object-side lens component is a surface having a concave shape portion which is concave shape toward the object side in a meridional direction, in at least an off-axis effective surface, and a surface nearest to an image of the image-side lens component is a curved surface.

In an optical system that forms an image which is curved to be concave toward the object side entirely or partially (hereinafter, referred to as 'a curved image'), correction of a curvature of field is acceptable. Consequently, in the optical system that forms a curved image, a load of aberration correction is reduced as compared to that in an optical system that forms a flat image.

For instance, in the optical system that forms the curved image, it is possible to reduce a lens that corrects Petzval's sum. Consequently, it is possible to reduce the number of lens components, and to make the optical system small-sized. In the lens component, only an object-side surface and an image-side surface are in contact with air in an optical path.

Moreover, in the optical system that forms the flat image, for correcting the curvature of field, it is necessary to dispose a lens for correction at a position away from an aperture stop. However, when the lens for correction is disposed, an outer diameter of the optical system becomes large, and the number of lens components further increase. In such manner, the lens for correction is one of the factors that make the outer diameter of the optical system large, and increase the number of lens components.

Whereas, in the optical system that forms the curved image, there is no need to dispose the lens for correction. Consequently, in the optical system that forms the curved image, it is possible to make the outer diameter small, and to further reduce the number of lenses.

Moreover, by receiving an image of an optical system on an image pickup element having a curved image pickup surface, correction of a distortion becomes easy. Moreover, there is no need to make the optical system to be a telecentric optical system for letting a light ray to be incident almost perpendicularly on the image pickup surface. Consequently, in the optical system that forms the curved image, a degree of freedom of designing to achieve both of a small-sizing and an optical performance is widened.

The image forming optical system in the present embodiment is also an optical system that forms the curved image. Therefore, it is possible to reduce the number of lens components, and to make the optical system small-sized. Furthermore, since the degree of freedom of designing widens, it is possible to realize an optical system having a superior imaging performance with lesser number of lens components.

The image pickup apparatus according to the present embodiment has the image forming optical system which includes in order from the object side to the image side, two lens components namely, the object-side lens component and the image-side lens component when the lens component is let to be a lens having only two surfaces that are in contact with air in an effective optical path namely, an object-side surface and an image-side surface.

Moreover, an aberration is reduced by letting the object-side surface and the image-side surface of the object-side lens component to be curved surfaces, and the object-side surface is let to be concave shape toward the meridional direction in at least the off-axis effective surface. This is advantageous for correcting aberration or securing wide angle of view.

In such manner, according to the present embodiment, in spite of two lens components, which is a small number, it is possible to achieve a favorable imaging performance along the image pickup surface curved to be concave toward the object side, while securing the angle of view and the amount of the curvature of field optimally.

Moreover, in the image pickup apparatus according to the present embodiment, it is preferable that the surface nearest to the image of the image-side lens component is a surface which is convex shape toward the image side.

By letting the surface nearest to the image of the image-side lens component disposed close to an image plane to be convex shape toward the image side, it is possible to reduce an astigmatism.

In the image pickup apparatus according to the present embodiment, it is preferable that the surface nearest to the object of the object-side lens component is an aspheric surface.

As described above, in the image pickup apparatus according to the present embodiment, the curved image is formed. The curved image is picked up by the image pickup element, for instance. When an amount of curvature of the curved image is large, an amount of curvature of the image pickup surface of the image pickup element also becomes large. Since there is a limit for the amount of curvature of the image pickup surface while manufacturing, it is preferable to let the amount of curvature of the curved image to be an appropriate amount.

Moreover, in the curved image, it is preferable that an aberration is corrected favorably.

Consequently, the image forming optical system is sought to have an appropriate amount of curvature of field that occurs, while having a wide angle of view, and also to form the curved image in which an aberration other than the curvature of field is corrected favorably. Therefore, by letting the object-side optical surface to be an aspheric surface, it is advantageous for forming a wide-angle curved image in which the amount of the curvature of field that occurs is appropriate, and in which an aberration other than the curvature of field has been corrected favorably.

In the image pickup apparatus according to the present embodiment, it is preferable that the aspheric surface which is nearest to the object of the object-side lens component is a surface having an inflection point on the off-axis effective surface in a cross-section including an optical axis.

Such arrangement is preferable as it enables to realize a wider angle of view while making appropriate the amount of curvature of field that occurs.

In the image pickup apparatus according to the present embodiment, it is preferable that the following conditional expression (1) is satisfied:

$$SAG_{11}/f<0 \qquad (1),$$

where, $SAG_{11}$ denotes a distance on the surface nearest to the object of the object-side lens component, in a direction along the optical axis, from an apex of the surface up to a point in which a most peripheral effective light ray incident at a maximum image height on the image forming optical system passes through the surface nearest to the object of the object-side lens component, letting a direction in which a light ray travels to be a positive direction, and f denotes a focal length of the image forming optical system.

FIG. 1 is a diagram illustrating a parameter $SAG_{11}$. The parameter $SAG_{11}$ is a distance on the surface S1 nearest to the object of the object-side lens component L1, in a direction along an optical axis AX, from an apex of a surface up to a point in which the most peripheral effective light ray incident at the maximum image height on the image forming optical system passes through the surface S1 nearest to an object of an object-side lens component L1. Here, direction in which a light ray travels is let to be a positive direction.

By satisfying the conditional expression (1), it is possible to achieve widening of the angle of view while maintaining the amount of curvature of field to be appropriate.

By making so as not to exceed an upper limit value of the conditional expression (1), it becomes easy to secure a negative refractive power entirely or partially on the surface nearest to the object of the object-side lens component, and it is advantageous for securing the wide angle of view.

It is preferable that the following conditional expression (1-1) is satisfied instead of the conditional expression (1).

$$-0.03 < SAG_{11}/f < 0 \quad (1\text{-}1)$$

By making so as not to fall below a lower limit value of the conditional expression (1-1), it is advantageous for reducing an off-axis aberration and an effect of an assembly error.

It is preferable to let the lower limit value of the conditional expression (1-1) to be −0.02, and more preferably to be −0.015. Moreover, it is preferable to let the upper limit value of the conditional expressions (1) and (1-1) to be −0.0005, and more preferably to be −0.001.

In the image pickup apparatus according to the present embodiment, it is preferable that the following conditional expression (2) is satisfied:

$$0 < |R_{2e}/R_{img}| \leq 2.0 \quad (2),$$

where, $R_{2e}$ denotes a radius of curvature of the surface nearest to the image of the image-side lens component, and $R_{img}$ denotes a minimum value of a radius of curvature of a virtual spherical surface which includes an apex and a point at which a light ray incident on the image forming optical system at a half angle of view of 60 degrees intersects the image pickup surface, letting a point of intersection of the optical axis and the image pickup surface to be the apex.

Figure 2:
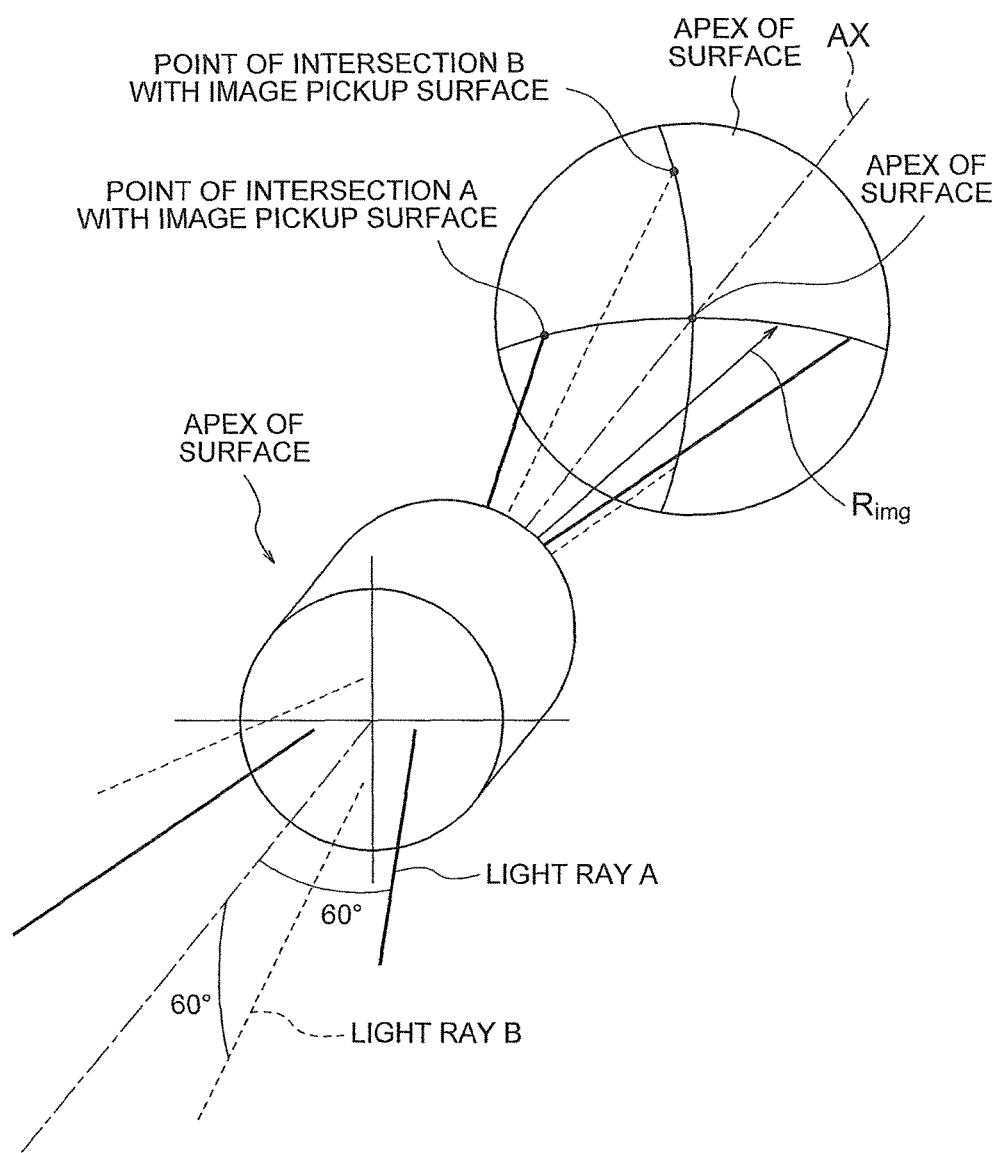
FIG. 2 is another diagram illustrating parameters used in conditional expressions.

FIG. 2 is a diagram illustrating a parameter $R_{img}$. When the image pickup surface has a curved shape that is rotationally symmetric about an axis, a value of the radius of curvature of the virtual spherical surface is same irrespective of a direction of the angle of view (for example, in a vertical direction shown in a light ray B and a horizontal direction shown in a light ray A on a paper surface). Moreover, when the image pickup surface has a shape such as a cylindrical shape, a toric shape, or a shape formed by joining a plurality of flat surfaces, since the value of the radius of curvature of the virtual spherical surface varies according to the direction of the angle of view, the radius of curvature of the virtual surface is let to be a value that is the minimum of a value that may be assumed in that case.

The conditional expression (2) regulates a relationship between the radius of curvature of the surface nearest to the image of the image-side lens component and the abovementioned $R_{img}$.

By satisfying the conditional expression (2), it is possible to maintain the astigmatism that occurs on the image pickup surface to be small, and to achieve a favorable imaging performance.

By making so as not to exceed an upper limit value of the conditional expression (2), it becomes easy to make the radius of curvature of the surface nearest to the image of the image-side lens component small with respect to the image pickup surface, and thereby it is preferable to correct the astigmatism.

When falling below a lower limit value of the conditional expression (2), since the image pickup surface becomes a flat surface, correction of the curvature of field with a small number of lens components becomes difficult.

For the conditional expression (2), it is preferable to let the lower limit value to be 0.1, and more preferably to be 0.2. For the conditional expression (2), it is preferable to let the upper limit value to be 1.5, and more preferably to be 1.0.

In the image pickup apparatus according to the present embodiment, it is preferable that the following conditional expression (3) is satisfied:

$$L_{1e}/TL \leq 0.65 \quad (3),$$

where, $L_{1e}$ denotes a distance on the optical axis from the surface nearest to the object of the object-side lens component up to the surface nearest to the image of the image-side lens component, and TL denotes a distance on the optical axis from the surface nearest to the object of the object-side lens component up to the image pickup surface.

By satisfying the conditional expression (3), a back focus can be secured adequately while maintaining the imaging performance.

When exceeding an upper limit value of the conditional expression (3), correction of an aberration becomes easy, but it becomes difficult to secure the back focus.

By making so as not to exceed the upper limit value of the conditional expression (3), it becomes easy to secure the back focus, and to realize small-sizing and weight-reduction of the image forming optical system with respect to a size of the image plane.

It is preferable that the following conditional expression (3-1) is satisfied instead of the conditional expression (3).

$$0.2 < L_{1e}/TL \leq 0.5 \quad (3\text{-}1)$$

Technical significance of the upper limit value of the conditional expression (3-1) is same as the technical significance of the conditional expression (3).

By making so as not fall below a lower limit value of the conditional expression (3-1), it becomes easy to secure adequate distance on the optical axis from the surface nearest to the object of the object-side lens component up to the surface nearest to the image of the image-side lens component, and it is advantageous for correction of aberration and for securing a favorable imaging performance.

For the conditional expression (3), it is preferable to let the upper limit value to be 0.61, and more preferably to be 0.5. For the conditional expressions (3) and (3-1), it is preferable to let the lower limit value to be 0.25, and more preferably to be 0.3.

It is preferable that the image pickup apparatus according to the present embodiment has the image forming optical system including lens components, and the lens component is a lens having only two surfaces that are in contact with air in the effective optical path namely, the object-side surface and the image-side surface, and the effective optical path is the optical path through which the light beam that contributes to the image formation passes, and the image forming optical system includes in order from the object side to the image side, two lens components namely, the object-side lens component and the image-side lens component, and the image is formed on the image pickup surface which is curved to be concave toward the object side, and the following conditional expression (4) is satisfied:

$$PS \times SAG_{11} < 0 \quad (4),$$

where, $SAG_{11}$ denotes the distance on the surface nearest to the object of the object-side lens component, in the direction along the optical axis, from the apex of the surface up to the point in which the most peripheral effective light ray incident at the maximum image height on the image forming optical system passes through the surface nearest to the object of the object-side lens component, letting the direction in which the light ray travels to be the positive direction, and PS denotes Petzval's sum for the image forming optical system, and here Petzval's sum PS is expressed by the following expression:

$$PS = \sum_{i=1}^{k} \frac{1}{n_i \times f_i}$$

where, i denotes an order of lenses from the object side in the image forming optical system, k denotes total number of lenses in the image forming optical system, $n_i$ denotes a refractive index for a d-line of an $i^{th}$ lens, and $f_i$ denotes a focal length of the $i^{th}$ lens.

By having a portion that is concave shape toward the object side in the off-axis effective surface of the surface nearest to the object of the object-side lens component, and by satisfying the conditional expression (4), it is possible to achieve a favorable imaging performance along the image pickup surface which is curved to be concave toward the object side, while securing the angle of view and maintaining the amount of the curvature of field to be optimum.

It is preferable that the following conditional expression (4-1) is satisfied instead of the conditional expression (4).

$$-0.02 < PS \times SAG_{11} < 0 \quad (4\text{-}1)$$

By making so as not to exceed an upper limit value of the conditional expressions (4) and (4-1), it becomes easy to secure a negative refractive power entirely or partially of an effective area of the surface nearest to the object of the object-side lens component, and it is advantageous for widening the angle of view.

It is preferable to suppress Petzval's sum and an excessive amount of curvature of field by making so as not to fall below a lower limit value of the conditional expression (4-1). Or, when falling below the lower limit value, since a sag of a surface nearest to the object of the object-side lens component becomes large, it is preferable to suppress the sag and make the formation of a lens easy by making so as not to fall below the lower limit value.

It is preferable to let the lower limit value of the conditional expression (4-1) to be −0.015, and more preferably to be −0.01. Moreover, it is preferable to let the upper limit value of the conditional expressions (4) and (4-1) to be −0.0003, and more preferably to be −0.001.

It is preferable that the image pickup apparatus according to the present embodiment includes an aperture stop which limits an axial light beam, and the following conditional expression (5) is satisfied:

$$PS \times EXP < -0.7 \quad (5),$$

where,

PS denotes Petzval's sum for the image forming optical system, and here

Petzval's sum PS is expressed by the following expression:

$$PS = \sum_{i=1}^{k} \frac{1}{n_i \times f_i}$$

where, i denotes the order of lenses from the object side in the image forming optical system, k denotes the total number of lenses in the image forming optical system, $n_i$ denotes the refractive index for the d-line of the $i^{th}$ lens, $f_i$ denotes the focal length of the $i^{th}$ lens, and EXP denotes a distance along the optical axis from the image up to a paraxial exit pupil position of the image forming optical system, and is let to be negative when the paraxial exit pupil is on the object side of the image.

By satisfying the conditional expression (5), it is advantageous for making appropriate the amount of curvature of field that occurs and an angle of incidence of a light ray on the curved image pickup surface.

It is preferable that the following conditional expression (5-1) is satisfied instead of the conditional expression (5).

$$-1.7 < PS \times EXP < -0.7 \quad (5\text{-}1)$$

By making so as not to exceed an upper limit value of the conditional expressions (5) and (5-1), it becomes easy to make Petzval's sum large, and it is advantageous for securing an amount of curvature of the image plane of the image forming optical system. Or more specifically, it is advantageous for achieving a favorable image by suppressing the exit-pupil position from coming too close to the image pickup surface, and by suppressing an angle of incidence of a light ray on the curved image pickup surface. For example, it becomes easy to suppress chromatic shading that occurs due to an effect of a light ray being incident obliquely on the image pickup element.

By making so as not to fall below a lower limit value of the conditional expression (5-1), it becomes easy to suppress Petzval's sum from becoming excessive. Accordingly, since it is possible to prevent an occurrence of a large curvature of field in the image forming optical system, it is advantageous for a reduction in cost of making the image pickup element having a shape close to that of the image plane of the image forming optical system. Or more specifically, it is advantageous for preventing the exit-pupil position from becoming far from the image pickup surface, and suppressing the angle of incidence of a light ray incident on the curved image pickup surface from becoming large.

For the conditional expression (5-1), it is preferable to let the lower limit value to be −1.5, and more preferably to be −1.4. Moreover, for the conditional expressions (5) and (5-1), it is preferable to let the upper limit value to be −0.8, and more preferably to be −0.87.

In the image pickup apparatus according to the present embodiment, it is preferable that the aperture stop is disposed between the object-side lens component and the image-side lens component.

In the present embodiment, by disposing the aperture stop between the object-side lens component and the image-side lens component for instance, it is further advantageous for small-sizing of each lens component. Moreover, it becomes easy to maintain an optical performance by such arrangement.

It is preferable that the image pickup apparatus according to the present embodiment includes the aperture stop which limits the axial light beam, and the following conditional expression (6) is satisfied:

$$(EXP/f)/(\phi_e/\phi_1) < -1.3 \quad (6),$$

where,

EXP denotes the distance along the optical axis from the image up to the paraxial exit pupil position of the image forming optical system, and is let to be negative when the paraxial exit pupil position is on the object side of the image, f denotes the focal length of the image forming optical system, $\phi_e$ denotes a maximum diameter of an area on the surface nearest to the object of the object-side lens component through which an effective light beam that contributes to image formation at the maximum image height position passes, when measured perpendicularly with respect to the optical axis, and $\phi_1$ denotes a maximum diameter of an area on the surface nearest to the object of the object-side lens component through which an axial light beam of the image forming optical system passes, when measured perpendicularly with respect to the optical axis.

Figure 3:
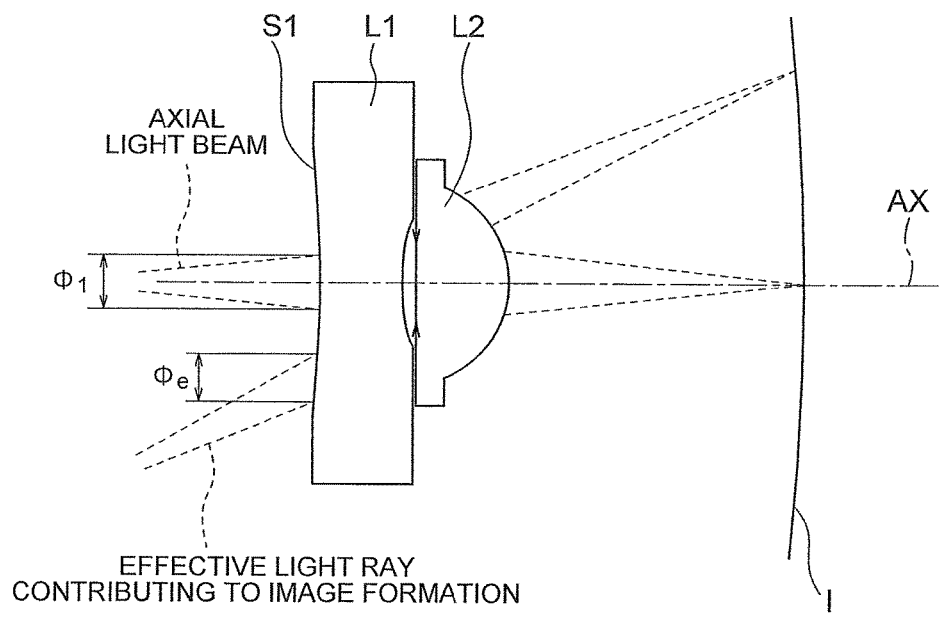
FIG. 3 is still another diagram illustrating parameters used in conditional expressions.

FIG. 3 is a diagram illustrating parameters $\phi_e$ and $\phi_1$. Here, $\phi_e$ denotes the maximum diameter of an area on a surface S1 nearest to the object of an object-side lens component L1 through which an effective light beam that contributes to image formation at the maximum image height position passes, when measured perpendicularly with respect to an optical axis AX, and $\phi1$ denotes the maximum diameter of an area on the surface S1 nearest to the object of the object-side lens component L1 through which an axial light beam of the image forming optical system passes, when measured perpendicularly with respect to the optical axis AX.

Since an occurrence of shading is suppressed by satisfying the conditional expression (6), it is advantageous for reducing a change in the amount of light on the optical axis and off the optical axis, and also for making appropriate the angle of incidence of a light ray on the curved image pickup surface.

It is preferable that the following conditional expression (6-1) is satisfied instead of the conditional expression (6).

$$-2.5<(EXP/f)/(\phi_e/\phi_1)<-1.3 \qquad (6-1)$$

By making so as not to exceed an upper limit value of the conditional expressions (6) and (6-1), it becomes easy to make a difference in a beam diameter of axial light and off-axis light small, and it is advantageous for securing peripheral illumination. Or, by making an arrangement such that the exit-pupil position does not become too close to the image pickup surface, it becomes easy to make an angle of incidence of a light ray on the curved image pickup surface small, and to suppress the chromatic shading.

By making so as not to fall below a lower limit value of the conditional expression (6-1), it becomes easy to prevent the exit-pupil position form becoming too far from the image pickup surface. Accordingly, it becomes easy to suppress the angle of incidence of a light ray on the curved image pickup surface, and to suppress the chromatic shading.

It is preferable that the image pickup apparatus according to the present embodiment includes an illumination unit, and a transparent cover which simultaneously covers a front surface of both the image forming optical system and the illumination unit. Accordingly, it is possible to capture an image with favorable optical performance while irradiating an image.

Moreover, it is preferable that the image pickup apparatus according to the present embodiment is constructed as a capsule endoscope. Accordingly, it is possible to achieve a capsule endoscope having a small size and a favorable optical performance.

An image pickup apparatus according to a second embodiment includes an image forming optical system having lens components, and an image pickup unit, wherein the lens component is a lens having only two surfaces that are in contact with air in an effective optical path namely, an object-side surface and an image-side surface, and the effective optical path is an optical path through which a light beam that contributes to image formation passes, and the image forming optical system includes in order from an object side to an image side, two lens components namely, an object-side lens component and an image-side lens component, and the image pickup unit has an image pickup surface curved to be concave toward the object side, which is disposed on the image side of the image forming optical system, and a surface nearest to an object of the object-side lens component is one of a flat surface and a surface having a concave shape toward the object side, and a surface nearest to an image of the image-side lens component is a curved surface, and the following conditional expression (A1) is satisfied:

$$0<L/TL\leq 0.4 \qquad (A1),$$

where,

L denotes a distance on an optical axis from a surface nearest to the image of the object-side lens component up to a surface nearest to the object of the image-side lens component, and TL denotes a distance on the optical axis from the surface nearest to the object of the object-side lens component up to the image pickup surface.

In an optical system that forms a curved image, correction of a curvature of field is acceptable. Consequently, in the optical system that forms the curved image, a load of aberration correction is reduced as compared to that in an optical system that forms a flat image.

For instance, in the optical system that forms the curved image, it is possible to reduce a lens that corrects Petzval's sum. Consequently, it is possible to reduce the number of lens components, and to make the optical system small-sized.

Moreover, in the optical system that forms the flat image, for correcting the curvature of field, it is necessary to dispose a lens for correction at a position away from an aperture stop. However, when the lens for correction is disposed, an outer diameter of the optical system becomes large, and the number of lens components further increase. In such manner, the lens for correction is one of the factors that make the outer diameter of the optical system large, and increase the number of lens components.

Whereas, in the optical system that forms the curved image, there is no need to dispose the lens for correction. Consequently, in the optical system that forms the curved image, it is possible to make the outer diameter small, and to further reduce the number of lenses.

Furthermore, by receiving an image of an optical system on an image pickup element having a curved image pickup surface, correction of a distortion becomes easy. Moreover, there is no need to make the optical system to be a telecentric optical system for letting a light ray to be incident almost perpendicularly on the image pickup surface. Consequently, in the optical system that forms the curved image, a degree of freedom of designing to achieve both of a small-sizing and an optical performance is widened.

The image forming optical system in the present embodiment is also an optical system that forms the curved image. Therefore, it is possible to reduce the number of lens components, and to make the optical system small-sized. Furthermore, since the degree of freedom of designing widens, it is possible to realize an optical system having a superior imaging performance with lesser number of lens components.

The image pickup apparatus according to the present embodiment has the image forming optical system which includes in order from the object side to the image side, two lens components namely, the object-side lens component and the image-side lens component when the lens component is let to be a lens having only two surfaces that are in contact with air in an effective optical path namely, an object-side surface and an image-side surface.

In such manner, according to the present embodiment, in spite of two lens components, which is a small number, it is possible to achieve a favorable imaging performance along the image pickup surface curved to be concave toward the object side, while securing the angle of view and the amount of the curvature of field optimally.

Then, it is preferable to reduce aberration by letting the image-side surface of the image-side lens component to be a curved surface. The conditional expression (A1) will be described below.

The conditional expression (A1) regulates an appropriate distance between the object-side lens component and the image-side lens component.

When the distance between the object-side lens component and the image-side lens component is excessively large, a size of one or both of the object-side lens component and the image-side lens component is susceptible to become large. Particularly, in a case of widening the angle of view of the image forming optical system, since an angle of incidence of a light ray on refracting surfaces of the two lens components that are face-to-face becomes large, it is susceptible to become a cause of aberration.

By making so as not to exceed an upper limit value of the conditional expression (A1), it becomes easy to shorten the distance between the object-side lens component and the image-side lens component, and it is advantageous for small-sizing of the optical system. In particular, in a case of widening the angle of view of the image forming optical system, it is also possible to make small the angle of incidence of a light ray on the refractive surfaces that are face-to-face, and this is advantageous for reducing occurrence of various aberrations.

For the conditional expression (A1), it is preferable to let the upper limit value to be 0.25, more preferably to be 0.15, and all the more preferably to be 0.05.

Moreover, in the image pickup apparatus according to the present embodiment, it is preferable that the surface nearest to the image of the image-side lens component is a surface which is convex shape toward the image side.

By letting the surface nearest to the image of the image-side lens component disposed close to an image plane to be convex shape toward the image side, it is possible to reduce an astigmatism.

Moreover, in the image pickup apparatus according to the present embodiment, it is preferable that the surface nearest to the object of the object-side lens component is an aspheric surface.

As described above, in the image pickup apparatus according to the present embodiment, the curved image is formed. The curved image is picked up by the image pickup element, for instance. When an amount of curvature of the curved image is large, an amount of curvature of the image pickup surface of the image pickup element also becomes large. Since there is a limit for the amount of curvature of the image pickup surface while manufacturing, it is preferable to let the amount of curvature of the curved image to be an appropriate amount.

Moreover, in the curved image, it is preferable that an aberration is corrected favorably.

Consequently, the image forming optical system is sought to have an appropriate amount of curvature of field that occurs, while having a wide angle of view, and also to form a curved image in which, an aberration other than the curvature of field is corrected favorably. Therefore, by letting the object-side optical surface to be an aspheric surface, it is advantageous for forming a wide-angle curved image in which the amount of the curvature of field that occurs is appropriate, and in which an aberration other than the curvature of field has been corrected favorably.

Moreover, in the image pickup apparatus according to the present embodiment, it is preferable that the surface nearest to the image of the image-side lens component is a surface which is convex shape toward the image side, and the following conditional expression (A2) is satisfied:

$$0 \leq R_{2e}/R_{11} < 1.0 \quad (A2),$$

where, $R_{11}$ denotes a radius of curvature of the surface nearest to the object of the object-side lens component, and $R_{2e}$ denotes a radius of curvature of the surface nearest to the image of the image-side lens component.

The conditional expression (A2) regulates a relationship between the radius of curvature of the surface nearest to the object of the object-side lens component and the radius of curvature of the surface nearest to the image of the image-side lens component.

For achieving favorable imaging performance along the image pickup surface which is curved to be concave toward the object side, it is preferable to balance an amount of curvature of field that occurs due to the surface nearest to the object of the object-side lens component and an amount of astigmatism that occurs due to the surface nearest to the image of the image-side lens component. For this, it is preferable to satisfy the conditional expression (A2).

By satisfying the conditional expression (A2), it is advantageous for both of adjusting the amount of curvature of field that occurs due to the surface nearest to the object of the object-side lens component and reducing the astigmatism due to the surface nearest to the image of the image-side lens component.

By making so as not to exceed an upper limit value of the conditional expression (A2), it becomes easy to let the radius of curvature of the surface nearest to the object of the object-side lens component to be longer, and thereby it is preferable to suppress the amount of curvature of field from being excessive. Or, it becomes easy to make the radius of curvature of the surface nearest to the image of the image-side lens component small, and thereby it is preferable to suppress the occurrence of astigmatism. As a result, it is advantageous for achieving favorable imaging performance along the image pickup surface which is curved to be concave toward the object side.

By making so as not to fall below a lower limit value of the conditional expression (A2), it is advantageous for both of widening the angle of view and securing the back focus.

For the conditional expression (A2), it is preferable to let the lower limit value to be 0.02, and more preferably to be 0.04. Moreover, for the conditional expression (A2), it is preferable to let the upper limit value to be 0.8, and more preferably to be 0.6.

Moreover, in the image pickup apparatus according to the present embodiment, it is preferable that the abovementioned conditional expression (2) is satisfied:

$$0<|R_{2e}/R_{img}|\leq 2.0 \qquad (2),$$

where, $R_{2e}$ denotes the radius of curvature of the surface nearest to the image of the image-side lens component, and $R_{img}$ denotes a minimum value of a radius of curvature of a virtual spherical surface which includes an apex and a point at which a light ray incident on the image forming optical system at a half angle of view of 60 degrees intersects the image pickup surface, letting a point of intersection of the optical axis and the image pickup surface to be the apex.

The technical significance of the conditional expression (2) is as mentioned above.

Moreover, in the image pickup apparatus according to the present embodiment, it is preferable that the abovementioned conditional expression (3) is satisfied:

$$L_{1e}/TL \leq 0.65 \qquad (3),$$

where, $L_{1e}$ denotes a distance on the optical axis from the surface nearest to the object of the object-side lens component up to the surface nearest to the image of the image-side lens component, and TL denotes the distance on the optical axis from the surface nearest to the object of the object-side lens component up to the image pickup surface.

In the image pickup optical system according to the present embodiment, the conditional expression (3-1) may be satisfied. The technical significance of the conditional expressions (3) and (3-1) are as mentioned above.

Moreover, in the image pickup apparatus according to the present embodiment, it is preferable that the object-side lens component has a negative refractive power and the image-side lens component has a positive refractive power.

In such manner, it is possible to achieve a favorable imaging performance along the image pickup surface curved to be concave toward the object side, while securing the angle of view and the amount of the curvature of field optimally.

An image forming optical system according to the first embodiment includes a plurality of lens components, wherein the lens component is a lens having only two surfaces that are in contact with air in an effective optical path namely, an object-side surface and an image-side surface, and the effective optical path is an optical path through which a light beam that contributes to image formation passes, and the plurality of lens components include in order from an object side to an image side, two lens components namely, an object-side lens component and an image-side lens component, and an image is formed on an image pickup surface which is curved to be concave toward the object side, and the following conditional expression (A5) is satisfied:

$$L_{1e}/R_{11} \leq 0 \qquad (A5),$$

where, $L_{1e}$ denotes a distance on an optical axis from a surface nearest to an object of the object-side lens component up to a surface nearest to the image of the image-side lens component, and $R_{11}$ denotes a radius of curvature of the surface nearest to the object of the object-side lens component.

By satisfying the conditional expression (A5), it is possible to make a lens portion thin while securing a wide angle of field.

It is preferable that the following conditional expression (A5-1) is satisfied instead of the conditional expression (A5).

$$-1.5 < L_{1e}/R_{11} \leq 0 \qquad (A5-1)$$

By making so as not to exceed an upper limit value of the conditional expressions (A5) and (A5-1), it becomes easy to let the surface nearest to the object of the object-side lens component to be either flat or concave in a paraxial region, and it is advantageous for making the back focus long and the lens portion small-sized. Or, it is advantageous for suppressing curvature of the image pickup surface from becoming excessive, and for reducing a manufacturing cost of the image pickup element.

By making so as not to fall below a lower limit value of the conditional expression (A5-1), it is advantageous for reduction of overall length of lenses and for making it light-weight.

For the conditional expression (A5-1), it is preferable to let the lower limit value to be −1.0, and more preferably to be −0.5. For conditional expressions (A5) and (A5-1), it is preferable to let the upper limit value to be −0.05.

An image forming optical system according to the second embodiment includes a plurality of lens components, wherein the lens component is a lens having only two surfaces that are in contact with air in an effective optical path namely, an object-side surface and an image-side surface, and the effective optical path is an optical path through which a light beam that contributes to image formation passes, and the plurality of lens components include in order from an object side to an image side, two lens components namely, an object-side lens component and an image-side lens component, and an image is formed on an image pickup surface which is curved to be concave toward the object side, and the following conditional expression (A6) is satisfied:

$$PS_{inv}/R_{11} \leq 0 \qquad (A6),$$

where, $R_{11}$ denotes a radius of curvature of a surface nearest to an object of the object-side lens component, and $PS_{inv}$ denotes an inverse number of Petzval's sum for the image forming optical system, and here Petzval's sum PS is expressed by the following expression:

$$PS = \sum_{i=1}^{k} \frac{1}{n_i \times f_i}$$

where, i denotes an order from the object side of lenses in the image forming optical system, k denotes total number of lenses in the image forming optical system, $n_i$ denotes a refractive index for a d-line of an $i^{th}$ lens, and $f_i$ denotes a focal length of the $i^{th}$ lens.

By satisfying conditional expression (A6), it is advantageous for achieving favorable imaging performance along the image pickup surface curved to be concave toward the object side, while securing the angle of view and maintaining the amount of the curvature of field to be optimum.

It is preferable that the following conditional expression (A6-1) is satisfied instead of the conditional expression (A6).

$$-2.5 < PS_{inv}/R_{11} \times 0 \quad (A6\text{-}1)$$

By making so as not to exceed an upper limit value of the conditional expressions (A6) and (A6-1), it becomes easy to let the surface nearest to the object of the object-side lens component to be either flat or concave in a paraxial region, and it is advantageous for making the back focus long, and the lens portion small-sized. Or, it is advantageous for suppressing curvature of the image pickup surface from becoming excessive, and for reducing the manufacturing cost of the image pickup element.

By making so as not to fall below a lower limit value of the conditional expression (A6-1), it becomes easy to make Petzval's sum large, and it is advantageous for optimizing the amount of curvature of field that occurs.

For the conditional expression (A6-1), it is preferable to let the lower limit value to be −2.0, and more preferably to be −1.5. For the conditional expressions (A6) and (A6-1), it is preferable to let the upper limit value to be −0.1.

Moreover, in the image forming optical system according to the present embodiment, it is preferable that the surface nearest to the object of the object-side lens component is one of a flat surface and a surface having a concave shape toward the object side.

By making such arrangement, it is advantageous for achieving a favorable imaging performance along the image pickup surface curved to be concave toward the object side, while securing the angle of view and amount of curvature of field optimally.

Moreover, in the image forming optical system according to the present embodiment, it is preferable that the surface nearest to the image of the image-side lens component is a surface which is convex shape toward the image side.

In such manner, by letting the surface nearest to the image of the image-side lens component disposed close to an image plane to be convex shape, it is advantageous for reducing an astigmatism.

Moreover, in the image forming optical system according to the present embodiment, it is preferable that the surface nearest to the object of the object-side lens component is an aspheric surface.

Such arrangement is preferable as it enables to secure the angle of view and the amount of the curvature of field more optimally.

Moreover, in the image forming optical system according to the present embodiment, it is preferable that the object-side lens component has a negative refractive power, and the image-side lens component has a positive refractive power.

By making such arrangement, it is advantageous for achieving a favorable imaging performance along the image pickup surface curved to be concave toward the object side, while securing the angle of view and amount of curvature of field optimally.

Moreover, the image pickup apparatus according to the present embodiment includes the abovementioned image forming optical system, an image pickup unit having an image pickup surface curved to be concave toward the object side, which is disposed on the image side of the image forming optical system.

In such manner, it is possible to achieve a favorable imaging performance along the image pickup surface curved to be concave toward the object side, while securing the angle of view and amount of curvature of field optimally.

Moreover, a capsule endoscope according to the present embodiment includes the abovementioned image forming optical system, an image pickup unit having an image pickup surface curved to be concave toward the object side, which is disposed on the image side of the image forming optical system, and a cover portion having a dome shape, which is disposed on the object side of the image forming optical system.

In such manner, it is possible to achieve a favorable imaging performance along the image pickup surface curved to be concave toward the object side, while securing the angle of view and the amount of the curvature of field optimally.

An image forming optical system according to a third embodiment of the present invention includes a plurality of lens components, and an aperture stop which limits an axial light beam, wherein the lens component is a lens having only two surfaces that are in contact with air in an effective optical path namely, an object-side surface and an image-side surface, and the effective optical path is an optical path through which a light beam that contributes to image formation passes, and the plurality of lens components include in order from an object side to an image side, two lens components namely, an object-side lens component and an image-side lens component, and an image is formed on an image pickup surface which is curved to be concave toward the object side, and the following conditional expression (5) is satisfied:

$$PS \times EXP < -0.7 \quad (5),$$

where,

PS denotes Petzval's sum for the image forming optical system, and here

Petzval's sum PS is expressed by the following expression:

$$PS = \sum_{i=1}^{k} \frac{1}{n_i \times f_i}$$

where, i denotes an order of lenses from the object side in the image forming optical system, k denotes total number of lenses in the image forming optical system, $n_i$ denotes a refractive index for a d-line of an $i^{th}$ lens, $f_i$ denotes a focal length of the $i^{th}$ lens, and EXP denotes a distance along an optical axis from the image up to a paraxial exit pupil position of the image forming optical system, and is let to be negative when the paraxial exit pupil is on the object side of the image.

In the image pickup optical system according to the present embodiment, the conditional expression (5-1) may be satisfied. The technical significance of the conditional expressions (5) and (5-1) are as mentioned above.

Moreover, in the image forming optical system according to the present embodiment, it is preferable that the aperture stop is disposed between the object-side lens component and the image-side lens component, the abovementioned conditional expression (3) is satisfied:

$$L_{1e}/TL \leq 0.65 \quad (3),$$

where, $L_{1e}$ denotes a distance on the optical axis from the surface nearest to the object of the object-side lens component up to the surface nearest to the image of the image-side lens component, and TL denotes a distance on the optical axis from the surface nearest to the object of the object-side lens component up to the image pickup surface.

In the present embodiment, by disposing the aperture stop between the object-side lens component and the image-side lens component for instance, it is further advantageous for small-sizing of each lens component. Moreover, it becomes easy to maintain an optical performance by such arrangement.

In the image pickup optical system according to the present embodiment, the conditional expression (3-1) may be satisfied. The technical significance of the conditional expressions (3) and (3-1) are as mentioned above.

Moreover, in the image forming optical system according to the present embodiment, it is preferable that the surface nearest to the object of the object-side lens component is one of a flat surface and a surface having a concave shape toward the object side.

By making such arrangement, it is possible to achieve a favorable imaging performance along the image pickup surface curved to be concave toward the object side, while securing the angle of view and the amount of the curvature of field optimally.

Moreover, in the image forming optical system according to the present embodiment, it is preferable that the surface nearest to the object of the object-side lens component is a surface having a concave shape portion which is concave shape toward the object side in a meridional direction, in at least an off-axis effective surface.

It is possible to achieve a favorable imaging performance along the image pickup surface curved to be concave toward the object side, while securing the angle of view and the amount of curvature of field optimally.

Moreover, in the image forming optical system according to the present embodiment, it is preferable that the surface nearest to the image of the image-side lens component is a surface which is convex shape toward the image side.

By letting the surface near the image plane to have such shape, it is possible to reduce the astigmatism.

Moreover, in the image forming optical system according to the present embodiment, it is preferable that the surface nearest to the object of the object-side lens component is an aspheric surface.

Such arrangement is preferable as it is advantageous to achieve both of securing a wide angle of view and reduction in the amount of curvature of field that occurs.

Moreover, the image pickup apparatus according to the present embodiment includes the abovementioned image forming optical system, an image pickup unit having an image pickup surface curved to be concave toward the object side, which is disposed on the image side of the image forming optical system.

By making such arrangement, it is possible to realize an image pickup apparatus having a favorable optical performance, while being small-sized with a small number of lens components.

Moreover, an image forming optical system according to a fourth embodiment of the present invention includes a plurality of lens components, and an aperture stop which limits an axial light beam, wherein the lens component is a lens having only two surfaces that are in contact with air in an effective optical path namely, an object-side surface and an image-side surface, and the effective optical path is an optical path through which a light beam that contributes to image formation passes, and the plurality of lens components include in order from an object side to an image side, two lens components namely, an object-side lens component and an image-side lens component, and an image is formed on an image pickup surface which is curved to be concave toward the object side, and the abovementioned conditional expression (6) is satisfied:

$$(EXP/f)/(\phi_e/\phi_1) < -1.3 \tag{6}$$

where,

EXP denotes a distance along an optical axis from the image up to a paraxial exit pupil position of the image forming optical system, and is let to be negative when the paraxial exit pupil position is on the object side of the image, f denotes a focal length of the image forming optical system, $\phi_e$ denotes a maximum diameter of an area on the surface nearest to the object of the object-side lens component, through which an effective light beam that contributes to image formation at a maximum image height position passes, when measured perpendicularly with respect to an optical axis, and $\phi_1$ denotes a maximum diameter of an area on the surface nearest to object of the object-side lens component through which an axial light beam of the image forming optical system passes, when measured perpendicularly with respect to an optical axis.

The conditional expression (6-1) may be satisfied. The technical significance of the conditional expressions (6) and (6-1) are as mentioned above.

Moreover, in the image forming optical system according to the present embodiment, it is preferable that the abovementioned conditional expression (3) is satisfied:

$$L_{1e}/TL \leq 0.65 \tag{3}$$

where, $L_{1e}$ denotes a distance on the optical axis from the surface nearest to the object of the object-side lens component up to the surface nearest to the image of the image-side lens component, and TL denotes a distance on the optical axis from the surface nearest to the object of the object-side lens component up to the image pickup surface.

In the image pickup optical system according to the present embodiment, the conditional expression (3-1) may be satisfied. The technical significance of the conditional expressions (3) and (3-1) are as mentioned above.

Moreover, in the image forming optical system according to the present embodiment, it is preferable that the surface nearest to the object of the object-side lens component is one of a flat surface and a surface having a concave shape toward the object side.

By making such arrangement, it is possible to achieve a favorable imaging performance along the image pickup surface curved to be concave toward the object side, while securing the angle of view and the amount of the curvature of field optimally.

Moreover, in the image forming optical system according to the present embodiment, it is preferable that the surface nearest to the object of the object-side lens component is a surface having a concave shape portion which is concave shape toward the object side in a meridional direction, in at least an off-axis effective surface.

In such manner, it is possible to achieve a favorable imaging performance along the image pickup surface curved to be concave toward the object side, while securing the angle of view and the amount of the curvature of field optimally.

Moreover, in the image forming optical system according to the present embodiment, it is preferable that the surface nearest to the image of the image-side lens component is a surface which is convex shape toward the image side.

By letting the surface near the image plane to have such shape, it is possible to reduce the astigmatism.

Moreover, in the image forming optical system according to the present embodiment, it is preferable that the surface nearest to the object of the object-side lens component is an aspheric surface.

Such arrangement is preferable as it is advantageous to achieve both of securing a wide angle of view and reduction in the amount of curvature of field that occurs.

The image pickup apparatus according to the present embodiment includes the abovementioned image forming optical system, an image pickup unit having an image pickup surface curved to be concave toward the object side, which is disposed on the image side of the image forming optical system.

By making such arrangement, it is possible to realize an image pickup apparatus having a favorable optical performance, while being small-sized with a small number of lens components.

The image pickup apparatus according to the present embodiment further includes an illumination unit, and a cover portion which is disposed on the object side of the image forming optical system.

Accordingly, it is possible to capture an image with a favorable optical performance while illuminating an object.

An image forming optical system according to a fifth embodiment of the present invention, which forms an image curved to be concave toward an object side, includes an object-side optical surface which is positioned nearest to an object, and an image-side optical surface which is positioned nearest to the image, and the following conditional expressions (B1), (B2), (B3), and (B4) are satisfied:

$$0 \le |R_e/R_1| < 0.8 \quad (B1),$$

$$R_e/TL' < 0 \quad (B2),$$

$$EXP_{60}/f < 0 \quad (B3), \text{ and}$$

$$0 < Y_1 \times 2/f < 2 \quad (B4),$$

where, $R_1$ denotes a paraxial radius of curvature of the object-side optical surface, $R_e$ denotes a paraxial radius of curvature of the image-side optical surface, TL' denotes a distance on an optical axis from the object-side optical surface up to the image, $EXP_{60}$ denotes an exit-pupil position by a light ray incident on the image forming optical system at a half angle of view of 60 degrees, f denotes a focal length of the image forming optical system, and $Y_1$ denotes a maximum light ray height in a predetermined area, and here the predetermined area is an area of the object-side optical surface through which an effective light beam passes.

In an optical system that forms a curved image, correction of a curvature of field is acceptable. Consequently, in the optical system that forms the curved image, a load of aberration correction is reduced as compared to that in an optical system that forms a flat image.

For instance, in the optical system that forms the curved image, it is possible to reduce a lens that corrects Petzval's sum. Consequently, it is possible to reduce the number of lens components, and to make the optical system small-sized.

Moreover, in the optical system that forms the flat image, for correcting the curvature of field, it is necessary to dispose a lens for correction at a position away from an aperture stop. However, when the lens for correction is disposed, an outer diameter of the optical system becomes large, and the number of lens components further increase. In such manner, the lens for correction is one of the factors that make the outer diameter of the optical system large, and increase the number of lens components.

Whereas, in the optical system that forms the curved image, there is no need to dispose the lens for correction. Consequently, in the optical system that forms the curved image, it is possible to make the outer diameter small, and to further reduce the number of lenses.

Moreover, regarding a proportion of peripheral illumination, or in other words, regarding a proportion of the amount of light in the peripheral area with respect to an amount of light in a central area, a degradation of the proportion is suppressed. Moreover, regarding a distortion, further occurrence of distortion is suppressed.

Furthermore, in a case of receiving an image of an optical system by the image pickup element having the curved image pickup surface, the optical system is not necessarily let to be telecentric in order to make a light ray incident perpendicularly to the image pickup surface. Consequently, in the optical system that forms a curved image, a degree of freedom of designing for achieving both of small-sizing and optical performance is widened.

The image forming optical system according to the present embodiment is also an optical system that forms a curved image. Therefore, it is possible to reduce the number of lens components and to make the optical system small-sized. Furthermore, since the degree of freedom of designing is widened, it is possible to realize an optical system having a superior imaging performance while securing a wide angle of view such as 120 degrees or more.

The image forming optical system according to the present embodiment includes an object-side optical surface which is positioned nearest to the object, and an image-side optical surface which is positioned nearest to the image, wherein the abovementioned conditional expressions (B1), (B2), (B3), and (B4) are satisfied.

By satisfying the conditional expressions (B1), (B2), (B3), and (B4), it is possible to realize an image forming optical system having a wide angle of view and a superior imaging performance, while being small-sized.

Figure 4:
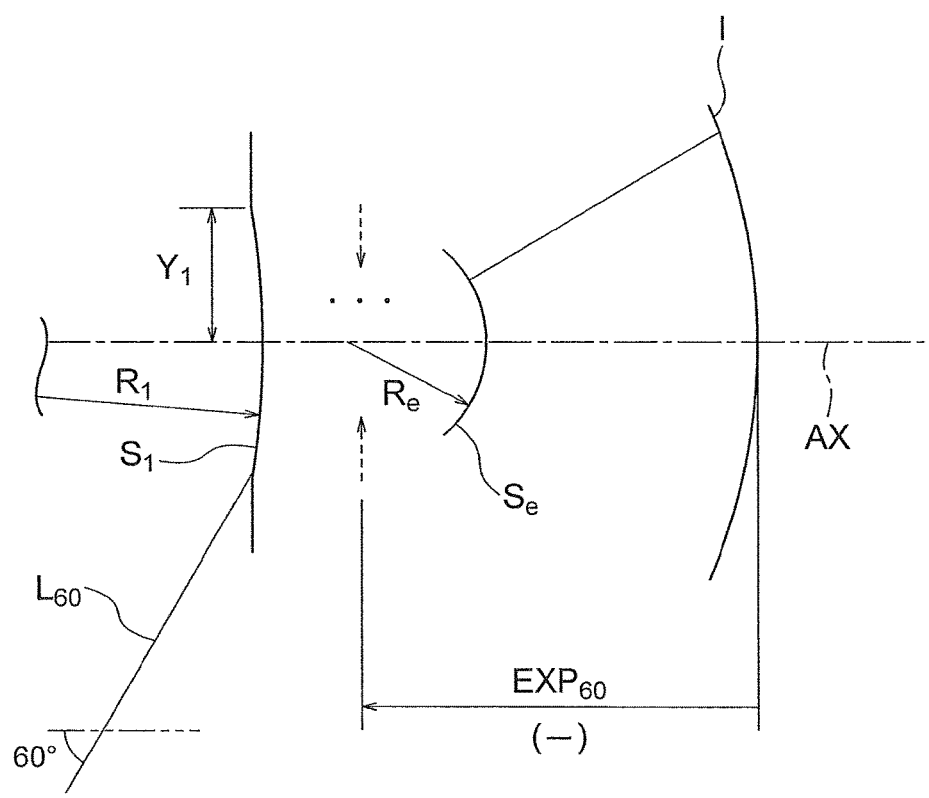
FIG. 4 is still another diagram illustrating parameters used in conditional expressions.
Figure 5A:
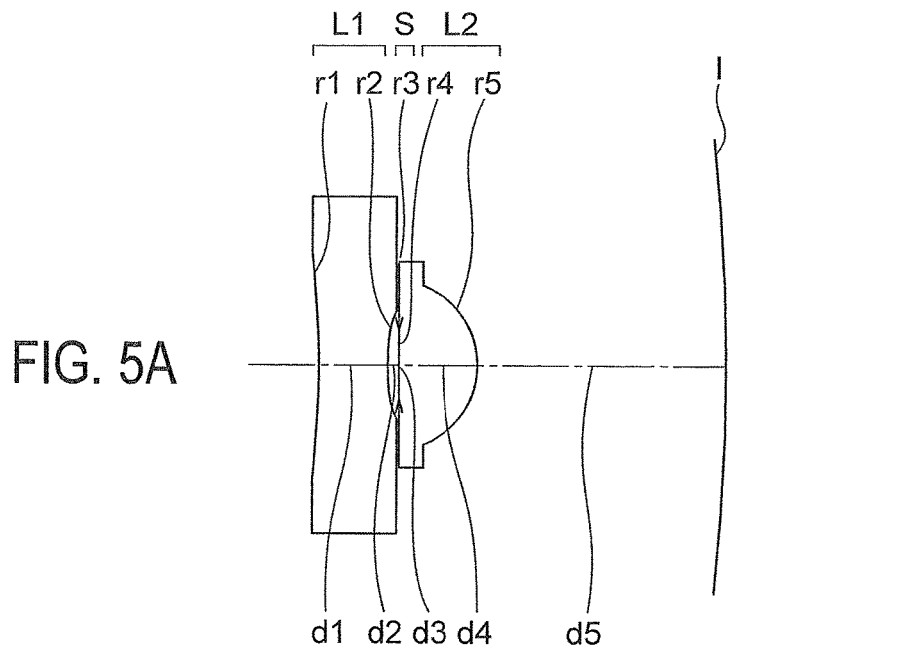
FIG. 5A is a cross-sectional view of an image forming optical system according to an example 1.
Figures 5B, 5C, 5D, 5E:
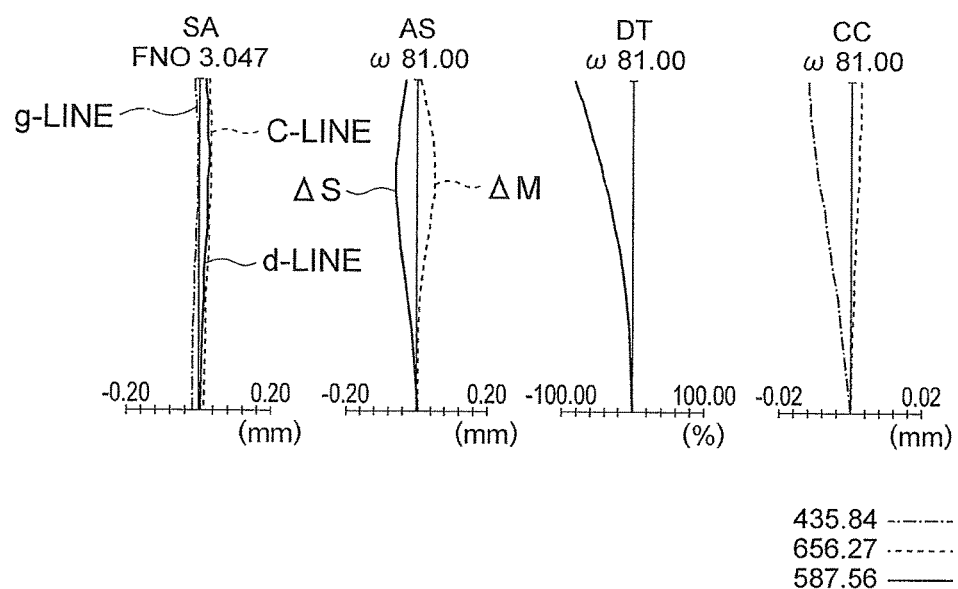
FIG. 5B, FIG. 5C, FIG. 5D, and FIG. 5E are aberration diagrams according to the example 1.
Figure 6A:
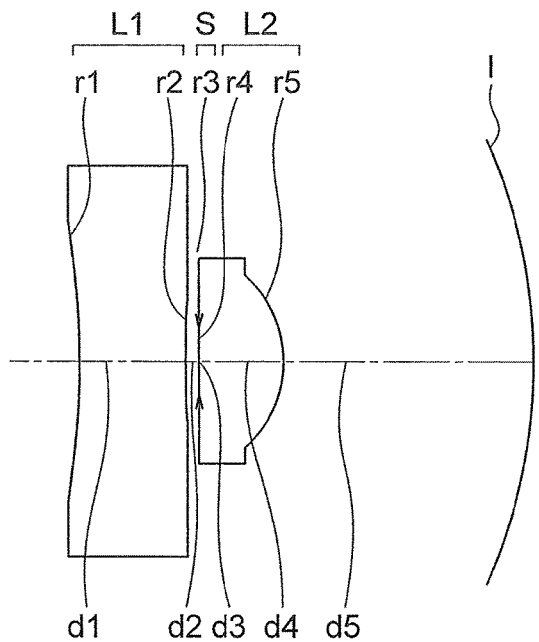
FIG. 6A is a cross-sectional view of an image forming optical system according to an example 2.
Figures 6B, 6C, 6D, 6E:
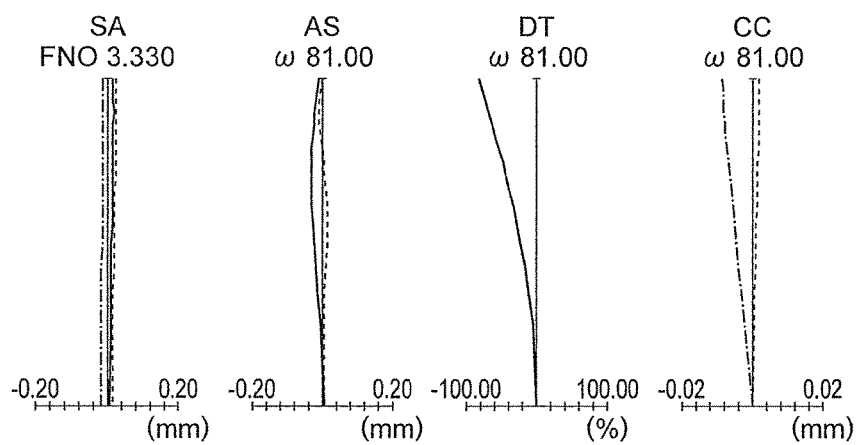
FIG. 6B, FIG. 6C, FIG. 6D, and FIG. 6E are aberration diagrams according to the example 2.
Figure 7A:
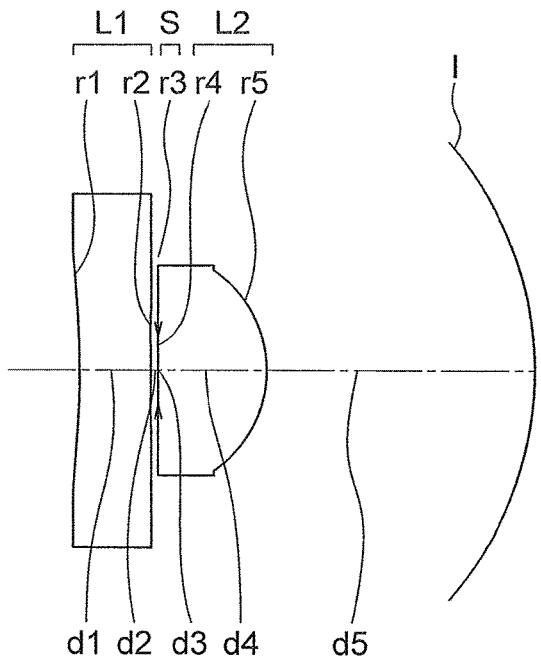
FIG. 7A is a cross-sectional view of an image forming optical system according to an example 3.
Figures 7B, 7C, 7D, 7E:
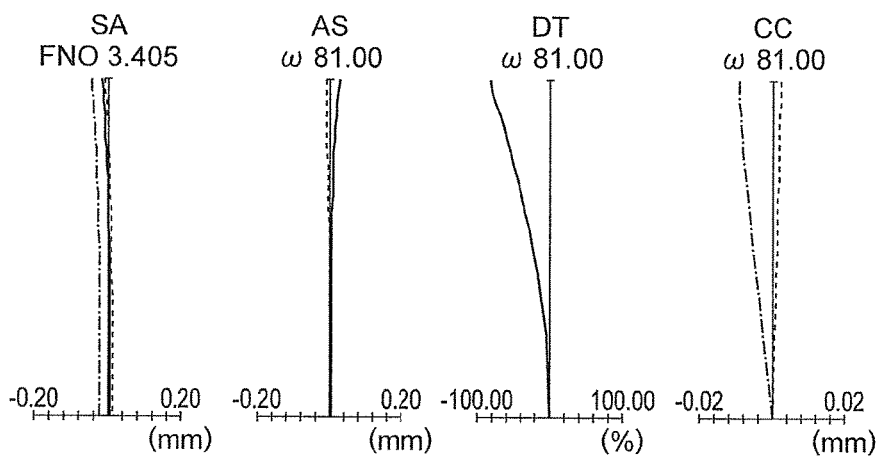
FIG. 7B, FIG. 7C, FIG. 7D, and FIG. 7E are aberration diagrams according to the example 3.
Figure 8A:
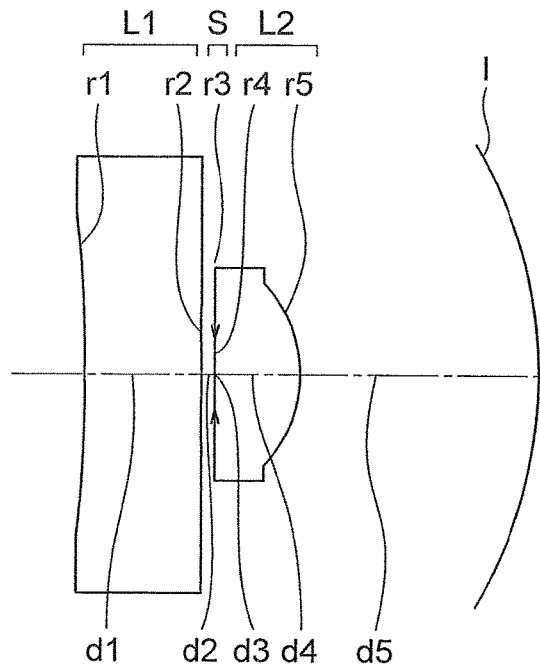
FIG. 8A is a cross-sectional view of an image forming optical system according to an example 4.
Figures 8B, 8C, 8D, 8E:
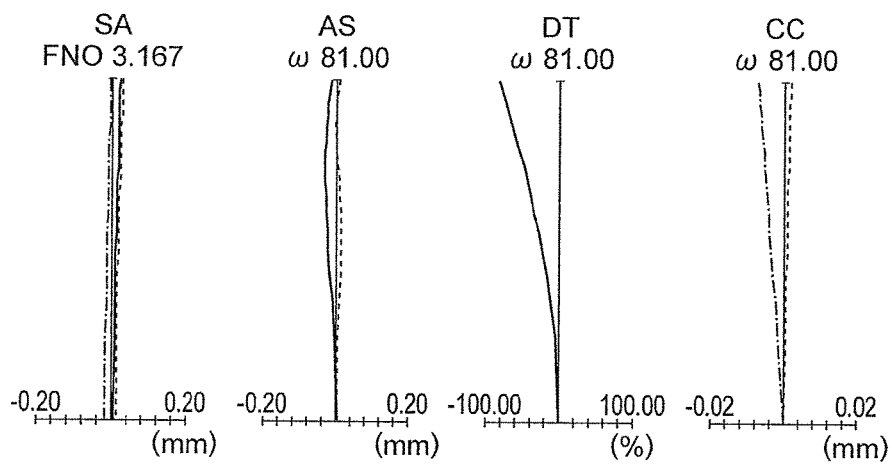
FIG. 8B, FIG. 8C, FIG. 8D, and FIG. 8E are aberration diagrams according to the example 4.
Figure 9A:
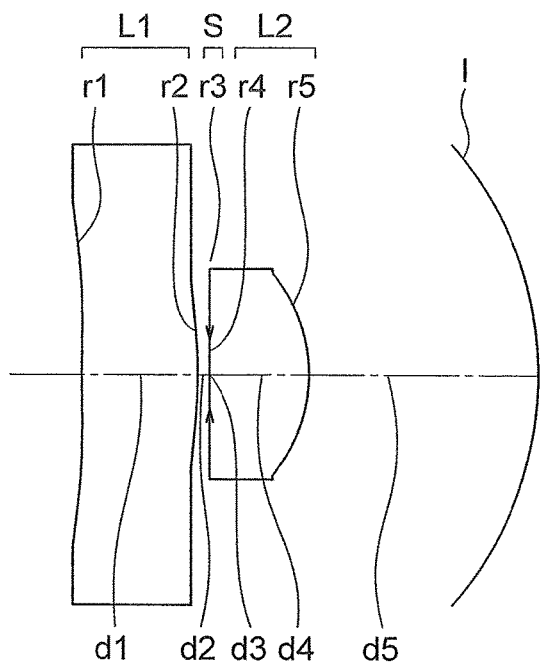
FIG. 9A is a cross-sectional view of an image forming optical system according to an example 5.
Figures 9B, 9C, 9D, 9E:
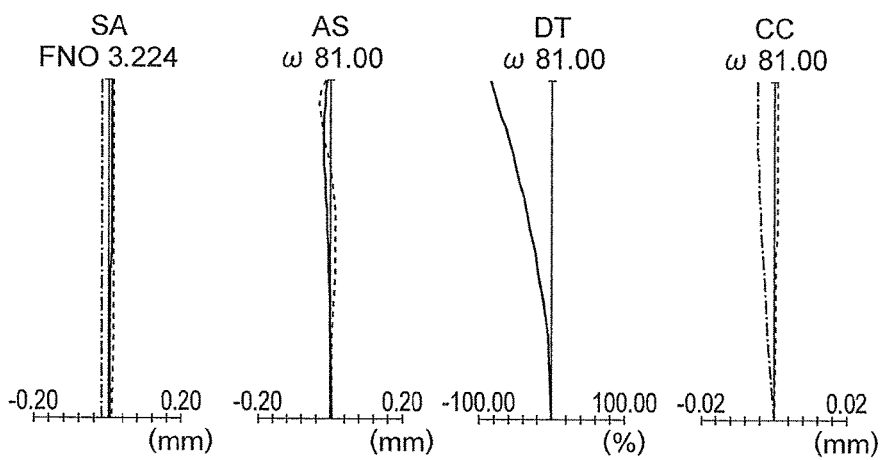
FIG. 9B, FIG. 9C, FIG. 9D, and FIG. 9E are aberration diagrams according to the example 5.
Figure 10A:
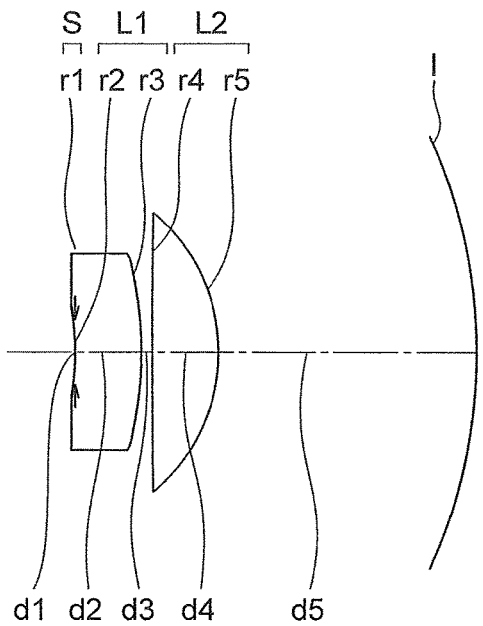
FIG. 10A is a cross-sectional view of an image forming optical system according to an example 6.
Figures 10B, 10C, 10D, 10E:
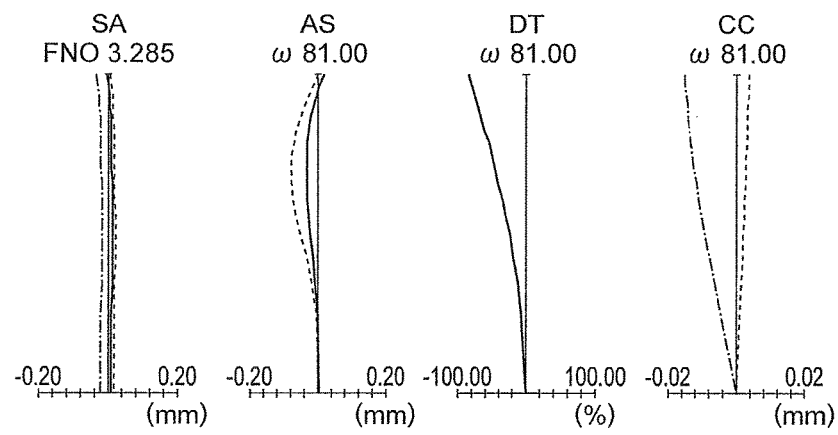
FIG. 10B, FIG. 10C, FIG. 10D, and FIG. 10E are aberration diagrams according to the example 6.
Figure 11A:
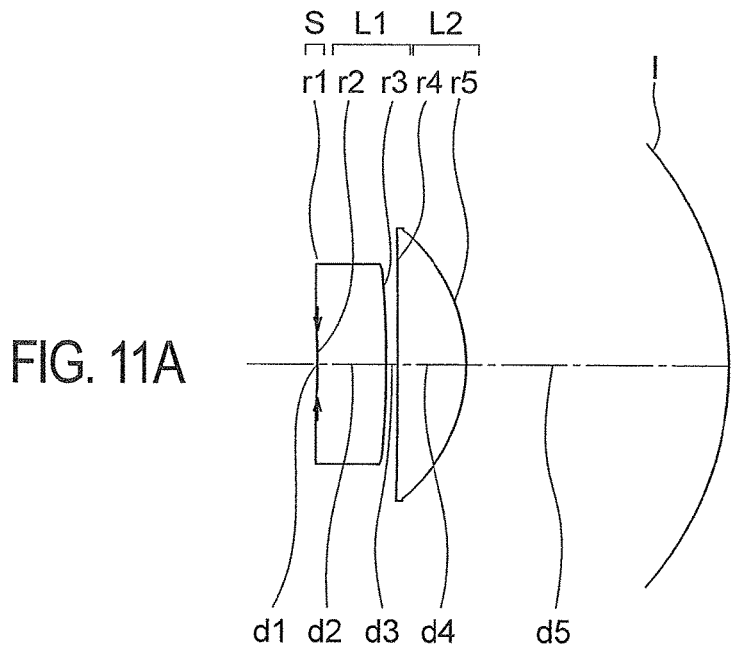
FIG. 11A is a cross-sectional view of an image forming optical system according to an example 7.
Figures 11B, 11C, 11D, 11E:
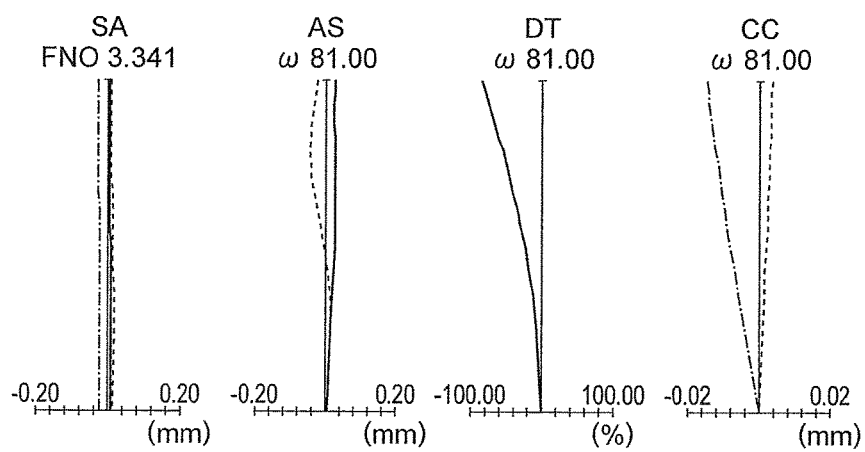
FIG. 11B, FIG. 11C, FIG. 11D, and FIG. 11E are aberration diagrams according to the example 7.
Figure 12A:
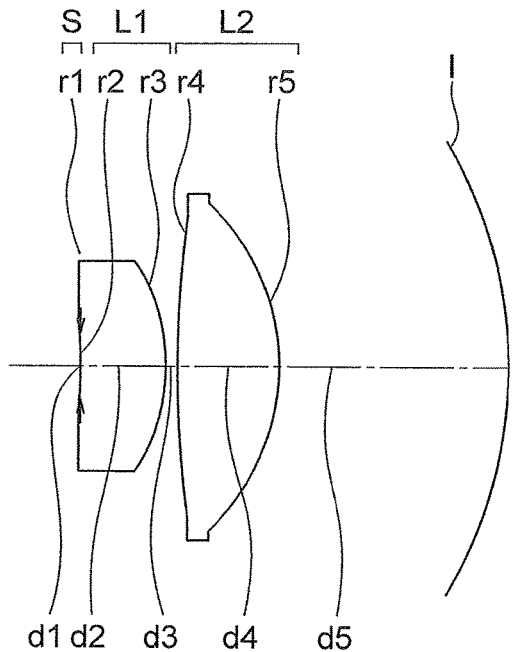
FIG. 12A is a cross-sectional view of an image forming optical system according to an example 8.
Figures 12B, 12C, 12D, 12E:
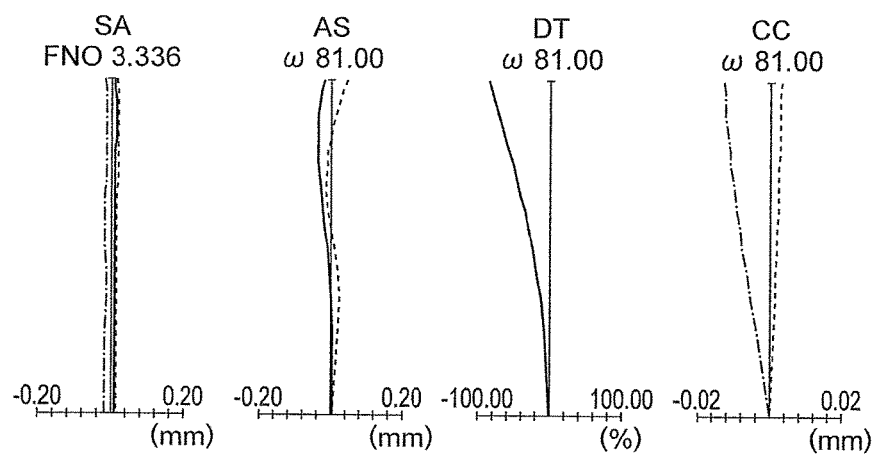
FIG. 12B, FIG. 12C, FIG. 12D, and FIG. 12E are aberration diagrams according to the example 8.
Figure 13A:
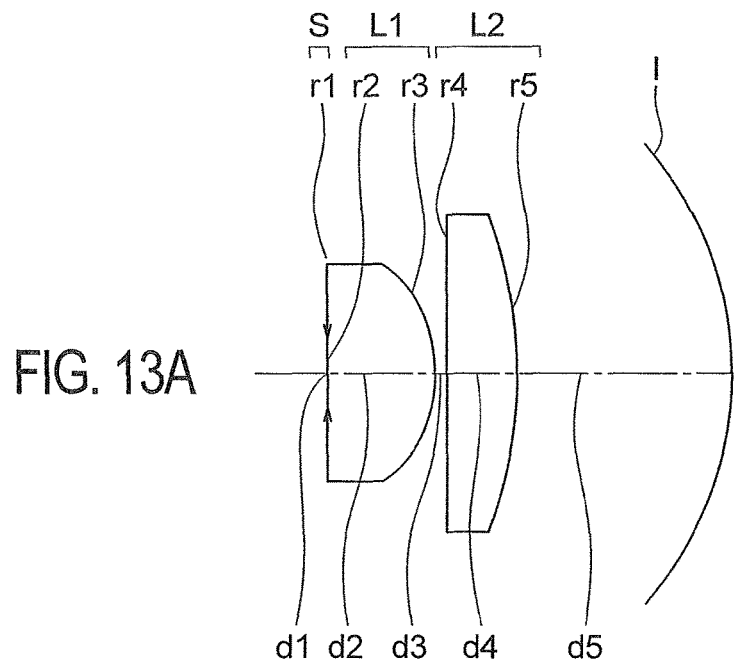
FIG. 13A is a cross-sectional view of an image forming optical system according to an example 9.
Figures 13B, 13C, 13D, 13E:
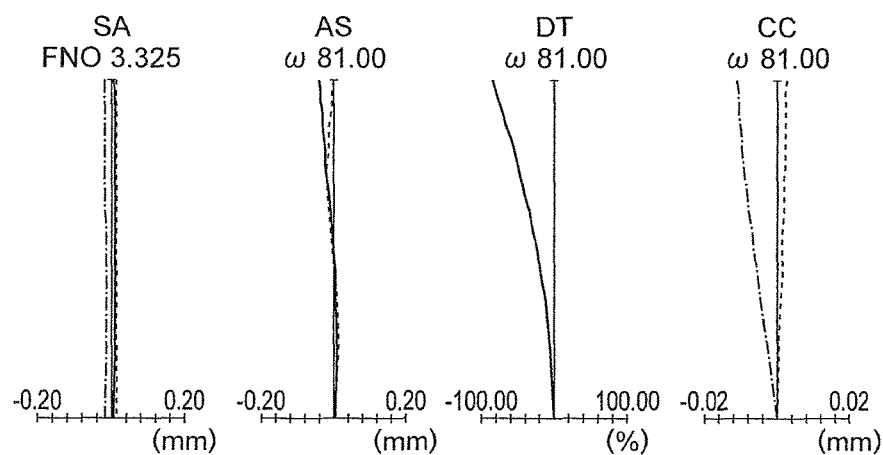
FIG. 13B, FIG. 13C, FIG. 13D, and FIG. 13E are aberration diagrams according to the example 9.
Figure 14A:
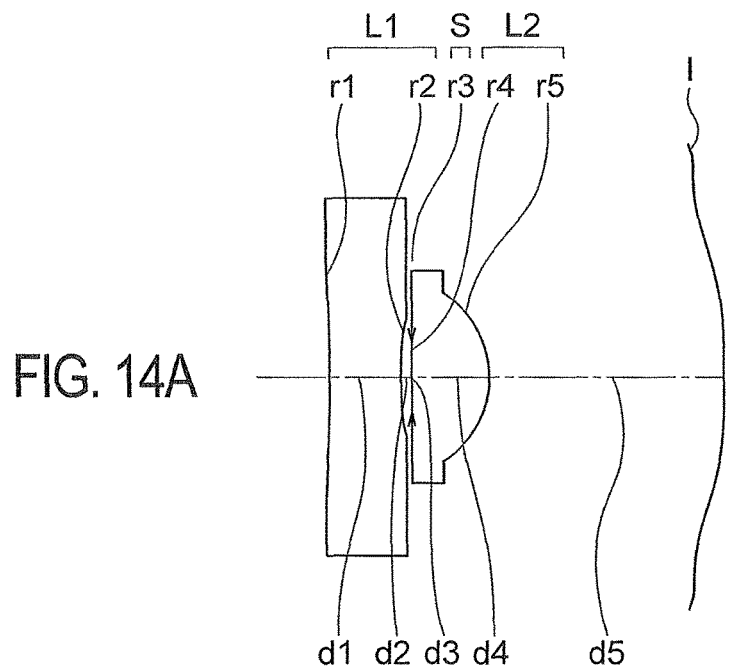
FIG. 14A is a cross-sectional view of an image forming optical system according to an example 10.
Figures 14B, 14C, 14D, 14E:
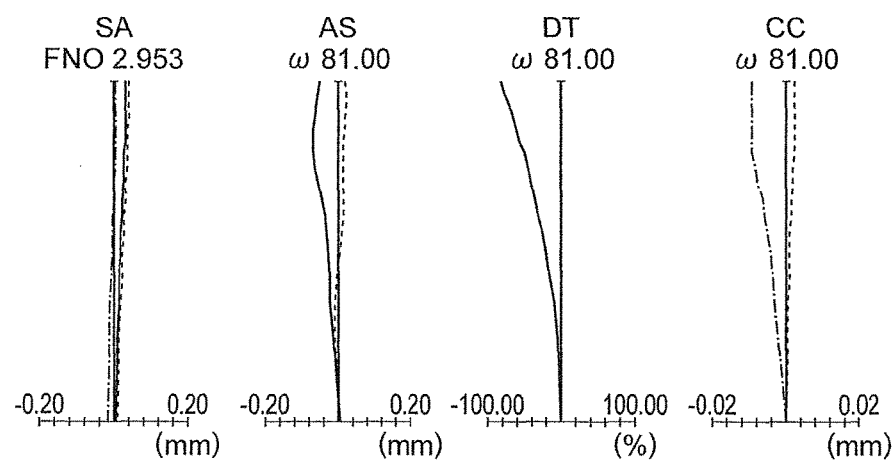
FIG. 14B, FIG. 14C, FIG. 14D, and FIG. 14E are aberration diagrams according to the example 10.
Figure 15A:
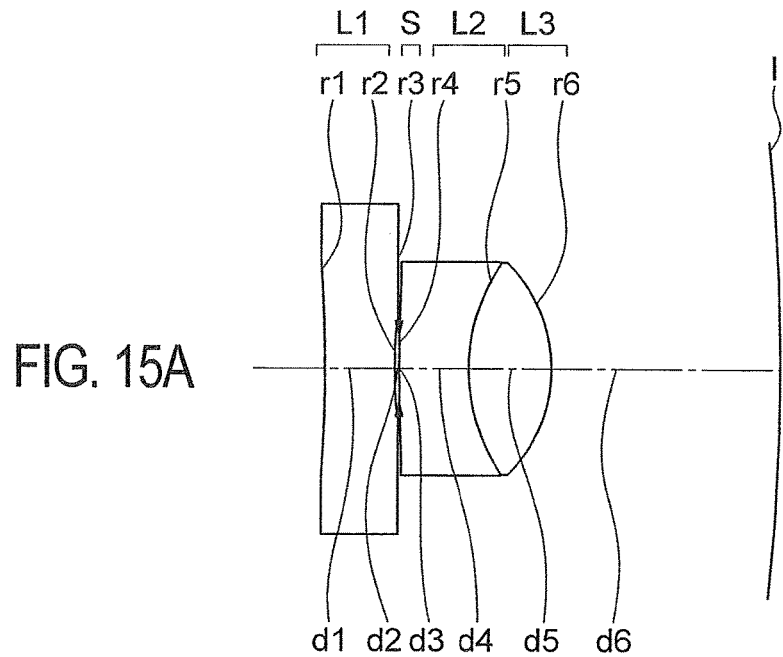
FIG. 15A is a cross-sectional view of an image forming optical system according to an example 11.
Figures 15B, 15C, 15D, 15E:
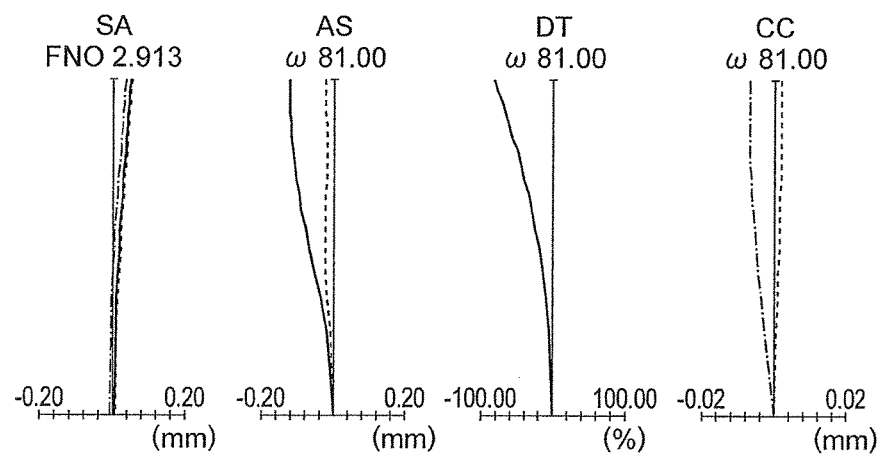
FIG. 15B, FIG. 15C, FIG. 15D, and FIG. 15E are aberration diagrams according to the example 11.
Figure 17A:
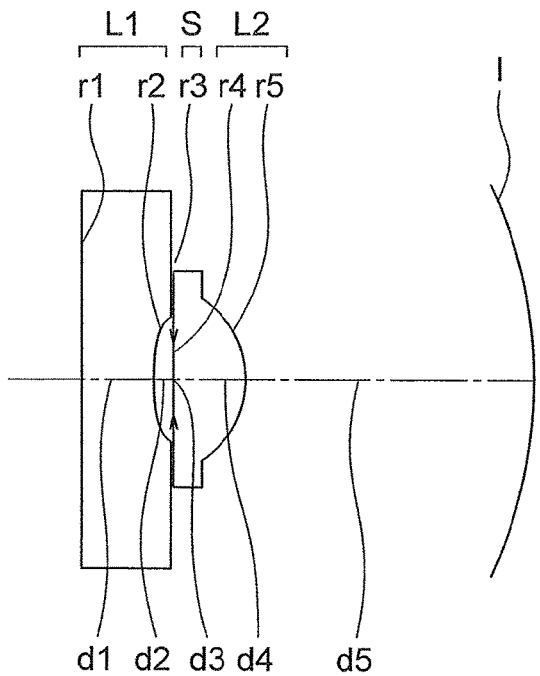
FIG. 17A is a cross-sectional view of an image forming optical system according to an example 13.
Figures 17B, 17C, 17D, 17E:
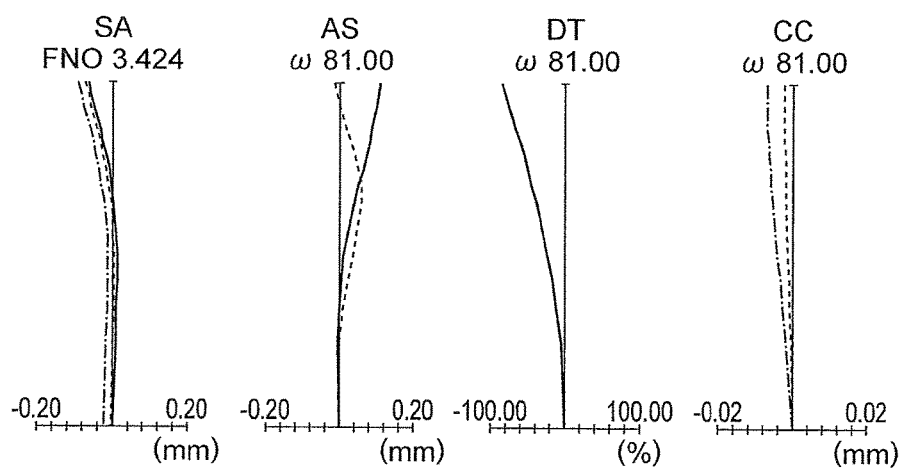
FIG. 17B, FIG. 17C, FIG. 17D, and FIG. 17E are aberration diagrams according to the example 13.
Figure 18A:
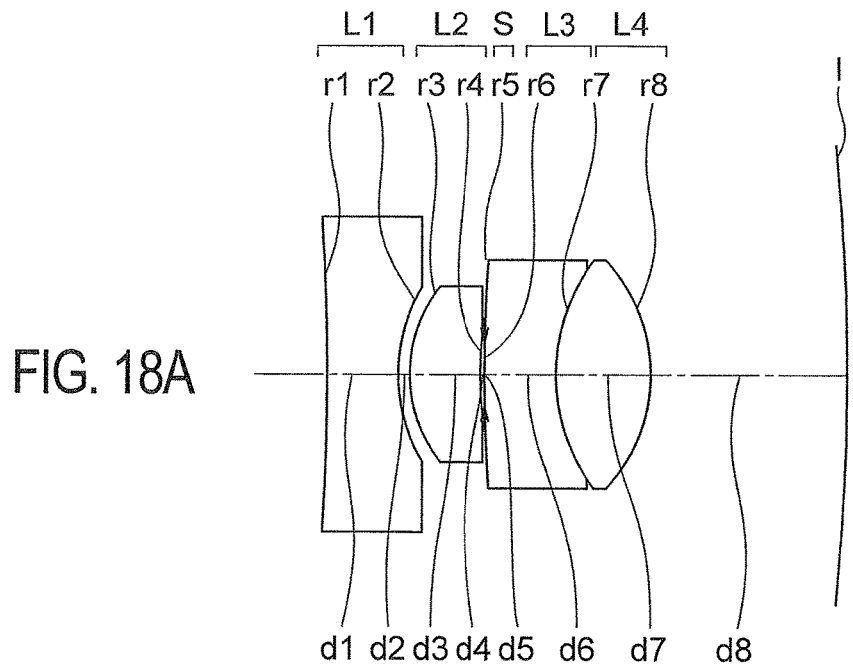
FIG. 18A is a cross-sectional view of an image forming optical system according to an example 14.
Figures 18B, 18C, 18D, 18E:
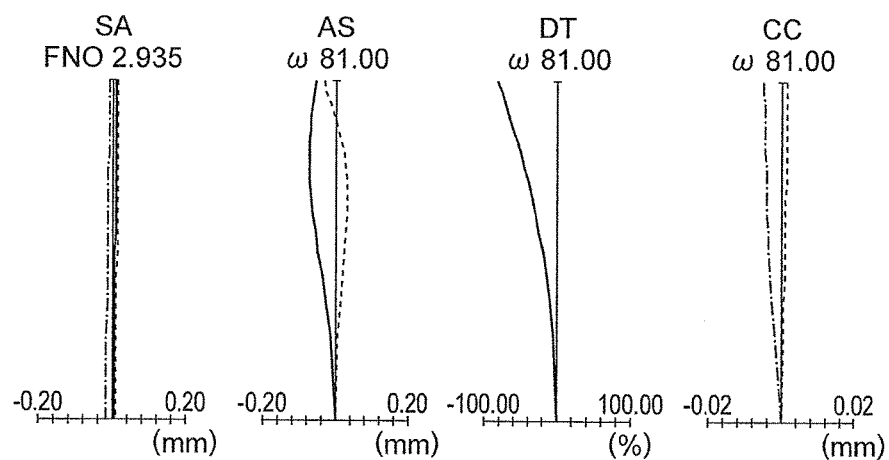
FIG. 18B, FIG. 18C, FIG. 18D, and FIG. 18E are aberration diagrams according to the example 14.

Each conditional expression will be described below. FIG. 4 is a diagram illustrating parameters used in the conditional expressions (B1), (B2), (B3), and (B4).

The conditional expression (B1) regulates a relationship between the paraxial radius of curvature of the object-side optical surface and the paraxial radius of curvature of the image-side optical surface.

As shown in FIG. 4, an object-side optical surface S1 is an optical surface positioned nearest to the object, of optical surfaces which forms the image forming optical system. An image-side optical surface $S_e$ is an optical surface positioned nearest to the image in the image forming optical system. Moreover, $R_1$ is a paraxial radius of curvature of the object-side optical surface $S_1$, and $R_e$ is a paraxial radius of curvature of the image-side optical system $S_e$.

By satisfying the conditional expression (B1), it is possible to make the paraxial radius of curvature of the object-side optical surface larger than the paraxial radius of curvature of the image-side optical surface. In other words, the paraxial radius of curvature of the object-side optical surface $S_1$ becomes larger than the paraxial radius of curvature of the image-side optical surface $S_e$. Accordingly, it is possible to correct the astigmatism favorably while securing a wide angle of view.

When exceeding an upper limit value of the conditional expression (B1), either correction of the astigmatism becomes difficult or widening of the angle of view becomes difficult.

It is preferable that the following conditional expression (B1-1) is satisfied instead of the conditional expression (B1).

$$0 \le |R_e/R_1| < 0.6 \qquad (B1\text{-}1)$$

Moreover, it is more preferable that the following conditional expression (B1-2) is satisfied instead of the conditional expression (B1).

$$0 \le |R_e/R_1| < 0.45 \qquad (B1\text{-}2)$$

The conditional expression (B2) regulates a shape of the image-side optical surface.

By satisfying the conditional expression (B2), it is possible to make the shape of the image-side optical surface convex toward the image side. In other words, the image-side optical surface $S_e$ assumes a shape having convex surface directed toward the image side. Accordingly, it is possible to correct the astigmatism favorably.

When exceeding an upper limit value of the conditional expression (B2), the shape of the image-side optical surface becomes a flat shape or a shape having a convex surface directed toward the image side. AS a result, favorable correction of the astigmatism becomes difficult.

The Conditional expression (B3) regulates a position of the exit pupil. The position of the exit pupil regulated by conditional expression (B3) is a position of the exit pupil by a light ray incident on the image forming optical system at an angle of 60 degrees.

As shown in FIG. 4, a light ray $L_{60}$ is incident on the image forming optical system at an angle of 60 degrees. Therefore, $EXP_{60}$ indicates a position of the exit pupil by the light ray $L_{60}$. More specifically, $EXP_{60}$ is a distance on the optical axis from an image I up to the exit pupil. When the exit pupil positions on the image forming optical system side of the image I, $EXP_{60}$ is negative, and when the exit pupil positions on the opposite side, $EXP_{60}$ is positive.

By satisfying the conditional expression (B3), even when the angle of view is wide, it is possible to suppress occurrence of the astigmatism in a peripheral portion of the image.

When exceeding an upper limit value of conditional expression (B3), a light ray height at the object-side optical surface becomes high. In this case, the astigmatism being substantial, the imaging performance is worsened.

It is preferable that the following conditional expression (B3-1) is satisfied instead of the conditional expression (B3).

$$-10 < EXP_{60}/f < -0.5 \qquad (B3\text{-}1)$$

When exceeding an upper limit value of the conditional expression (B3-1), the exit-pupil position approaches closer to the image plane. Consequently, shading is susceptible to occur.

When falling below a lower limit value of the conditional expression (B3-1), the exit-pupil position goes away from the image plane. This is disadvantageous for small-sizing of the optical system.

It is preferable that the following conditional expression (B3-2) is satisfied instead of the conditional expression (B3-2).

$$-2.2 < EXP_{60}/f < 1.3 \qquad (B3\text{-}2)$$

The conditional expression (B4) regulates the maximum height of a light ray in a predetermined area. The predetermined area is an area on the object-side optical surface through which the effective light beam passes.

As shown in FIG. 4, $Y_1$ denotes a distance from the optical axis AX up to a passing position at which a light ray passes through a position at the maximum height, from among light rays passing through the optical surface $S_1$.

By satisfying the conditional expression (B4), it is possible to make the optical system small-sized.

When exceeding an upper limit value of the conditional expression (B4), since a diameter of the object-side optical surface becomes large, small-sizing of the optical system becomes difficult.

It is preferable that the following conditional expression (B4-1) is satisfied instead of the conditional expression (B4).

$$0.1 < Y_1 \times 2/f < 2 \qquad (B4\text{-}1)$$

Moreover, it is more preferable that the following conditional expression (B4-2) is satisfied instead of the conditional expression (B4).

$$0.2 < Y_1 \times 2/f < 2 \qquad (B4\text{-}2)$$

In the image forming optical system according to the present embodiment, it is preferable that the following conditional expression (B5) is satisfied:

$$L_{1e}'/TL' \le 0.65 \qquad (B5),$$

where, $L_{1e}'$ denotes a distance on the optical axis from the object-side optical surface up to the image-side optical surface, and $TL'$ denotes the distance on the optical axis from the object-side optical surface up to the image.

By satisfying the conditional expression (B5), a back focus can be secured adequately while maintaining the high imaging performance.

When exceeding an upper limit value of the conditional expression (B5), correction of an aberration becomes easy, but it becomes difficult to secure adequately the back focus.

It is preferable that the following conditional expression (B5-1) is satisfied instead of the conditional expression (B5).

$$0.25 < L_{1e}'/TL' \le 0.5 \qquad (B5\text{-}1)$$

Technical significance of the upper limit value of the conditional expression (B5-1) is same as the technical significance of the conditional expression (B5).

By making so as not to exceed the upper limit value of the conditional expressions (B5) and (B5-1), it becomes easy to secure the back focus, and to realize small-sizing and weight-reduction of the image forming optical system with respect to a size of the image plane.

By making so as not fall below a lower limit value of the conditional expressions (B5) and (B5-1), it becomes easy to secure adequate distance on the optical axis from the object-side optical surface up to the image-side optical surface, and it is advantageous for correction of aberration and for securing a favorable imaging performance.

When falling below a lower limit value of the conditional expression (B5-1), the distance on the optical axis from the object-side optical surface up to the image-side optical surface becomes small. In this case, since aberration correction cannot be carried out adequately, a favorable imaging performance cannot be achieved.

For the conditional expression (B5), it is preferable to let the upper limit value to be 0.63, and more preferably to be 0.5. For the conditional expressions (B5-1), it is preferable to let the lower limit value to be 0.36.

In the image forming optical system according to the present embodiment, it is preferable that the object-side optical surface is an aspheric surface.

As described above, in the image pickup apparatus according to the present embodiment, the curved image is formed. The curved image is picked up by the image pickup element, for instance. When an amount of curvature of the curved image is large, an amount of curvature of the image pickup surface of the image pickup element also becomes large. Since there is a limit for the amount of curvature of the image pickup surface while manufacturing, it is preferable to let the amount of curvature of the curved image to be an appropriate amount.

Moreover, in the curved image, it is preferable that an aberration is corrected favorably.

Consequently, the image forming optical system is sought to have an appropriate amount of curvature of field that occurs, while having a wide angle of view, and also to form the curved image in which an aberration other than the curvature of field is corrected favorably. Therefore, by letting the object-side optical surface to be an aspheric surface, it is advantageous for forming a wide-angle curved image in which the amount of the curvature of field that occurs is appropriate, and in which an aberration other than the curvature of field has been corrected favorably.

In the image forming optical system according to the present embodiment, the object-side optical surface may be let to have a shape having a concave surface directed toward the object side. By making such arrangement, it is possible to widen the angle of view.

In the image forming optical system according to the present embodiment, a peripheral portion of the object-side optical surface may be let to have a shape having a concave surface directed toward the object side. By making such arrangement, it is possible to further widen the angle of view.

In the image forming optical system according to the present embodiment, it is preferable that the following conditional expression (B6) is satisfied:

$$0<|R_e/R_{img}'|\leq 2.0 \tag{B6}$$

where, $R_e$ denotes the paraxial radius of curvature of the image-side optical surface, and $R_{img}'$ denotes a minimum value of a radius of curvature of a virtual spherical surface which includes an apex and a point at which a light ray incident on the image forming optical system at a half angle of view of 60 degrees intersects the image, letting a point of intersection of the optical axis and the image to be the apex.

Figure 23:
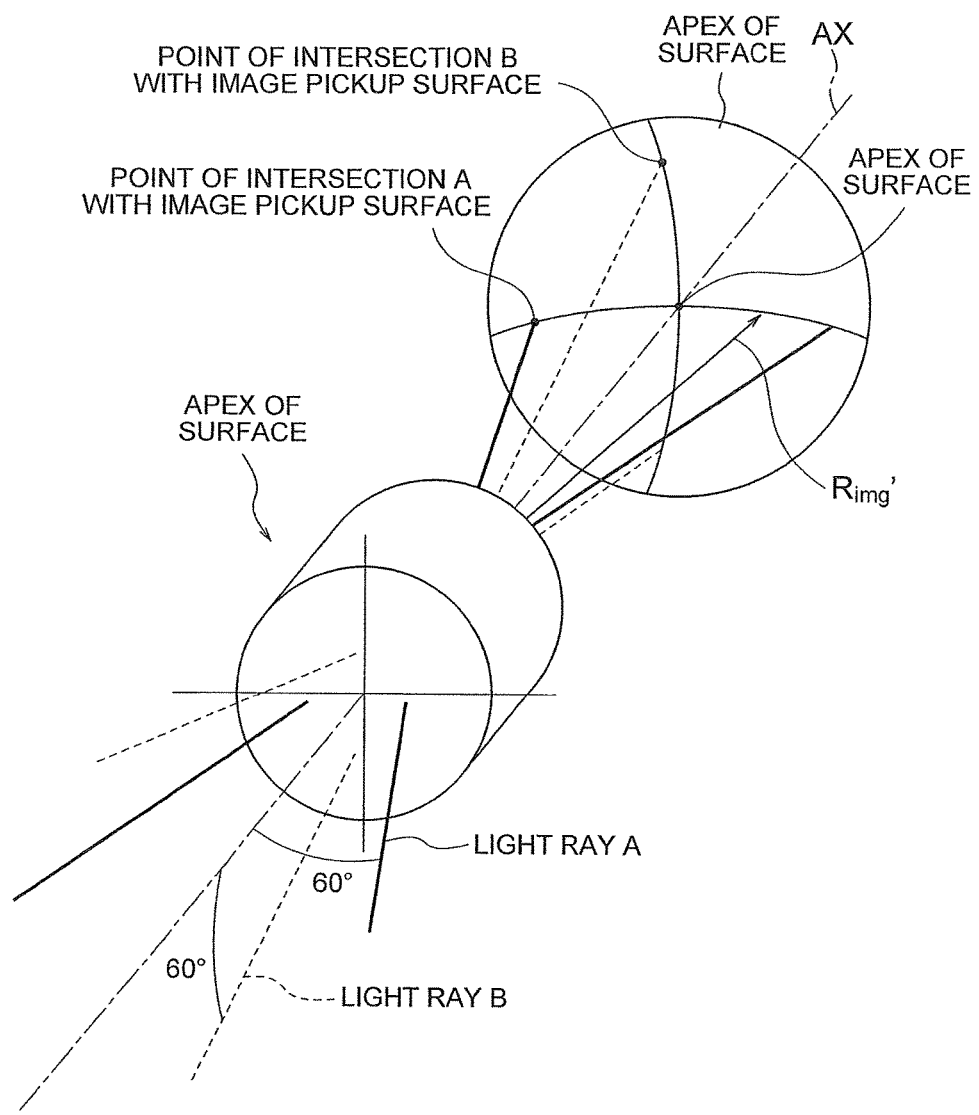
FIG. 23 is still another diagram illustrating parameters used in conditional expressions.

FIG. 23 is a diagram illustrating a parameter $R_{img}'$. The image pickup surface is disposed at an image position for example. Therefore, the description will be made by substituting the image by the image pickup surface. When the image pickup surface has a curved shape that is rotationally symmetrical about an axis, a value of the radius of curvature of the virtual spherical surface is same irrespective of a direction of the angle of view (for example, in a vertical direction shown in a light ray B and a horizontal direction shown in a light ray A of the paper surface). Moreover, when the image pickup surface has a shape such as a cylindrical shape, a toric shape, or a shape formed by joining a plurality of flat surfaces, since the value of the radius of curvature of the virtual spherical surface varies according to the direction of the angle of view, the radius of curvature of the virtual surface is let to be a value that is the minimum of a value that may be assumed in that case.

The conditional expression (B6) regulates a relationship between the paraxial radius of curvature of the image-side optical surface and the abovementioned $R_{img}'$.

By making so as not to exceed an upper limit value of the conditional expression (B6), it becomes easy to make the paraxial radius of curvature of the image-side optical surface small with respect to the image pickup surface, and thereby it is preferable to correct the astigmatism.

When falling below a lower limit value of the conditional expression (B6), since the image pickup surface becomes a flat surface, correction of the curvature of field with a small number of lens components becomes difficult.

For the conditional expression (B6), it is preferable to let the lower limit value to be 0.1, and more preferably to be 0.2. For the conditional expression (B6), it is preferable to let the upper limit value to be 1.5, and more preferably to be 1.0.

In the image forming optical system according to the present embodiment, it is preferable that the following conditional expression (B7) is satisfied:

$$SAG_{11}'/f \leq 0 \tag{B7}$$

where, $SAG_{11}'$ denotes a distance in a direction along the optical axis, from an apex of the object-side optical surface up to a point in which a most peripheral effective light ray incident at a maximum image height on the image forming optical system passes through the object-side optical surface, letting a direction in which a light ray travels to be a positive direction, and f denotes the focal length of the image forming optical system.

Figure 24:
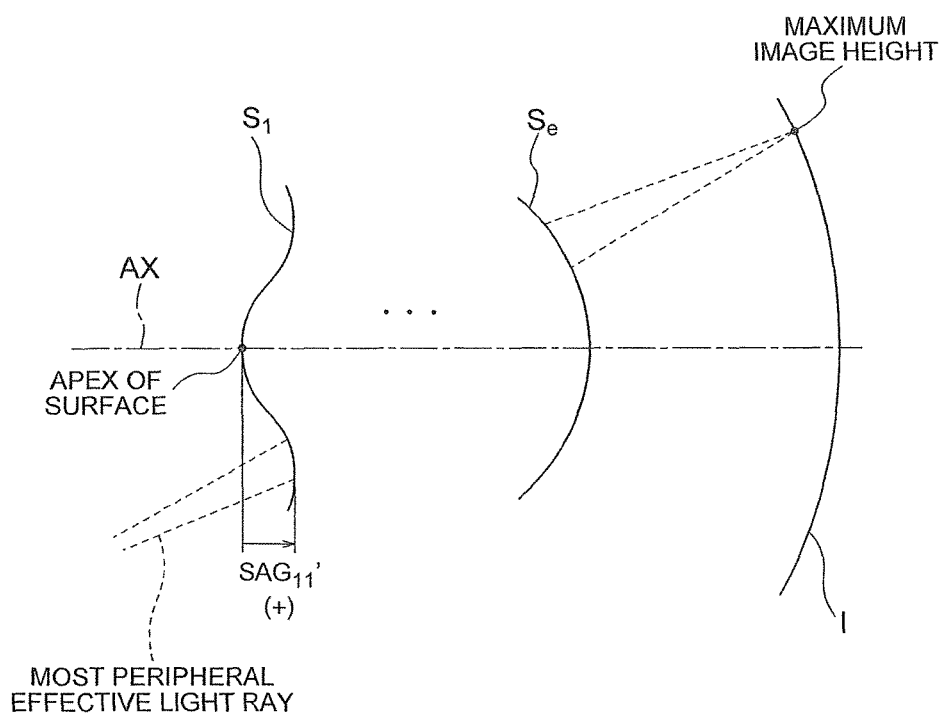
FIG. 24 is still another diagram illustrating parameters used in conditional expressions.

FIG. 24 is a diagram illustrating a parameter $SAG_{11}'$. $SAG_{11}'$ is a distance on an object-side optical surface $S_1$, in the direction along the optical axis AX, from an apex of a surface up to a point in which the a peripheral effective light ray incident at a maximum image height on the image forming optical system passes through the object-side optical surface $S_1$. Here, direction in which a light ray travels is let to be a positive direction.

By satisfying the conditional expression (B7), it is possible to achieve widening of the angle of view while maintaining the amount of curvature of field to be appropriate.

By making so as not to exceed an upper limit value of conditional expression (B7), it becomes easy to secure a negative refractive power entirely or partially on the object-side optical surface, and it is advantageous for securing a wide angle of view.

It is preferable that the following conditional expression (B7-1) is satisfied instead of the conditional expression (B7).

$$-0.03 < SAG_{11}'/f < 0 \tag{B7-1}$$

By making so as not to fall below a lower limit value of the conditional expression (B7-1), it is advantageous for reducing an off-axis aberration and an effect of an assembly error.

It is preferable to let the lower limit value of the conditional expression (B7-1) to be −0.02, and more preferably to be −0.015. Moreover, it is preferable to let the upper limit value of the conditional expressions (B7) and (B7-1) to be −0.0005, and more preferably to be −0.001.

It is preferable that the image forming optical system according to the present embodiment includes an aperture stop which limits an axial light beam, and the following conditional expression (5) is satisfied:

$$PS \times EXP < -0.7 \quad (5),$$

where,

PS denotes Petzval's sum for the image forming optical system, and here

Petzval's sum PS is expressed by the following expression:

$$PS = \sum_{i=1}^{k} \frac{1}{n_i \times f_i}$$

where, i denotes a order of lenses from the object side in the image forming optical system, k denotes total number of lenses in the image forming optical system, $n_i$ denotes a refractive index for a d-line of an $i^{th}$ lens, $f_i$ denotes a focal length of the $i^{th}$ lens, and EXP denotes a distance along the optical axis from the image up to a paraxial exit pupil position of the image forming optical system, and is let to be negative when the paraxial exit pupil is on the object side of the image.

The conditional expression (5-1) may be satisfied. The technical significance of the conditional expressions (5) and (5-1) are as mentioned above.

In the image forming optical system according to the present embodiment, it is preferable that the following conditional expression (B9) is satisfied:

$$PS_{inv}/R_1 \leq 0 \quad (B9),$$

where, $R_1$ denotes the paraxial radius of curvature of the object-side optical surface, and $PS_{inv}$ denotes an inverse number of Petzval's sum for the image forming optical system, and here Petzval's sum PS is expressed by the following expression:

$$PS = \sum_{i=1}^{k} \frac{1}{n_i \times f_i}$$

where, i denotes an order from the object side of lenses in the image forming optical system, k denotes total number of lenses in the image forming optical system, $n_i$ denotes a refractive index for a d-line of an $i^{th}$ lens, and $f_i$ denotes the focal length of the $i^{th}$ lens.

By satisfying conditional expression (B9), it is advantageous for achieving favorable imaging performance along the image pickup surface curved to be concave toward the object side, while securing the angle of view and maintaining the amount of the curvature of field to be optimum.

It is preferable that the following conditional expression (B9-1) is satisfied instead of the conditional expression (B9).

$$-2.5 < PS_{inv}/R_1 \leq 0 \quad (B9-1)$$

By making so as not to exceed an upper limit value of the conditional expressions (B9) and (B9-1), it becomes easy to let the object-side optical surface to be either flat or concave in a paraxial region, and it is advantageous for making the back focus long, and the lens portion small-sized. Or, it is advantageous for suppressing curvature of the image pickup surface from becoming excessive, and for reducing a manufacturing cost of the image pickup element.

By making so as not to fall below a lower limit value of the conditional expression (B9-1), it becomes easy to make Petzval's sum large, and it is advantageous for optimizing the amount of curvature of field that occurs.

For the conditional expression (B9-1), it is preferable to let the lower limit value to be −2.0, and more preferably to be −1.5. For the conditional expressions (B9) and (B9-1), it is preferable to let the upper limit value to be −0.1.

It is preferable that the image forming optical system according to the present embodiment includes an aperture stop which limits an axial light beam, and the following conditional expression (B10) is satisfied:

$$(EXP/f)/(\phi_e'/\phi_1') < -1.2 \quad (B10),$$

where,

EXP denotes a distance along the optical axis from the image up to the paraxial exit pupil position of the image forming optical system, and is let to be negative when the paraxial exit pupil position is on the object side of the image, f denotes the focal length of the image forming optical system, $\phi_e'$ denotes a maximum diameter of an area on the surface nearest to the object-side optical surface through which an effective light beam that contributes to image formation at the maximum image height position passes, when measured perpendicularly with respect to an optical axis, and $\phi_1'$ denotes a maximum diameter of an area on the object-side optical surface through which axial light beam of the image forming optical system passes, when measured perpendicularly with respect to an optical axis.

Figure 25:
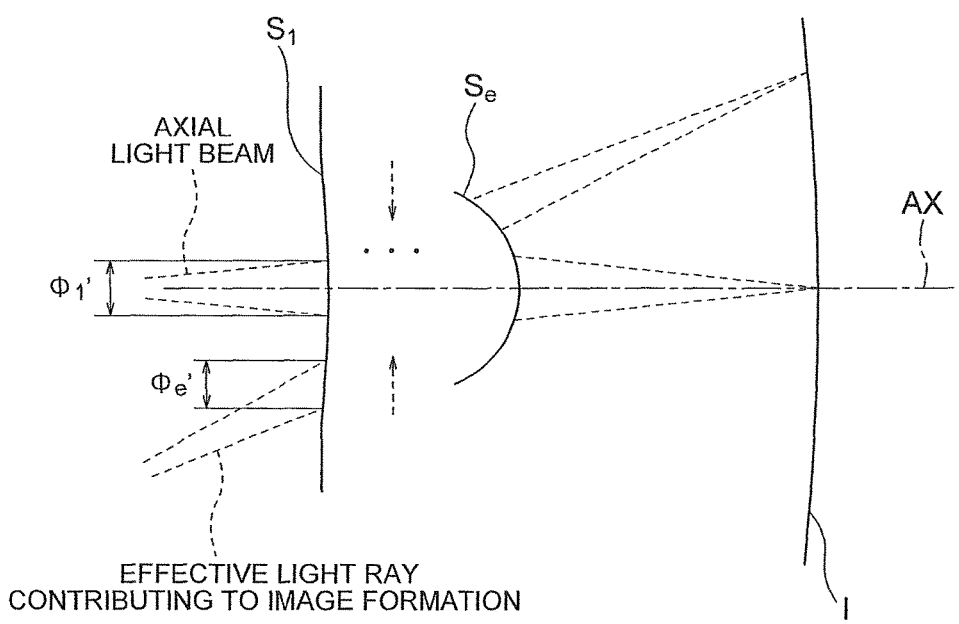
FIG. 25 is still another diagram illustrating parameters used in conditional expressions.

FIG. 25 is a diagram illustrating parameters $\phi_e'$ and $\phi_1'$. Here, $\phi_e'$ denotes the maximum diameter of an area on the object-side surface $S_1$, through which an effective light beam that contributes to image formation at the maximum image height position passes, when measured perpendicularly with respect to the optical axis AX, and $\phi_1'$ denotes the maximum diameter of an area on the object-side optical surface $S_1$ through which an axial light beam of the image forming optical system passes, when measured perpendicularly with respect to the optical axis AX.

Since an occurrence of shading is suppressed by satisfying the conditional expression (B10), it is possible to reduce a change in the amount of light on the optical axis and off the optical axis, and also to make appropriate the angle of incidence of a light ray on the curved image pickup surface.

It is preferable that the following conditional expression (B10-1) is satisfied instead of the conditional expression (B10).

$$-2.5 < (EXP/f)/(\phi_e'/\phi_1') < -1.2 \quad (B10-1)$$

By making so as not to exceed an upper limit value of the conditional expressions (B10) and (B10-1), it becomes easy to make a difference in a beam diameter of axial light and off-axis light small, and it is advantageous for securing peripheral illumination. Or, by making an arrangement such that the exit-pupil position does not become too close to the image pickup surface, it becomes easy to make an angle of incidence of a light ray on the curved image pickup surface small, and to suppress the chromatic shading.

By making so as not to fall below a lower limit value of the conditional expression (B10-1), it becomes easy to prevent the exit-pupil position form becoming too far from the image pickup surface. Accordingly, it becomes easy to suppress the angle of incidence of a light ray on the curved image pickup surface, and to suppress the chromatic shading.

In the lens component of the image forming optical system according to the present embodiment, It is preferable that when a lens component is let to be a lens having only two surfaces that are in contact with air in the effective optical path through which a light beam contributing to the image formation passes, namely, an object-side surface and an image-side surface, the image forming optical system includes in order from the object side to the image side, two lens components namely, an object-side lens component and an image-side lens component.

In such manner, according to the image forming optical system according to the present embodiment, in spite of two lens components, which is a small number, it is possible to achieve a favorable imaging performance along the image pickup surface curved to be concave toward the object side, while securing the optimum angle of view and the optimum amount of the curvature of field.

An optical apparatus according to the present embodiment includes the abovementioned image forming optical system according to the present embodiment, and an image pickup unit having an image pickup surface curved to be concave toward the object side.

By making such arrangement, it is possible to realize an optical system which is capable of capturing a wide range with a high resolution, while being small-sized.

In the image forming optical system according to the present embodiment which forms an image curved to be concave toward an object side, the following conditional expressions (7), (8) and (B3-3) are satisfied:

$$Fno<4 \quad (7),$$

$$0.7<IH/f<1.2 \quad (8), \text{ and}$$

$$EXP_{60}/f<-1 \quad (B3\text{-}3),$$

where,

Fno denotes F number of the image forming optical system,

IH denotes a maximum image height f denotes a focal length of the image forming optical system, and $EXP_{60}$ denotes an exit-pupil position by a light ray incident on the image forming optical system at a half angle of view of 60 degrees.

It is preferable that the following conditional expression (8-1) is satisfied instead of the conditional expression (8).

$$0.9<IH/f<1.15 \quad (8\text{-}1)$$

Examples of an image pickup apparatus will be described below by referring to the accompanying diagrams. However, the present invention is not restricted to the examples described below.

FIG. 5A, FIG. 6A, FIG. 7A, FIG. 8A, FIG. 9A, FIG. 10A, FIG. 11A, FIG. 12A, FIG. 13A, FIG. 14A, FIG. 15A, FIG. 16A, FIG. 17A, FIG. 18A, and FIG. 19A are lens cross-sectional views of image forming optical systems according to examples from example 1 to example 15 (hereinafter, 'the examples 1 to 15') respectively.

FIG. 5B, FIG. 6B, FIG. 7B, FIG. 8B, FIG. 9B, FIG. 10B, FIG. 11B, FIG. 12B, FIG. 13B, FIG. 14B, FIG. 15B, FIG. 16B, FIG. 17B, FIG. 18B, and FIG. 19B show a spherical aberration of the image forming optical systems according to the examples 1 to 15 respectively.

FIG. 5C, FIG. 6C, FIG. 7C, FIG. 8C, FIG. 9C, FIG. 10C, FIG. 11C, FIG. 12C, FIG. 13C, FIG. 14C, FIG. 15C, FIG. 16C, FIG. 17C, FIG. 18C, and FIG. 19C show an astigmatism of the image forming optical systems according to the examples 1 to 15 respectively.

FIG. 5D, FIG. 6D, FIG. 7D, FIG. 8D, FIG. 9D, FIG. 10D, FIG. 11D, FIG. 12D, FIG. 13D, FIG. 14D, FIG. 15D, FIG. 16D, FIG. 17D, FIG. 18D, and FIG. 19D show a distortion of the image forming optical systems according to the examples 1 to 15 respectively.

FIG. 5E, FIG. 6E, FIG. 7E, FIG. 8E, FIG. 9E, FIG. 10E, FIG. 11E, FIG. 12E, FIG. 13E, FIG. 14E, FIG. 15E, FIG. 16E, FIG. 17E, FIG. 18E, and FIG. 19E show a chromatic aberration of magnification of the image forming optical systems according to the examples 1 to 15 respectively.

An image forming optical system according to the example 1 includes in order from an object side, a biconcave negative lens L1 and a planoconvex positive lens L2. An image plane is a spherical plane, and is curved to be concave toward the object side.

An aperture stop S is disposed between the biconcave negative lens L1 and the planoconvex positive lens L2. An aspheric surface is provided to both surfaces of the biconcave negative lens L1.

An image forming optical system according to the example 2 includes in order from an object side, a negative meniscus lens L1 having a convex surface directed toward an image side, and a planoconvex positive lens L2. An image plane is a spherical plane, and is curved to be concave toward the object side.

An aperture stop S is disposed between the negative meniscus lens L1 and the planoconvex positive lens L2. An aspheric surface is provided to both surfaces of the negative meniscus lens L1.

An image forming optical system according to the example 3 includes in order from an object side, a negative meniscus lens L1 having a convex surface directed toward an image side, and a planoconvex positive lens L2. An image plane is a spherical plane, and is curved to be concave toward the object side.

An aperture stop S is disposed between the negative meniscus lens L1 and the planoconvex positive lens L2. An aspheric surface is provided to both surfaces of the negative meniscus lens L1.

An image forming optical system according to the example 4 includes in order from an object side, a biconvex positive lens L1 and a planoconvex positive lens L2. An image plane is a spherical plane, and is curved to be concave toward the object side.

An aperture stop S is disposed between the biconvex positive lens L1 and the planoconvex positive lens L2. An aspheric surface is provided to both surfaces of the biconvex positive lens L1.

An image forming optical system according to the example 5 includes in order from an object side, a biconvex positive lens L1 and a planoconvex positive lens L2. An image plane is a spherical plane, and is curved to be concave toward the object side.

An aperture stop S is disposed between the biconvex positive lens L1 and the planoconvex positive lens L2. An aspheric surface is provided to both surfaces of the biconvex positive lens L1.

An image forming optical system according to the example 6 includes in order from an object side, a negative meniscus lens L1 having a convex surface directed toward an image side and a biconvex positive lens L2. An image plane is a spherical plane, and is curved to be concave toward the object side.

An aperture stop S is disposed at a same position as of an apex of the negative meniscus lens L1. An aspheric surface is provided to both surfaces of the negative meniscus lens L1. The aperture stop S may be disposed on the object side of the negative meniscus lens L1.

An image forming optical system according to the example 7 includes in order from an object side, a negative meniscus lens L1 having a convex surface directed toward an image side, and a positive meniscus lens L2 having a convex surface directed toward the image side. An image plane is a spherical plane, and is curved to be concave toward the object side.

An aperture stop S is disposed at a same position as of an apex of the negative meniscus lens L1. An aspheric surface is provided to both surfaces of the negative meniscus lens L1. The aperture stop S may be disposed on the object side of the negative meniscus lens L1.

An image forming optical system according to the example 8 includes in order from an object side, a positive meniscus lens L1 having a convex surface directed toward an image side, and a biconvex positive lens L2. An image plane is a spherical plane, and is curved to be concave toward the object side.

An aperture stop S is disposed at a same position as of an apex of the positive meniscus lens L1. An aspheric surface is provided to both surfaces of the positive meniscus lens L1. The aperture stop S may be disposed on the object side of the positive meniscus lens L1.

An image forming optical system according to the example 9 includes in order from an object side, a positive meniscus lens L1 having a convex surface directed toward an image side, and a planoconvex positive lens L2. An image plane is a spherical plane, and is curved to be concave toward the object side.

An aperture stop S is disposed at a same position as of an apex of the positive meniscus lens L1. An aspheric surface is provided to both surfaces of the positive meniscus lens L1. The aperture stop S may be disposed on the object side of the positive meniscus lens L1.

An image forming optical system according to the example 10 includes in order from an object side, a biconcave negative lens L1 and a planoconvex positive lens L2. An image plane is a spherical plane, and is curved to be concave toward the object side.

An aperture stop S is disposed between the biconcave negative lens L1 and the planoconvex positive lens L2. An aspheric surface is provided to both surfaces of the biconcave negative lens L1.

An image forming optical system according to the example 11 includes in order from an object side, a biconcave negative lens L1, a negative meniscus lens L2 having a convex surface directed toward the object side, and a biconvex positive lens L3. Here, the negative meniscus lens L2 and the biconvex positive lens L3 are cemented. An image plane is a spherical plane, and is curved to be concave toward the object side.

An aperture stop S is disposed between the biconcave negative lens L1 and the negative meniscus lens L2. An aspheric surface is provided to both surfaces of the biconcave negative lens L1.

An image forming optical system according to the example 12 includes in order from an object side, a biconcave negative lens L1, a positive meniscus lens L2 having a convex surface directed toward the object side, a negative meniscus lens L3 having a convex surface directed toward the object side, and a biconvex positive lens L4. Here, the biconcave negative lens L1 and the positive meniscus lens L2 are cemented. Moreover, the negative meniscus lens L3 and the biconvex positive lens L4 are cemented. An image plane is a spherical plane, and is curved to be concave toward the object side.

An aperture stop S is disposed between the positive meniscus lens L2 and the negative meniscus lens L3. An aspheric surface is provided to an object-side surface of the negative meniscus lens L1 and an image-side surface of the positive meniscus lens L2.

An image forming optical system according to the example 13 includes in order from an object side, a planoconcave negative lens L1 and a planoconvex positive lens L2. An image plane is a spherical plane, and is curved to be concave toward the object side.

An aperture stop S is disposed between the planoconcave negative lens L1 and the planoconvex positive lens L2. An aspheric surface is provided to an image-side surface of the planoconcave negative lens L1 and an image-side surface of the planoconvex positive lens L2.

An image forming optical system according to the example 14 includes in order from an object side, a biconcave negative lens L1, a positive meniscus lens L2 having a convex surface directed toward the object side, a negative meniscus lens L3 having a convex surface directed toward the object side, and a biconvex positive lens L4. Here, the negative meniscus lens L3 and the biconvex positive lens L4 are cemented. An image plane is a spherical plane, and is curved to be concave toward the object side.

An aperture stop S is disposed between the positive meniscus lens L2 and the negative meniscus lens L3. An aspheric surface is provided to an object-side surface of the biconcave negative lens L1 and an image-side surface of the positive meniscus lens L2.

An image forming optical system according to the example 15 includes in order from an object side, a planoconcave negative lens L1 and a planoconvex positive lens L2. Here, the planoconcave negative lens L1 and the planoconvex positive lens L2 are cemented. An image plane is a spherical plane, and is curved to be concave toward the object side.

An aperture stop S is disposed between the planoconcave negative lens L1 and the planoconvex positive lens L2. An aspheric surface is provided to an object-side surface of the planoconcave negative lens L1 and an image-side surface of the planoconvex positive lens L2.

Figure 20:
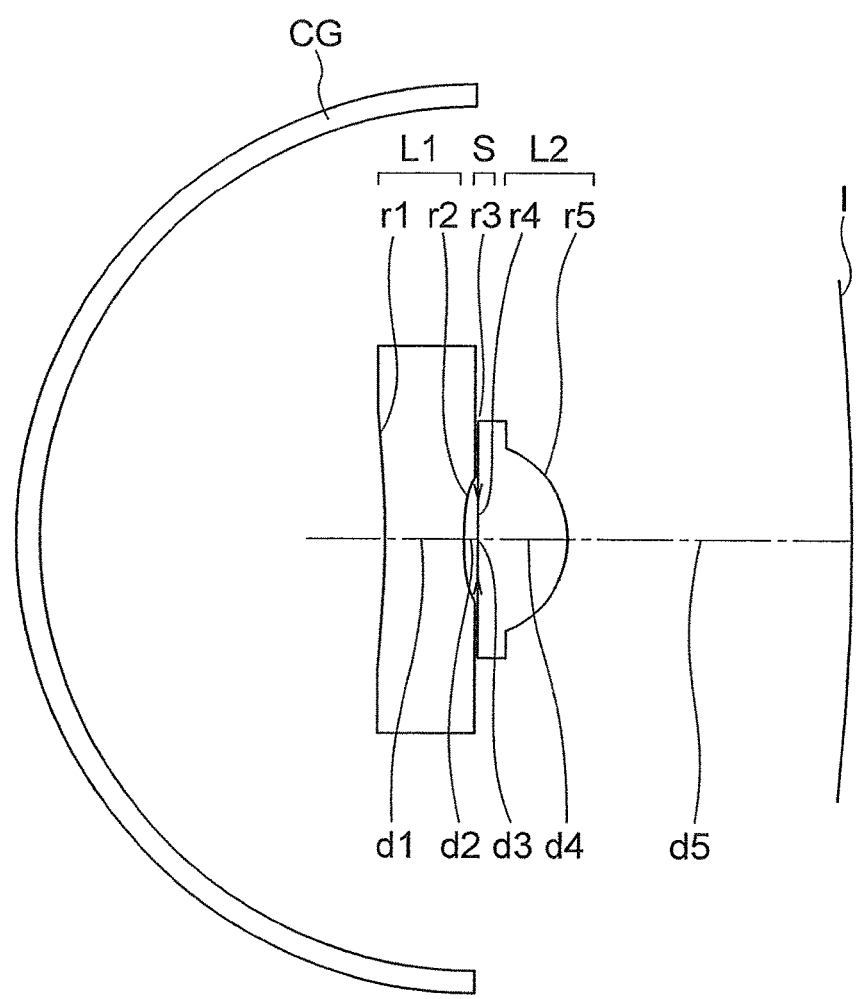
FIG. 20 is a cross-sectional view of an image forming optical system according to an example 16.

An image forming optical system according to an example 16, as shown in FIG. 20, includes in order from an object side, an optical member CG, a biconcave negative lens L1 and a planoconvex positive lens L2. An image plane is a spherical plane, and is curved to be concave toward the object side. The optical system including the a biconcave negative lens L1, an aperture stop S and the planoconvex positive lens L2 is same as the image forming optical system according to the example 1.

FIG. 20 is a schematic diagram illustrating that the optical member CG can be disposed. Therefore, a size and a position of the optical member CG have not been depicted accurately with respect to sizes and positions of the lenses.

The optical member CG is a member in the form of a plate, and both an object-side surface and an image-side surface thereof are curved surfaces. In FIG. 20, both the object-side surface and the image-side surface being curved surfaces, an overall shape of the optical member CG is hemispherical. In the present example, a thickness of the optical member CG, or in other words, a distance between the object-side surface and the image-side surface, is constant toward a curvature center.

A material that allows light to transmit through has been used for the optical member CG. Consequently, light from an object passes through the optical member CG and is incident on the biconcave negative lens L1. The optical member CG is disposed such that a curvature center of the image-side surface substantially coincides with a position of an entrance pupil. Consequently, a new aberration due to the optical member CG hardly occurs. In other words, an imaging performance of the image forming optical system according to the example 16 is not different from an imaging performance of the image forming optical system according to the example 1.

The optical member CG functions as a cover glass. In this case, the optical member CG corresponds to an observation window provided at an outer covering of a capsule endoscope. Therefore, the image forming optical system according to the example 16 can be used for an optical system of a capsule endoscope. The image forming optical system according to the example 2 to the example 15 can also be used for an optical system of an endoscope.

Numerical data of each example described above is shown below. In Surface data, r denotes radius of curvature of each lens surface, d denotes a distance between respective lens surfaces, nd denotes a refractive index of each lens for a d-line, vd denotes an Abbe number for each lens and * denotes an aspheric surface, stop denotes an aperture stop.

Further, in Various data, f denotes a focal length of the entire system, FNO. denotes an F number, ω denotes a half angle of view, IH denotes an image height, LTL denotes a lens total length of the optical system, BF denotes a back focus. Further, back focus is a unit which is expressed upon air conversion of a distance from a rearmost lens surface to a paraxial image surface. The lens total length is a distance from a frontmost lens surface to the rearmost lens surface plus back focus. Moreover, f1, f2, f3 and f4 denote a focal length of each lens. A unit of the half angle of view is degree.

A shape of an aspheric surface is defined by the following expression where the direction of the optical axis is represented by z, the direction orthogonal to the optical axis is represented by y, a conical coefficient is represented by K, aspheric surface coefficients are represented by A4, A6, A8, A10, A12 . . .

$$Z=(y^2/r)/[1+\{1-(1+k)(y/r)^2\}^{1/2}]+A4y^4+A6y^6+A8y^8+A10y^{10}+A12y^{12}+\ldots$$

Further, in the aspherical surface coefficients, 'e-n' (where, n is an integral number) indicates '$10^{-n}$'. Moreover, these symbols are commonly used in the following numerical data for each example.

Example 1

| Unit mm | | | | |
|---|---|---|---|---|
| Surface data | | | | |
| Surface no. | r | d | nd | vd |
| Object plane | ∞ | 10.10 | | |
| 1* | −3.185 | 0.30 | 1.53110 | 56.00 |
| 2* | 1.738 | 0.05 | | |
| 3(Stop) | ∞ | 0.00 | | |
| 4 | ∞ | 0.34 | 1.53110 | 56.00 |
| 5 | −0.375 | 1.07 | | |
| Image plane | −9.568 | | | |

| Unit mm |
|---|
| Aspherical surface data |
| 1st surface |
| k = 0.000 |
| A4 = 2.53231e−02, A6 = 2.07188e+00, A8 = −5.74113e+00 |
| 2nd surface |
| k = 0.000 |
| A4 = 7.56464e+00 |

| Various data | |
|---|---|
| f | 0.855 |
| FNO. | 3.047 |
| 2ω | −164 |
| IH | 0.975 |
| LTL | 1.760 |
| BF | 1.07 |
| f1 | −2.065 |
| f2 | 0.704 |

Example 2

| Unit mm | | | | |
|---|---|---|---|---|
| Surface data | | | | |
| Surface no. | r | d | nd | vd |
| Object plane | ∞ | 10.10 | | |
| 1* | −4.280 | 0.47 | 1.53110 | 56.00 |
| 2* | −6.524 | 0.06 | | |
| 3(Stop) | ∞ | 0.00 | | |
| 4 | ∞ | 0.37 | 1.53110 | 56.00 |
| 5 | −0.512 | 1.09 | | |
| Image plane | −2.437 | | | |

| Aspherical surface data |
|---|
| 1st surface |
| k = 0.000 |
| A4 = −3.36755e−01, A6 = 1.43642e+00, A8 = −1.68203e+00 |
| 2nd surface |
| k = 0.000 |
| A4 = 2.37328e+00 |

| Various data | |
|---|---|
| f | 0.949 |
| FNO. | 3.330 |
| 2ω | −164 |
| IH | 0.975 |
| LTL | 1.982 |
| BF | 1.09 |
| f1 | −25.152 |
| f2 | 0.960 |

Example 3

| Unit ram | | | | |
|---|---|---|---|---|
| Surface data | | | | |
| Surface no. | r | d | nd | vd |
| Object plane | ∞ | 10.10 | | |
| 1* | −3.773 | 0.30 | 1.53110 | 56.00 |
| 2* | −5.549 | 0.03 | | |
| 3(Stop) | ∞ | 0.00 | | |

-continued

Unit mm

| | | | | |
|---|---|---|---|---|
| 4 | ∞ | 0.46 | 1.53110 | 56.00 |
| 5 | −0.527 | 1.13 | | |
| Image plane | −1.507 | | | |

Aspherical surface data

1st surface k = 0.000
A4 = −8.23828e−02, A6 = 1.38064e+00, A8 = −2.37738e+00

2nd surface k = 0.000
A4 = 1.78525e+00

Various data

| | |
|---|---|
| f | 0.988 |
| FNO. | 3.405 |
| 2ω | −162 |
| IH | 0.975 |
| LTL | 1.929 |
| BF | 1.13 |
| f1 | −23.496 |
| f2 | 0.988 |

Example 4

Unit mm

Surface data

| Surface no. | r | d | nd | vd |
|---|---|---|---|---|
| Object plane | ∞ | 10.10 | | |
| 1* | 83.990 | 0.50 | 1.53110 | 56.00 |
| 2* | −3.320 | 0.06 | | |
| 3(Stop) | ∞ | 0.00 | | |
| 4 | ∞ | 0.36 | 1.53110 | 56.00 |
| 5 | −0.570 | 0.99 | | |
| Image plane | −1.952 | | | |

Aspherical surface data

1st surface k = 0.000
A4 = −5.60219e−01, A6 = 1.37170e+00, A8 = −1.12862e+00

2nd surface k = 0.000
A4 = 1.58678e+00

Various data

| | |
|---|---|
| f | 0.948 |
| FNO. | 3.167 |
| 2ω | −163 |
| IH | 0.975 |
| LTL | 1.902 |
| BF | 0.99 |
| f1 | 6.000 |
| f2 | 1.069 |

Example 5

Unit mm

Surface data

| Surface no. | r | d | nd | vd |
|---|---|---|---|---|
| Object plane | ∞ | 10.10 | | |
| 1* | −8.422 | 0.49 | 1.53110 | 56.00 |
| 2* | −1.934 | 0.05 | | |
| 3(Stop) | ∞ | 0.00 | | |
| 4 | ∞ | 0.42 | 1.53110 | 56.00 |
| 5 | −0.690 | 0.97 | | |
| Image plane | −1.506 | | | |

Aspherical surface data

1st surface k = 0.000
A4 = −6.27531e−01, A6 = 1.03387e+00, A8 = −5.88990e−01

2nd surface k = 0.000
A4 = 5.30326e−01

Various data

| | |
|---|---|
| f | 0.993 |
| FNO. | 3.224 |
| 2ω | −162 |
| IH | 0.975 |
| LTL | 1.931 |
| BF | 0.97 |
| f1 | 2.998 |
| f2 | 1.294 |

Example 6

Unit mm

Surface data

| Surface no. | r | d | nd | vd |
|---|---|---|---|---|
| Object plane | ∞ | 10.10 | | |
| 1(Stop) | ∞ | 0.00 | | |
| 2* | −1.471 | 0.30 | 1.63493 | 23.89 |
| 3* | −1.685 | 0.05 | | |
| 4 | 30.637 | 0.30 | 1.77250 | 49.60 |
| 5 | −0.819 | 1.15 | | |
| Image plane | −2.410 | | | |

Aspherical surface data

2nd surface k = 0.000
A4 = −1.52940e+00, A6 = 4.61522e+01, A8 = −2.70647e+03, A10 = 5.28160e+04

3rd surface k = 0.000
A4 = 2.92858e−01, A6 = −1.48191e+01, A8 = 1.78831e+02, A10 = −5.81275e+02

Various data

| | |
|---|---|
| f | 0.974 |
| FNO. | 3.282 |
| 2ω | −160 |
| IH | 0.975 |
| LTL | 1.802 |

-continued

| Unit mm | |
|---|---|
| BF | 1.15 |
| f1 | −39.920 |
| f2 | 1.032 |

Example 7

| Unit mm | | | | |
|---|---|---|---|---|
| Surface data | | | | |
| Surface no. | r | d | nd | vd |
| Object plane | ∞ | 10.10 | | |
| 1(Stop) | ∞ | 0.00 | | |
| 2* | −3.775 | 0.30 | 1.63493 | 23.89 |
| 3* | −4.623 | 0.05 | | |
| 4 | −37.325 | 0.30 | 1.77250 | 49.60 |
| 5 | −0.764 | 1.13 | | |
| Image plane | −1.491 | | | |

Aspherical surface data

2nd surface k = 0.000
A4 = −1.00244e+00, A6 = 3.67646e+01, A8 = −2.55931e+03,
A10 = 4.05208e+04

3rd surface k = 0.000
A4 = 3.76741e−01, A6 = −1.46146e+01, A8 = 1.55644e+02,
A10 = −4.99373e+02

| Various data | |
|---|---|
| f | 0.991 |
| FNO. | 3.340 |
| 2ω | −173 |
| IH | 0.975 |
| LTL | 1.784 |
| BF | 1.13 |
| f1 | −37.207 |
| f2 | 1.001 |

Example 8

| Unit mm | | | | |
|---|---|---|---|---|
| Surface data | | | | |
| Surface no. | r | d | nd | vd |
| Object plane | ∞ | 10.10 | | |
| 1(Stop) | ∞ | 0.00 | | |
| 2* | −2.258 | 0.37 | 1.53110 | 56.00 |
| 3* | −0.864 | 0.05 | | |
| 4 | 4.873 | 0.44 | 1.53110 | 56.00 |
| 5 | −0.981 | 0.98 | | |
| Image plane | −1.946 | | | |

Aspherical surface data

2nd surface k = 0.000
A4 = −7.49745e−01, A6 = 8.48354e+01, A8 = −6.16466e+03,
A10 = 1.26740e+05

-continued

| Unit mm | |
|---|---|

3rd surface k = 0.000
A4 = 6.12011e−01, A6 = −1.00316e+01, A8 = 5.20328e+01,
A10 = −1.02293e+02

| Various data | |
|---|---|
| f | 0.989 |
| FNO. | 3.334 |
| 2ω | −162 |
| IH | 0.975 |
| LTL | 1.831 |
| BF | 0.98 |
| f1 | 2.403 |
| f2 | 1.571 |

Example 9

| Unit mm | | | | |
|---|---|---|---|---|
| Surface data | | | | |
| Surface no. | r | d | nd | vd |
| Object plane | ∞ | 10.10 | | |
| 1(Stop) | ∞ | 0.00 | | |
| 2* | −19.712 | 0.46 | 1.53110 | 56.00 |
| 3* | −0.657 | 0.05 | | |
| 4 | ∞ | 0.30 | 1.53110 | 56.00 |
| 5 | −1.951 | 0.90 | | |
| Image plane | −1.503 | | | |

Aspherical surface data

2nd surface k = 0.000
A4 = −1.69752e+00, A6 = 8.48174e+01, A8 = −4.79152e+03,
A10 = 8.61262e+04

3rd surface k = 0.000
A4 = 1.57455e−01, A6 = −5.33428e+00, A8 = 2.21803e+01,
A10 = −8.34925e+01

| Various data | |
|---|---|
| f | 0.986 |
| FNO. | 3.325 |
| 2ω | −162 |
| IH | 0.975 |
| LTL | 1.714 |
| BF | 0.90 |
| f1 | 1.263 |
| f2 | 3.658 |

Example 10

| Unit mm | | | | |
|---|---|---|---|---|
| Surface data | | | | |
| Surface no. | r | d | nd | vd |
| Object plane | ∞ | 10.10 | | |
| 1* | −6.802 | 0.30 | 1.53110 | 56.00 |
| 2* | 7.707 | 0.05 | | |
| 3(Stop) | ∞ | 0.00 | | |

-continued

Unit mm

| 4 | ∞ | 0.33 | 1.53110 | 56.00 |
| 5 | −0.427 | 0.98 | | |
| Image plane* | −9.807 | | | |

Aspherical surface data

1st surface k = 0.000
A4 = −2.55684e−01, A6 = 2.55471e+00, A8 = −5.39397e+00
2nd surface k = 0.000
A4 = 4.91252e+00
Image plane k = 0.000
A4 = −1.09530e+00, A6 = 1.89310e+00, A8 = −6.95550e−01,
A10 = −2.08580e−01

Various data

| f | 0.856 |
| FNO. | 2.953 |
| 2ω | −163 |
| IH | 0.975 |
| LTL | 1.653 |
| BF | 0.98 |
| f1 | −6.726 |
| f2 | 0.800 |

Example 11

Unit mm

Surface data

| Surface no. | r | d | nd | νd |
| --- | --- | --- | --- | --- |
| Object plane | ∞ | 10.10 | | |
| 1* | −10.000 | 0.30 | 1.53110 | 56.00 |
| 2* | 4.442 | 0.02 | | |
| 3(Stop) | ∞ | 0.00 | | |
| 4 | 8.146 | 0.30 | 1.84666 | 23.78 |
| 5 | 0.806 | 0.35 | 1.80610 | 40.92 |
| 6 | −0.658 | 0.97 | | |
| Image plane | −9.785 | | | |

Aspherical surface data

1st surface k = 0.000
A4 = −5.46945e−01, A6 = 3.59115e+00, A8 = −7.35098e+00
2nd surface k = 0.000
A4 = 3.11619e+00

Various data

| f | 0.857 |
| FNO. | 2.913 |
| 2ω | −163 |
| IH | 0.975 |
| LTL | 1.940 |
| BF | 0.97 |
| f1 | −5.725 |
| f2 | −1.067 |
| f3 | 0.501 |

Example 12

Unit mm

Surface data

| Surface no. | r | d | nd | νd |
| --- | --- | --- | --- | --- |
| Object plane | ∞ | 10.10 | | |
| 1* | −20.000 | 0.30 | 1.58913 | 61.15 |
| 2 | 0.800 | 0.30 | 1.80610 | 40.88 |
| 3* | 4.197 | 0.01 | | |
| 4(Stop) | ∞ | 0.00 | | |
| 5 | 22.625 | 0.30 | 1.84666 | 23.78 |
| 6 | 0.806 | 0.40 | 1.80610 | 40.92 |
| 7 | −0.675 | 0.88 | | |
| Image plane | −9.636 | | | |

Aspherical surface data

1st surface k = 0.000
A4 = −2.81491e−01, A6 = 8.35553e−01, A8 = −7.60061e−01
3rd surface k = 0.000
A4 = 1.86377e+00

Various data

| f | 0.853 |
| FNO. | 3.182 |
| 2ω | −164 |
| IH | 0.975 |
| LTL | 2.188 |
| BF | 0.88 |
| f1 | −1.294 |
| f2 | 1.173 |
| f3 | −0.984 |
| f4 | 0.515 |

Example 13

Unit mm

Surface data

| Surface no. | r | d | nd | νd |
| --- | --- | --- | --- | --- |
| Object plane | ∞ | 10.10 | | |
| 1 | ∞ | 0.30 | 1.53110 | 56.00 |
| 2* | 1.320 | 0.08 | | |
| 3(Stop) | ∞ | 0.00 | | |
| 4 | ∞ | 0.30 | 1.53110 | 56.00 |
| 5* | −0.417 | 1.19 | | |
| Image plane | −1.944 | | | |

Aspherical surface data

2nd surface k = 0.000
A4 = 7.73568e+00, A6 = −1.60978e+02, A8 = 2.89090e+03
5th surface k = 0.000
A4 = −8.07828e−01, A6 = −5.98277e+00, A8 = 6.06276e+01

Various data

| f | 0.980 |
| FNO. | 3.424 |
| 2ω | −161 |

-continued

Unit mm

| | |
|---|---|
| IH | 0.975 |
| LTL | 1.874 |
| BF | 1.19 |
| f1 | −2.476 |
| f2 | 0.781 |

Example 14

Unit mm

Surface data

| Surface no. | r | d | nd | vd |
|---|---|---|---|---|
| Object plane | ∞ | 10.10 | | |
| 1* | −20.000 | 0.30 | 1.58913 | 61.15 |
| 2 | 0.718 | 0.05 | | |
| 3 | 0.600 | 0.30 | 1.80610 | 40.88 |
| 4* | 1.791 | 0.02 | | |
| 5(Stop) | ∞ | 0.00 | | |
| 6 | 7.537 | 0.30 | 1.84666 | 23.78 |
| 7 | 0.806 | 0.40 | 1.80610 | 40.92 |
| 8 | −0.718 | 0.82 | | |
| Image plane | −9.571 | | | |

Aspherical surface data

1st surface k = 0.000
A4 = −2.27121e−01, A6 = 6.39527e−01, A8 = −5.44810e−01

4th surface k = 0.000
A4 = 1.75994e+00

Various data

| | |
|---|---|
| f | 0.853 |
| FNO. | 2.935 |
| 2ω | −164 |
| IH | 0.975 |
| LTL | 2.188 |
| BF | 0.82 |
| f1 | −1.166 |
| f2 | 1.000 |
| f3 | −1.078 |
| f4 | 0.531 |

Example 15

Unit mm

Surface data

| Surface no. | r | d | nd | vd |
|---|---|---|---|---|
| Object plane | ∞ | 10.10 | | |
| 1* | −5.808 | 0.30 | 1.58313 | 59.38 |
| 2 | ∞ | 0.00 | | |
| 3(Stop) | ∞ | 0.00 | | |
| 4 | ∞ | 0.53 | 1.80610 | 40.88 |
| 5* | −0.749 | 1.11 | | |
| Image plane | −2.149 | | | |

-continued

Unit mm

Aspherical surface data

1st surface k = 0.000
A4 = −1.59032e+00, A6 = 1.72225e+01, A8 = −7.34033e+01

5th surface k = 0.000
A4 = −2.02944e−02, A6 = −5.15218e−01, A8 = −2.59305e+00

Various data

| | |
|---|---|
| f | 0.966 |
| FNO. | 3.316 |
| 2ω | −161 |
| IH | 0.975 |
| LTL | 1.940 |
| BF | 1.11 |
| f1 | −9.920 |
| f2 | 0.923 |

Next, values of conditional expressions in each example are given below.
(1) SAG11/f, (2) |R2e/Rimg|, (3) L1e/TL, (4) PS×SAG11, (5) PS×EXP, (6) (EXP/f)/(φe/φ1), (A1) L/TL, (A2) R2e/R11, (A5) L1e/R11, (A6) PSinv/R11, (B1) |$R_e/R_1$|, (B2) $R_e$/TL′, (B3) $EXP_{60}$/f, (B4) $Y_1$×2/f, (B5) $L_{1e}$′/TL′, (B6) |$R_e/R_{img}$′|, (B7) $SAG_{11}$′/f, (B9) $PS_{inv}$/$R_1$, (B10) (EXP/f)/($φ_e$′/$φ_1$′)

| | Example 1 | Example 2 | Example 3 | Example 4 |
|---|---|---|---|---|
| (1) | −0.008 | −0.013 | −0.004 | −0.007 |
| (2) | 0.039 | 0.210 | 0.350 | 0.292 |
| (3) | 0.392 | 0.451 | 0.414 | 0.478 |
| (4) | −0.004 | −0.008 | −0.003 | −0.004 |
| (5) | −0.860 | −0.918 | −0.987 | −0.926 |
| (6) | −1.992 | −1.588 | −1.579 | −1.506 |
| (A1) | 0.028 | 0.030 | 0.016 | 0.032 |
| (A2) | 0.118 | 0.120 | 0.140 | −0.007 |
| (A5) | −0.217 | −0.209 | −0.212 | 0.011 |
| (A6) | −0.509 | −0.359 | −0.420 | 0.017 |
| (B1) | 0.118 | 0.120 | 0.140 | 0.007 |
| (B2) | −0.213 | −0.258 | −0.273 | −0.300 |
| (B3) | −1.629 | −1.481 | −1.584 | −1.352 |
| (B4) | 1.021 | 1.183 | 0.927 | 1.317 |
| (B5) | 0.392 | 0.451 | 0.414 | 0.478 |
| (B6) | 0.039 | 0.210 | 0.350 | 0.292 |
| (B7) | −0.008 | −0.013 | −0.004 | −0.007 |
| (B9) | −0.509 | −0.359 | −0.420 | 0.017 |
| (B10) | −1.992 | −1.588 | −1.579 | −1.506 |

| | Example 5 | Example 6 | Example 7 | Example 8 |
|---|---|---|---|---|
| (1) | −0.001 | −0.008 | −0.001 | −0.005 |
| (2) | 0.458 | 0.340 | 0.512 | 0.504 |
| (3) | 0.499 | 0.361 | 0.364 | 0.466 |
| (4) | −0.001 | −0.004 | −0.001 | −0.003 |
| (5) | −0.952 | −0.947 | −0.987 | −1.303 |
| (6) | −1.250 | −1.890 | −2.210 | −1.952 |
| (A1) | 0.026 | 0.028 | 0.028 | 0.027 |
| (A2) | −0.082 | 0.557 | 0.202 | 0.434 |
| (A5) | 0.114 | −0.442 | −0.172 | −0.378 |
| (A6) | 0.164 | −1.322 | −0.489 | −0.657 |
| (B1) | 0.082 | 0.557 | 0.202 | 0.434 |
| (B2) | −0.358 | −0.454 | −0.428 | −0.536 |
| (B3) | −1.312 | −2.042 | −1.968 | −2.166 |
| (B4) | 1.373 | 0.304 | 0.299 | 0.300 |
| (B5) | 0.499 | 0.361 | 0.364 | 0.466 |
| (B6) | 0.458 | 0.340 | 0.512 | 0.504 |
| (B7) | −0.001 | −0.008 | −0.001 | −0.005 |
| (B9) | 0.164 | −1.322 | −0.489 | −0.657 |
| B10) | −1.250 | −1.890 | −2.210 | −1.952 |

|  | Example 9 | Example 10 | Example 11 | Example 12 |
|---|---|---|---|---|
| (1) | −0.001 | −0.005 | −0.002 | −0.009 |
| (2) | 1.298 | 0.044 | 0.067 | 0.070 |
| (3) | 0.472 | 0.409 | 0.498 | 0.601 |
| (4) | −0.001 | −0.003 | −0.001 | −0.005 |
| (5) | −1.161 | −0.913 | −0.972 | −1.005 |
| (6) | −1.706 | −1.861 | −2.295 | −2.296 |
| (A1) | 0.029 | 0.030 | 0.010 | 0.005 |
| (A2) | 0.099 | 0.063 | 0.066 | 0.034 |
| (A5) | −0.041 | −0.099 | −0.097 | −0.066 |
| (A6) | −0.073 | −0.205 | −0.165 | −0.078 |
| (B1) | 0.099 | 0.063 | 0.066 | 0.034 |
| (B2) | −1.139 | −0.258 | −0.339 | −0.308 |
| (B3) | −1.808 | −1.482 | −1.857 | −1.836 |
| (B4) | 0.301 | 1.066 | 0.957 | 1.393 |
| (B5) | 0.472 | 0.409 | 0.498 | 0.601 |
| (B6) | 1.298 | 0.044 | 0.067 | 0.070 |
| (B7) | −0.001 | −0.005 | −0.002 | −0.009 |
| (B9) | −0.073 | −0.205 | −0.165 | −0.078 |
| (B10) | −1.706 | −1.861 | −2.295 | −2.296 |

|  | Example 13 | Example 14 | Example 15 |
|---|---|---|---|
| (1) | — | — | — |
| (2) | 0.214 | — | — |
| (3) | 0.365 | — | — |
| (5) | −0.829 | −0.935 | −0.822 |
| (6) | −2.501 | −2.589 | −1.767 |
| (A1) | 0.043 | — | — |
| (A2) | 0.000 | — | — |
| (A5) | 0.000 | — | — |
| (A6) | 0.000 | — | — |
| (B1) | 0.000 | 0.036 | 0.129 |
| (B2) | −0.222 | −0.328 | −0.386 |
| (B3) | −1.481 | −1.732 | −1.587 |
| (B4) | 0.995 | 1.548 | 0.702 |
| (B5) | 0.365 | 0.626 | 0.428 |
| (B6) | 0.214 | 0.075 | 0.348 |
| (B7) | 0.000 | −0.013 | −0.001 |
| (B9) | 0.000 | −0.080 | −0.322 |
| (B10) | −2.501 | −2.589 | −1.767 |

Moreover, values of parameters are given below. Here, $\phi_{EA}$ denotes a predetermined area, which is an area on the object-side optical surface through which an effective light beam passes.

|  | Example 1 | Example 2 | Example 3 | Example 4 |
|---|---|---|---|---|
| Rimg | −9.568 | −2.437 | −1.507 | −1.952 |
| L1e | 0.690 | 0.893 | 0.799 | 0.910 |
| PS | 0.617 | 0.651 | 0.631 | 0.719 |
| EXP | −1.393 | −1.409 | −1.565 | −1.289 |
| R11 | −3.185 | −4.280 | −3.773 | 83.990 |
| R2e | −0.375 | −0.512 | −0.527 | −0.570 |
| SAG11 | −0.007 | −0.013 | −0.004 | −0.006 |
| $\varphi 1$ | 0.274 | 0.275 | 0.284 | 0.288 |
| $\varphi e$ | 0.224 | 0.258 | 0.285 | 0.260 |
| PSinv | 1.620 | 1.535 | 1.585 | 1.391 |
| L | 0.050 | 0.060 | 0.030 | 0.060 |
| EXP$_{60}$ | −1.393 | −1.406 | −1.564 | −1.281 |
| $\varphi_{EA}$ | 0.873 | 1.122 | 0.915 | 1.248 |
| Y$_1$ | 0.436 | 0.561 | 0.458 | 0.624 |
| R$_{img}$' | −9.568 | −2.437 | −1.507 | −1.952 |
| L$_{1e}$' | 0.690 | 0.893 | 0.799 | 0.910 |
| R$_1$ | −3.185 | −4.280 | −3.773 | 83.990 |
| R$_e$ | −0.375 | −0.512 | −0.527 | −0.570 |
| SAG$_{11}$' | −0.007 | −0.013 | −0.004 | −0.006 |
| $\varphi_1$' | 0.274 | 0.275 | 0.284 | 0.288 |
| $\varphi_e$' | 0.224 | 0.258 | 0.285 | 0.260 |

|  | Example 5 | Example 6 | Example 7 | Example 8 |
|---|---|---|---|---|
| Rimg | −1.506 | −2.410 | −1.491 | −1.946 |
| L1e | 0.963 | 0.650 | 0.650 | 0.853 |
| PS | 0.725 | 0.514 | 0.542 | 0.675 |
| EXP | −1.313 | −1.841 | −1.823 | −1.931 |
| R11 | 8.422 | −1.471 | −3.775 | −2.258 |
| R2e | −0.690 | −0.819 | −0.764 | −0.981 |
| SAG11 | −0.001 | −0.008 | −0.001 | −0.005 |
| $\varphi 1$ | 0.297 | 0.297 | 0.297 | 0.296 |
| $\varphi e$ | 0.314 | 0.296 | 0.247 | 0.296 |
| PSinv | 1.379 | 1.945 | 1.846 | 1.482 |
| L | 0.050 | 0.050 | 0.050 | 0.050 |
| EXP$_{60}$ | −1.303 | −1.989 | −1.949 | −2.142 |
| $\varphi_{EA}$ | 1.363 | 0.296 | 0.296 | 0.296 |
| Y$_1$ | 0.682 | 0.148 | 0.148 | 0.148 |
| R$_{img}$' | −1.506 | −2.410 | −1.491 | −1.946 |
| L$_{1e}$' | 0.963 | 0.650 | 0.650 | 0.853 |
| R$_1$ | 8.422 | −1.471 | −3.775 | −2.258 |
| R$_e$ | −0.690 | −0.819 | −0.764 | −0.981 |
| SAG$_{11}$' | −0.001 | −0.008 | −0.001 | −0.005 |
| $\varphi_1$' | 0.297 | 0.297 | 0.297 | 0.296 |
| $\varphi_e$' | 0.314 | 0.296 | 0.247 | 0.296 |

|  | Example 9 | Example 10 | Example 11 | Example 12 |
|---|---|---|---|---|
| Rimg | −1.503 | −9.807 | −9.785 | −9.636 |
| L1e | 0.809 | 0.676 | 0.967 | 1.314 |
| PS | 0.690 | 0.718 | 0.608 | 0.637 |
| EXP | −1.682 | −1.271 | −1.599 | −1.577 |
| R11 | −19.712 | −6.802 | −10.000 | −20.000 |
| R2e | −1.951 | −0.427 | −0.658 | −0.675 |
| SAG11 | −0.001 | −0.004 | −0.002 | −0.008 |
| $\varphi 1$ | 0.296 | 0.283 | 0.288 | 0.259 |
| $\varphi e$ | 0.296 | 0.226 | 0.234 | 0.208 |
| PSinv | 1.448 | 1.392 | 1.646 | 1.569 |
| L | 0.050 | 0.050 | 0.020 | 0.010 |
| EXP$_{60}$ | −1.782 | −1.269 | −1.591 | −1.567 |
| $\varphi_{EA}$ | 0.296 | 0.913 | 0.820 | 1.189 |
| Y$_1$ | 0.148 | 0.456 | 0.410 | 0.594 |
| R$_{img}$' | −1.503 | −9.807 | −9.785 | −9.636 |
| L$_{1e}$' | 0.809 | 0.676 | 0.967 | 1.314 |
| R$_1$ | −19.712 | −6.802 | −10.000 | −20.000 |
| R$_e$ | −1.951 | −0.427 | −0.658 | −0.675 |
| SAG$_{11}$' | −0.001 | −0.004 | −0.002 | −0.008 |
| $\varphi_1$' | 0.296 | 0.283 | 0.288 | 0.259 |
| $\varphi_e$' | 0.296 | 0.226 | 0.234 | 0.208 |

|  | Example 13 | Example 14 | Example 15 |
|---|---|---|---|
| Rimg | −1.944 | — | — |
| L1e | 0.684 | — | — |
| PS | 0.571 | — | — |
| EXP | −1.451 | — | — |
| R11 | ∞ | — | — |
| R2e | −0.417 | — | — |
| $\varphi 1$ | 0.279 | — | — |
| $\varphi e$ | 0.165 | — | — |
| PSinv | 1.751 | — | — |
| L | 0.080 | — | — |
| EXP$_{60}$ | −1.451 | −1.478 | −1.534 |
| $\varphi_{EA}$ | 0.975 | 1.321 | 0.678 |
| Y$_1$ | 0.488 | 0.660 | 0.339 |
| R$_{img}$' | −1.944 | −9.571 | −2.149 |
| L$_{1e}$' | 0.684 | 1.369 | 0.829 |
| R$_1$ | ∞ | −20.000 | −5.808 |
| R$_e$ | −0.417 | −0.718 | −0.749 |
| SAG$_{11}$' | 0.000 | −0.011 | −0.001 |
| $\varphi_1$' | 0.279 | 0.279 | 0.286 |
| $\varphi_e$' | 0.165 | 0.188 | 0.258 |

Figure 21:
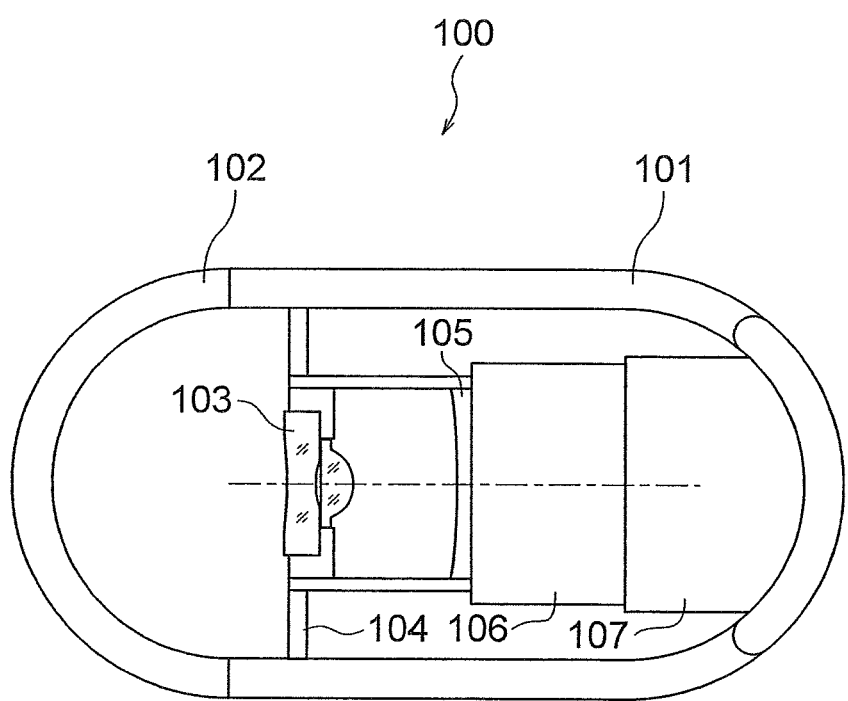
FIG. 21 is a diagram showing a schematic arrangement of a capsule endoscope.

FIG. 21 illustrates an example of an optical apparatus. In this example, the optical apparatus is a capsule endoscope. A capsule endoscope 100 includes a capsule cover 101 and a transparent cover 102. An outer covering of the capsule endoscope 100 is formed by the capsule cover 101 and the transparent cover 102.

The capsule cover 101 includes a central portion having a substantially circular cylindrical shape, and a bottom portion having a substantially bowl shape. The transparent cover 102 is disposed at a position facing the bottom portion, across the central portion. The transparent cover 102 is formed by a transparent member having a substantially bowl shape. The capsule cover 101 and the transparent cover 102 are connected consecutively to be mutually watertight.

An interior of the capsule endoscope 100 includes an image forming optical system 103, a illumination unit 104, an image pickup element 105, a drive control unit 106, and a signal processing unit 107. Although it is not shown in the diagram, the interior of the capsule endoscope 100 is provided with an electric-power receiving unit and a transmitting unit.

Illumination light is irradiated from the illumination unit 104. The illumination light passes through the transparent cover 102 and is irradiated to an object. Light from the object is incident on the image forming optical system 103. An optical image of the object is formed at an image position by the image forming optical system 103.

The optical image is picked up by the image pickup element 105. A drive and control of the image pickup element 105 is carried out by the drive control unit 106. Moreover, an output signal from the image pickup element 105 is processed by the signal processing unit 107 according to the requirement.

Here, the image forming optical system according to the example 1 mentioned above is used as the image forming optical system 103. Therefore, an optical image over an extremely wide range (angle of view of approximately 160°) is formed. Moreover, the optical image is an image curved to be concave toward the object side.

An image pickup surface of the image pickup element 105 is curved to be concave toward the object side. Moreover, a radius of curvature of the image pickup surface is same as a radius of curvature of the optical image. Consequently, it is possible to achieve a sharp image from a center up to a periphery, while being the image captured over an extremely wide range.

Figure 22A:
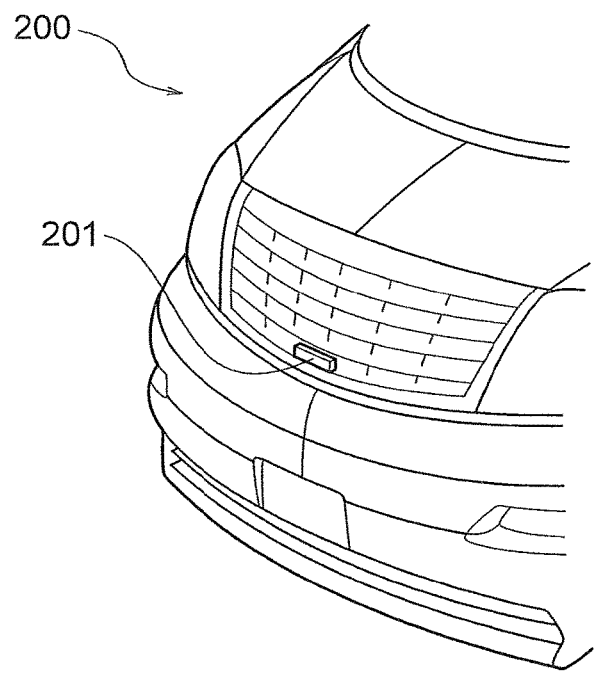
FIG. 22A is a diagram showing an example in which a car-mounted camera is installed outside of a car.
Figure 22B:
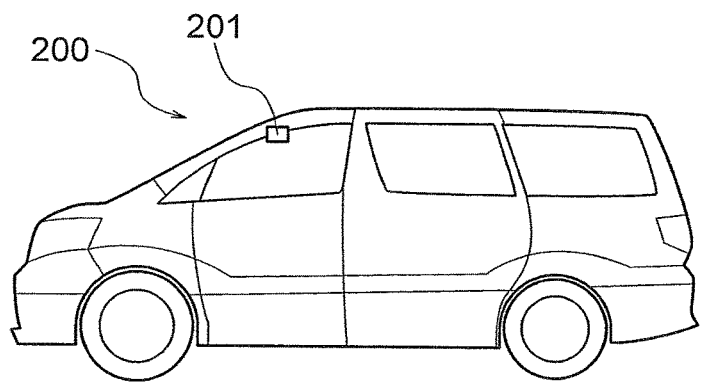
FIG. 22B is a diagram showing an example in which a car-mounted camera is installed inside a car.

FIG. 22A and FIG. 22B are diagrams illustrating another example of an optical apparatus. In this example, the optical apparatus is a car-mounted camera. FIG. 22A is a diagram illustrating an example of a car-mounted camera mounted at an outside of a car, and FIG. 22B is a diagram illustrating an example of a car-mounted camera mounted inside a car.

As shown in FIG. 22A, a car-mounted camera 201 is provided to a front grill of an automobile 200. The car-mounted camera 201 includes an image forming optical system and an image pickup element.

For the image forming optical system of the car-mounted camera 201, the image forming optical system according to the abovementioned example 1 is used. Consequently, an optical image of an extremely wide range (the angle of view of about 220°) is formed. Moreover, a radius of curvature of the image pickup surface is same as a radius of curvature of the optical image. Consequently, it is possible to achieve a sharp image from a center up to a periphery, while being the image captured over an extremely wide range.

As shown in FIG. 22B, the car-mounted camera 201 is provided near a ceiling of the automobile 200. An action and an effect of the car-mounted camera 201 are as have already been described.

The car-mounted camera 201, if to be installed outside of a car, may be disposed at an apex portion of a pole of a head portion or each corner. Moreover, if the car-mounted camera 201 is to be installed inside a car, it may be disposed near a back mirror.

The present invention also includes the following inventions which are conceived form abovementioned embodiments and examples.

(Appended Mode 1-8)

A image forming optical system comprising in order from the object side to the image side:

two lens components namely, the object-side lens component and the image-side lens component, wherein the lens component is a lens having two surfaces that are in contact with air in an effective optical path namely, an object-side surface and an image-side surface, and the following conditional expression (1-4) is satisfied:

$$PS \times SAG_{11} < 0 \qquad (1\text{-}4),$$

where, $SAG_{11}$ denotes a distance on the surface nearest to the object of the object-side lens component, in a direction along the optical axis, from an apex of the surface up to a point in which a most peripheral effective light ray incident at a maximum image height on the image forming optical system passes through the surface nearest to the object of the object-side lens component, letting a direction in which a light ray travels to be a positive direction, and PS denotes Petzval's sum for the image forming optical system, and here Petzval's sum PS is expressed by the following expression:

$$PS = \sum_{i=1}^{k} \frac{1}{n_i \times f_i}$$

where, i denotes an order of lenses from the object side in the image forming optical system, k denotes total number of lenses in the image forming optical system, $n_i$ denotes a refractive index for a d-line of an $i^{th}$ lens, and $f_i$ denotes a focal length of the $i^{th}$ lens.

(Appended Mode 1-9)

The image forming optical system according to Appended Mode 1-8, wherein the surface nearest to the object of the object-side lens component is a surface having a concave shape portion which is concave shape toward the object side in a meridional direction, in at least an off-axis effective surface.

(Appended Mode 1-10)

The image forming optical system according to Appended Mode 1-8 or 1-9, wherein the surface nearest to the image of the image-side lens component is convex shape toward the image side.

(Appended Mode 1-11)

The image forming optical system according to any one of Appended Modes 1-8 to 1-10, wherein the surface nearest to the object of the object-side lens component is an aspheric surface.

(Appended Mode 1-12)

The image pickup apparatus according to any one of Appended Modes 1-8 to 1-11, wherein the aspheric surface which is nearest to the object of the object-side lens component is a surface having an inflection point on the off-axis effective surface in a cross-section including an optical axis.

(Appended Mode 2-1)

An image forming optical system, comprising:

a plurality of lens components, and an aperture stops which limits an axial light beam, wherein the lens component is a lens having two surfaces that are in contact with air in an effective optical path namely, an object-side surface and an image-side surface, and the effective optical path is an optical path through which a light beam that contributes to image formation passes, and the plurality of lens components include in order from an object side to an image side, two lens components namely, an object-side lens component and an image-side lens component, and an image is formed on an image pickup surface which is curved to be concave toward the object side, and the following conditional expression (2-1) is satisfied:

$$PS \times EXP < -0.7 \tag{2-1},$$

where,

PS denotes Petzval's sum for the image forming optical system, and here

Petzval's sum PS is expressed by the following expression:

$$PS = \sum_{i=1}^{k} \frac{1}{n_i \times f_i}$$

where, i denotes an order of lenses from the object side in the image forming optical system, k denotes total number of lenses in the image forming optical system, $n_i$ denotes a refractive index for a d-line of an $i^{th}$ lens, $f_i$ denotes a focal length of the $i^{th}$ lens, and EXP denotes a distance along an optical axis from the image up to a paraxial exit pupil position of the image forming optical system, and is let to be negative when the paraxial exit pupil is on the object side of the image.

(Appended Mode 2-2)

The image forming optical system according to Appended Mode 2-1, wherein the aperture stop is disposed between the object-side lens component and the image-side lens component, and the following conditional expression (2-2) is satisfied:

$$L_{1e}/TL \le 0.65 \tag{2-2},$$

where, $L_{1e}$ denotes a distance on the optical axis from the surface nearest to the object of the object-side lens component up to the surface nearest to the image of the image-side lens component, and TL denotes a distance on the optical axis from the surface nearest to the object of the object-side lens component up to the image pickup surface.

(Appended Mode 2-3)

The image forming optical system according to Appended Mode 2-1 or 2-2, wherein the surface nearest to the object of the object-side lens component is a surface having a concave shape toward the object side.

(Appended Mode 2-4)

The image forming optical system according to Appended Mode 2-1 or 2-2, wherein the surface nearest to the object of the object-side lens component is a surface having a concave shape portion which is concave shape toward the object side in a meridional direction, in at least an off-axis effective surface.

(Appended Mode 2-5)

The image forming optical system according to any one of Appended Modes 2-1 to 2-4, wherein the surface nearest to the image of the image-side lens component is convex shape toward the image side.

(Appended Mode 2-6)

The image forming optical system according to any one of Appended Modes 2-1 to 2-5, wherein the surface nearest to the object of the object-side lens component is an aspheric surface.

(Appended Mode 2-7)

An image pickup apparatus, comprising:

an image forming optical system according to any one of Appended Modes 2-1 to 2-6; and an image pickup unit having an image pickup surface curved to be concave toward the object side, which is disposed on the image side of the image forming optical system.

(Appended Mode 3-1)

An image forming optical system, comprising:

a plurality of lens components, and an aperture stops which limits an axial light beam, wherein the lens component is a lens having two surfaces that are in contact with air in an effective optical path namely, an object-side surface and an image-side surface, and the effective optical path is an optical path through which a light beam that contributes to image formation passes, and the plurality of lens components include in order from an object side to an image side, two lens components namely, an object-side lens component and an image-side lens component, and an image is formed on an image pickup surface which is curved to be concave toward the object side, and the following conditional expression (3-1) is satisfied:

$$(EXP/f)/(\phi_e/\phi_1) < -1.3 \tag{3-1},$$

where,

EXP denotes a distance along an optical axis from the image up to a paraxial exit pupil position of the image forming optical system, and is let to be negative when the paraxial exit pupil position is on the object side of the image, f denotes a focal length of the image forming optical system, $\phi_e$ denotes a maximum diameter of an area on the surface nearest to the object of the object-side lens component through which an effective light beam that contributes to image formation at a maximum image height position passes, when measured perpendicularly with respect to the optical axis, and $\phi_1$ denotes a maximum diameter of an area on the surface nearest to the object of the object-side lens component through which an axial light beam of the image forming optical system passes, when measured perpendicularly with respect to the optical axis.

(Appended Mode 3-2)

The image forming optical system according to Appended Mode 3-1, wherein the following conditional expression (3-2) is satisfied:

$$L_{1e}/TL \le 0.65 \tag{3-2},$$

where, $L_{1e}$ denotes a distance on the optical axis from the surface nearest to the object of the object-side lens component up to the surface nearest to the image of the image-side lens component, and TL denotes a distance on the optical axis from the surface nearest to the object of the object-side lens component up to the image pickup surface.

(Appended Mode 3-3)

The image forming optical system according to Appended Mode 3-1 or 3-2, wherein the surface nearest to the object of the object-side lens component is a surface having a concave shape toward the object side.

(Appended Mode 3-4)

The image forming optical system according to Appended Mode 3-1 or 3-2, wherein the surface nearest to the object of the object-side lens component is a surface having a concave shape portion which is concave shape toward the object side in a meridional direction, in at least an off-axis effective surface.

(Appended Mode 3-5)

The image forming optical system according to any one of Appended Mode 3-1 to 3-4, wherein the surface nearest to the image of the image-side lens component is convex shape toward the image side.

(Appended Mode 3-6)

The image forming optical system according to any one of Appended Modes 3-1 to 3-5, wherein the surface nearest to the object of the object-side lens component is an aspheric surface.

(Appended Mode 3-7)

An image pickup apparatus, comprising:

an image forming optical system according to any one of Appended Mode 3-1 to 3-6; and an image pickup unit having an image pickup surface curved to be concave toward the object side, which is disposed on the image side of the image forming optical system.

(Appended Mode 4-1)

An image pickup apparatus, comprising:

an image forming optical system having lens components; and an image pickup unit, wherein the lens component is a lens having an object-side surface and an image-side surface that are in contact with air in an effective optical path, and the effective optical path is an optical path through which a light beam that contributes to image formation passes, and the image forming optical system includes in order from an object side to an image side, an object-side lens component and an image-side lens component, and the image pickup unit has an image pickup surface curved to be concave toward the object side, which is disposed on the image side of the image forming optical system, and a surface nearest to an object of the object-side lens component is a surface having a concave shape portion which is concave shape toward the object side in a meridional direction, in at least an off-axis effective surface, and a surface nearest to an image of the image-side lens component is a curved surface.

(Appended Mode 4-2)

An image pickup apparatus, comprising:

an image forming optical system having lens components; and an image pickup unit, wherein the lens component is a lens having an object-side surface and an image-side surface that are in contact with air in an effective optical path, and the effective optical path is an optical path through which a light beam that contributes to image formation passes, and the image forming optical system includes in order from an object side to an image side, an object-side lens component and an image-side lens component, and the image pickup unit has an image pickup surface curved to be concave toward the object side, which is disposed on the image side of the image forming optical system, and a surface nearest to an object of the object-side lens component is one of a flat surface and a surface having a concave shape toward the object side, and a surface nearest to an image of the image-side lens component is a curved surface, and the following conditional expression (A1) is satisfied:

$$0 < L/TL \le 0.4 \quad (A1),$$

where,

L denotes a distance on an optical axis from a surface nearest to the image of the object-side lens component up to a surface nearest to the object of the image-side lens component, and TL denotes a distance on the optical axis from the surface nearest to the object of the object-side lens component up to the image pickup surface.

(Appended Mode 4-3)

An image forming optical system, comprising:

a plurality of lens components, wherein the lens component is a lens having an object-side surface and an image-side surface that are in contact with air in an effective optical path, and the effective optical path is an optical path through which a light beam that contributes to image formation passes, and the plurality of lens components include in order from an object side to an image side, an object-side lens component and an image-side lens component, and an image is formed on an image pickup surface which is curved to be concave toward the object side, and the following conditional expression (A5) is satisfied:

$$L_{1e}/R_{11} \le 0 \quad (A5),$$

where, $L_{1e}$ denotes a distance on an optical axis from a surface nearest to an object of the object-side lens component up to a surface nearest to the image of the image-side lens component, and $R_{11}$ denotes a radius of curvature of the surface nearest to the object of the object-side lens component.

(Appended Mode 4-4)

An image forming optical system comprising:

a plurality of lens components, wherein the lens component is a lens having an object-side surface and an image-side surface that are in contact with air in an effective optical path, and the effective optical path is an optical path through which a light beam that contributes to image formation passes, and the plurality of lens components include in order from an object side to an image side, an object-side lens component and an image-side lens component, and an image is formed on an image pickup surface which is curved to be concave toward the object side, and the following conditional expression (A6) is satisfied:

$$PS_{inv}/R_{11} \le 0 \quad (A6),$$

where, $R_{11}$ denotes a radius of curvature of a surface nearest to an object of the object-side lens component, and $PS_{inv}$ denotes an inverse number of Petzval's sum for the image forming optical system, and here Petzval's sum PS is expressed by the following expression:

$$PS = \sum_{i=1}^{k} \frac{1}{n_i \times f_i}$$

where, i denotes an order from the object side of lenses in the image forming optical system, k denotes total number of lenses in the image forming optical system, $n_i$ denotes a refractive index for a d-line of an $i^{th}$ lens, and $f_i$ denotes a focal length of the $i^{th}$ lens.

(Appended Mode 4-5)

An image forming optical system, comprising:

a plurality of lens components, and an aperture stops which limits an axial light beam, wherein the lens component is a lens having an object-side surface and an image-side surface that are in contact with air in an effective optical path, and the effective optical path is an optical path through which a light beam that contributes to image formation passes, and the plurality of lens components include in order from an object side to an image side, an object-side lens component and an image-side lens component, and an image is formed on an image pickup surface which is curved to be concave toward the object side, and the following conditional expression (5) is satisfied:

$$PS \times EXP < -0.7 \tag{5}$$

where,

PS denotes Petzval's sum for the image forming optical system, and here

Petzval's sum PS is expressed by the following expression:

$$PS = \sum_{i=1}^{k} \frac{1}{n_i \times f_i}$$

where, i denotes an order of lenses from the object side in the image forming optical system, k denotes total number of lenses in the image forming optical system, $n_i$ denotes a refractive index for a d-line of an $i^{th}$ lens, $f_i$ denotes a focal length of the $i^{th}$ lens, and EXP denotes a distance along an optical axis from the image up to a paraxial exit pupil position of the image forming optical system, and is let to be negative when the paraxial exit pupil is on the object side of the image.

(Appended Mode 4-6)

An image forming optical system, comprising:

a plurality of lens components, and an aperture stops which limits an axial light beam, wherein the lens component is a lens having an object-side surface and an image-side surface that are in contact with air in an effective optical path, and the effective optical path is an optical path through which a light beam that contributes to image formation passes, and the plurality of lens components include in order from an object side to an image side, an object-side lens component and an image-side lens component, and an image is formed on an image pickup surface which is curved to be concave toward the object side, and the following conditional expression (6) is satisfied:

$$(EXP/f)/(\phi_e/\phi_1) < -1.3 \tag{6}$$

where,

EXP denotes a distance along an optical axis from the image up to a paraxial exit pupil position of the image forming optical system, and is let to be negative when the paraxial exit pupil position is on the object side of the image, f denotes a focal length of the image forming optical system, $\phi_e$ denotes a maximum diameter of an area on the surface nearest to the object of the object-side lens component through which an effective light beam that contributes to image formation at a maximum image height position passes, when measured perpendicularly with respect to the optical axis, and $\phi_1$ denotes a maximum diameter of an area on the surface nearest to the object of the object-side lens component through which an axial light beam of the image forming optical system passes, when measured perpendicularly with respect to the optical axis.

(Appended Mode 4-7)

An image forming optical system which forms an image curved to be concave toward an object side, comprising:

an object-side optical surface which is positioned nearest to an object; and an image-side optical surface which is positioned nearest to the image, wherein the following conditional expressions (B1), (B2), (B3), and (B4) are satisfied:

$$0 \leq |R_e/R_1| < 0.8 \tag{B1}$$

$$R_e/TL' < 0 \tag{B2}$$

$$EXP_{60}/f < 0 \tag{B3, and}$$

$$0 < Y_1 \times 2/f < 2 \tag{B4}$$

where, $R_1$ denotes a paraxial radius of curvature of the object-side optical surface, $R_e$ denotes a paraxial radius of curvature of the image-side optical surface, TL' denotes a distance on an optical axis from the object-side optical surface up to the image, $EXP_{60}$ denotes an exit-pupil position by a light ray incident on the image forming optical system at a half angle of view of 60 degrees, f denotes a focal length of the image forming optical system, and $Y_1$ denotes a maximum light ray height in a predetermined area, and here the predetermined area is an area on the object-side optical surface through which an effective light beam passes.

(Appended Mode 4-8)

The image forming optical system according to Appended Mode 4-7, wherein when the lens component is let to be a lens having an object-side surface and an image-side surface that are in contact with air in the effective optical path through which a light beam contributing to the image formation passes, the image forming optical system includes in order from the object side to the image side, an object-side lens component and an image-side lens component.

It is preferable to satisfy the plurality of abovementioned inventions simultaneously, as it shows more assured effects of small-sizing, superior performance, and widening of the angle of view.

According to the present embodiment, it is possible to provide an image pickup apparatus in which an optical performance can be easily secured with a small number of lens components.

According to the present embodiment, it is possible to provide an image forming optical system, an image pickup apparatus, and a capsule endoscope in which an optical performance can be easily secured, while being small-sized.

According to the present embodiment, it is possible to provide an image forming optical system having a wide angle of view and superior imaging performance, while being small-sized. Moreover, it is possible to provide an optical system which is capable of capturing an image with high resolution over a wide range, while being small-sized.

As described heretofore, the present invention is useful for an image pickup apparatus which is capable of capturing an image with high resolution over a wide range, with a small number of lens components, while being small-sized.

Moreover, the present invention is useful for an image forming optical system having a wide angle of view and superior imaging performance with a small number of lens components, while being small-sized. Moreover, the present invention is useful for an image pickup apparatus and a capsule endoscope capable of capturing an image with high resolution over a wide range, with a small number of lens components, while being small-sized.

Moreover, the present invention is useful for an image forming optical system having a wide angle of view and superior imaging performance, while being small-sized. Furthermore, the present invention is useful for an optical apparatus which is capable of capturing an image with high resolution over a wide range, while being small-sized.

What is claimed is:

1. An image pickup apparatus, comprising:
an image forming optical system; and
an image pickup unit,
wherein:
the image forming optical system includes, in order from an object side to an image side, an object-side lens component and an image-side lens component,
the object-side lens component has a negative refractive power,
the image-side lens component has a positive refractive power,
each of the object-side lens component and the image-side lens component has an object-side surface and an image-side surface that are the only two surfaces thereof that are in contact with air in an effective optical path,
the effective optical path is an optical path through which a light beam that contributes to image formation passes,
a total number of lens elements of the object-side lens component is at most two,
the image pickup unit has an image pickup surface curved to be concave toward the object side, which is disposed on the image side of the image forming optical system,
a surface nearest to an object of the object-side lens component is a surface having a concave shape portion which is concave in shape toward the object side in a meridional direction, in at least an off-axis effective surface, and
a surface nearest to an image of the image-side lens component is a curved surface.

2. The image pickup apparatus according to claim 1, wherein the surface nearest to the image of the image-side lens component is a surface which is convex in shape toward the image side.

3. The image pickup apparatus according to claim 1, wherein the surface nearest to the object of the object-side lens component is an aspheric surface.

4. The image pickup apparatus according to claim 3, wherein the aspheric surface is a surface having an inflection point on the off-axis effective surface in a cross-section including an optical axis.

5. The image pickup apparatus according to claim 1, wherein the following conditional expression (1) is satisfied:

$$SAG_{11}/f<0 \quad (1),$$

where,
$SAG_{11}$ denotes a distance on the surface nearest to the object of the object-side lens component, in a direction along an optical axis, from an apex of the surface up to a point in which a most peripheral effective light ray incident at a maximum image height on the image forming optical system passes through the surface nearest to the object of the object-side lens component, letting a direction in which a light ray travels to be a positive direction, and
f denotes a focal length of the image forming optical system.

6. The image pickup apparatus according to claim 1, wherein the following conditional expression (2) is satisfied:

$$0<|R_{2e}/R_{img}|\leq 2.0 \quad (2),$$

where,
$R_{2e}$ denotes a radius of curvature of the surface nearest to the image of the image-side lens component, and
$R_{img}$ denotes a minimum value of a radius of curvature of a virtual spherical surface which includes an apex and a point at which a light ray incident on the image forming optical system at a half angle of view of 60 degrees intersects the image pickup surface, letting a point of intersection of the optical axis and the image pickup surface to be the apex.

7. The image pickup apparatus according to claim 1, wherein the following conditional expression (3) is satisfied:

$$L_{1e}/TL\leq 0.65 \quad (3),$$

where,
$L_{1e}$ denotes a distance on an optical axis from the surface nearest to the object of the object-side lens component up to the surface nearest to the image of the image-side lens component, and
TL denotes a distance on the optical axis from the surface nearest to the object of the object-side lens component up to the image pickup surface.

8. The image pickup apparatus according to claim 1, wherein
the image is formed on the image pickup surface which is curved to be concave toward the object side, and
the following conditional expression (4) is satisfied:

$$PS\times SAG_{11}<0 \quad (4),$$

where,

SAG$_{11}$ denotes a distance on the surface nearest to the object of the object-side lens component, in a direction along the optical axis, from an apex of the surface up to a point in which a most peripheral effective light ray incident at a maximum image height on the image forming optical system passes through the surface nearest to the object of the object-side lens component, letting a direction in which a light ray travels to be a positive direction, and PS denotes Petzval's sum for the image forming optical system, and here Petzval's sum PS is expressed by the following expression:

$$PS = \sum_{i=1}^{k} \frac{1}{n_i \times f_i}$$

where, i denotes an order of lenses from the object side in the image forming optical system, k denotes total number of lenses in the image forming optical system, n$_i$ denotes a refractive index for a d-line of an i$^{th}$ lens, and f$_i$ denotes a focal length of the i$^{th}$ lens.

9. The image pickup apparatus according to claim 1, further comprising:
an aperture stop which limits an axial light beam,
wherein the following conditional expression (5) is satisfied:

$$PS \times EXP < -0.7 \quad (5),$$

where,

PS denotes Petzval's sum for the image forming optical system, and here Petzval's sum PS is expressed by the following expression:

$$PS = \sum_{i=1}^{k} \frac{1}{n_i \times f_i}$$

where, i denotes an order of lenses from the object side in the image forming optical system, k denotes total number of lenses in the image forming optical system, n$_i$ denotes a refractive index for a d-line of an i$^{th}$ lens, f$_i$ denotes a focal length of the i$^{th}$ lens, and EXP denotes a distance along an optical axis from the image up to a paraxial exit pupil position of the image forming optical system, and is let to be negative when the paraxial exit pupil is on the object side of the image.

10. The image pickup apparatus according to claim 9, wherein the aperture stop is disposed between the object-side lens component and the image-side lens component.

11. The image pickup apparatus according to claim 1, further comprising:
an aperture stop which limits an axial light beam,
wherein the following conditional expression (6) is satisfied:

$$(EXP/f)/(\phi_e/\phi_1) < -1.3 \quad (6),$$

where,

EXP denotes a distance along an optical axis from the image up to a paraxial exit pupil position of the image forming optical system, and is let to be negative when the paraxial exit pupil position is on the object side of the image, f denotes a focal length of the image forming optical system, $\phi_e$ denotes a maximum diameter of an area on the surface nearest to the object of the object-side lens component through which an effective light beam that contributes to image formation at the maximum image height position passes, when measured perpendicularly with respect to the optical axis, and $\phi_1$ denotes a maximum diameter of an area on the surface nearest to the object of the object-side lens component through which an axial light beam of the image forming optical system passes, when measured perpendicularly with respect to the optical axis.

12. The image pickup apparatus according to claim 1, further comprising:
an illumination unit; and
a transparent cover which simultaneously covers a front surface of both the image forming optical system and the illumination unit.

13. The image pickup apparatus according to claim 12, wherein the image pickup apparatus is constructed as a capsule endoscope.

14. An image pickup apparatus, comprising:
an image forming optical system; and
an image pickup unit,
wherein:
the image forming optical system includes, in order from an object side to an image side, an object-side lens component and an image-side lens component,
the object-side lens component has a negative refractive power,
the image-side lens component has a positive refractive power,
each of the object-side lens component and the image-side lens component has an object-side surface and an image-side surface that are the only two surfaces thereof that are in contact with air in an effective optical path,
the effective optical path is an optical path through which a light beam that contributes to image formation passes,
the image pickup unit has an image pickup surface curved to be concave toward the object side, which is disposed on the image side of the image forming optical system,
a surface nearest to an object of the object-side lens component is one of a flat surface and a surface having a concave shape toward the object side,
a surface nearest to an image of the image-side lens component is a curved surface, and
the following conditional expression (A1) is satisfied:

$$0 < L/TL \leq 0.032 \quad (A1),$$

where,

L denotes a distance on an optical axis from a surface nearest to the image of the object-side lens component up to a surface nearest to the object of the image-side lens component, and TL denotes a distance on the optical axis from the surface nearest to the object of the object-side lens component up to the image pickup surface.

15. The image pickup apparatus according to claim 14, wherein the surface nearest to the image of the image-side lens component is a surface which is convex in shape toward the image side.

16. The image pickup apparatus according to claim 14, wherein the surface nearest to the object of the object-side lens component is an aspheric surface.

17. The image pickup apparatus according to claim 14, wherein
the surface nearest to the image of the image-side lens component is a surface which is convex in shape toward the image side, and
the following conditional expression (A2) is satisfied:

$$0 \le R_{2e}/R_{11} < 1.0 \tag{A2}$$

where,
$R_{11}$ denotes a radius of curvature of the surface nearest to the object of the object-side lens component, and
$R_{2e}$ denotes a radius of curvature of the surface nearest to the image of the image-side lens component.

18. The image pickup apparatus according to claim 14, wherein the following conditional expression (2) is satisfied:

$$0 < |R_{2e}/R_{img}| \le 2.0 \tag{2}$$

where,
$R_{2e}$ denotes a radius of curvature of the surface nearest to the image of the image-side lens component, and
$R_{img}$ denotes a minimum value of a radius of curvature of a virtual spherical surface which includes an apex and a point at which a light ray incident on the image forming optical system at a half angle of view of 60 degrees intersects the image pickup surface, letting a point of intersection of the optical axis and the image pickup surface to be the apex.

19. The image pickup apparatus according to claim 14, wherein the following conditional expression (3) is satisfied:

$$L_{1e}/TL \le 0.65 \tag{3}$$

where,
$L_{1e}$ denotes a distance on the optical axis from the surface nearest to the object of the object-side lens component up to the surface nearest to the image of the image-side lens component, and
TL denotes the distance on the optical axis from the surface nearest to the object of the object-side lens component up to the image pickup surface.

20. An image forming optical system comprising, in order from an object side to an image side:
an object-side lens component; and
an image-side lens component,
wherein:
the object-side lens component has a negative refractive power,
the image-side lens component has a positive refractive power,
each of the object-side lens component and the image-side lens component has an object-side surface and an image-side surface that are the only two surfaces thereof that are in contact with air in an effective optical path,
the effective optical path is an optical path through which a light beam that contributes to image formation passes,
a total number of lens elements of the object-side lens component is at most two,
an image is formed on an image pickup surface which is curved to be concave toward the object side, and
the following conditional expression (A5) is satisfied:

$$L_{1e}/R_{11} \le 0 \tag{A5}$$

where,
$L_{1e}$ denotes a distance on an optical axis from a surface nearest to an object of the object-side lens component up to a surface nearest to the image of the image-side lens component, and
$R_{11}$ denotes a radius of curvature of the surface nearest to the object of the object-side lens component.

21. An image forming optical system, comprising:
a plurality of lens components,
wherein:
each of the plurality of lens components is a lens having an object-side surface and an image-side surface that are in contact with air in an effective optical path,
the effective optical path is an optical path through which a light beam that contributes to image formation passes,
the plurality of lens components include, in order from an object side to an image side, an object-side lens component and an image-side lens component,
the object-side lens component has a negative refractive power,
the image-side lens component has a positive refractive power,
an image is formed on an image pickup surface which is curved to be concave toward the object side, and
the following conditional expression (A6) is satisfied:

$$PS_{inv}/R_{11} \le 0 \tag{A6}$$

where,
$R_{11}$ denotes a radius of curvature of a surface nearest to an object of the object-side lens component, and
$PS_{inv}$ denotes an inverse number of Petzval's sum for the image forming optical system, and here
Petzval's sum PS is expressed by the following expression:

$$PS = \sum_{i=1}^{k} \frac{1}{n_i \times f_i}$$

where,
i denotes an order from the object side of lenses in the image forming optical system,
k denotes total number of lenses in the image forming optical system,
$n_i$ denotes a refractive index for a d-line of an $i^{th}$ lens, and
$f_i$ denotes a focal length of the $i^{th}$ lens.

22. The image forming optical system according to claim 20, wherein the surface nearest to the object of the object-side lens component is one of a flat surface and a surface having a concave shape toward the object side.

23. The image forming optical system according to claim 20, wherein the surface nearest to the image of the image-side lens component is a surface which is convex in shape toward the image side.

24. The image forming optical system according to claim 20, wherein the surface nearest to the object of the object-side lens component is an aspheric surface.

25. An image pickup apparatus, comprising:
the image forming optical system according to claim 20; and
an image pickup unit having the image pickup surface curved to be concave toward the object side, which is disposed on the image side of the image forming optical system.

26. A capsule endoscope, comprising:
the image forming optical system according to claim 20;
an image pickup unit having the image pickup surface curved to be concave toward the object side, which is disposed on the image side of the image forming optical system; and
a cover portion having a dome shape, which is disposed on the object side of the image forming optical system.

27. An image forming optical system, comprising:
a plurality of lens components; and
an aperture stop which limits an axial light beam, wherein:
each of the plurality of lens components is a lens having an object-side surface and an image-side surface that are in contact with air in an effective optical path,
the effective optical path is an optical path through which a light beam that contributes to image formation passes,
the plurality of lens components include, in order from an object side to an image side, an object-side lens component and an image-side lens component,
an image is formed on an image pickup surface which is curved to be concave toward the object side, and
the following conditional expression (5) is satisfied:

$$PS \times EXP < -0.7 \qquad (5),$$

where,
PS denotes Petzval's sum for the image forming optical system, and here Petzval's sum PS is expressed by the following expression:

$$PS = \sum_{i=1}^{k} \frac{1}{n_i \times f_i}$$

where,
i denotes an order of lenses from the object side in the image forming optical system,
k denotes total number of lenses in the image forming optical system,
$n_i$ denotes a refractive index for a d-line of an $i^{th}$ lens,
$f_i$ denotes a focal length of the $i^{th}$ lens, and
EXP denotes a distance along an optical axis from the image up to a paraxial exit pupil position of the image forming optical system, and is let to be negative when the paraxial exit pupil is on the object side of the image.

28. The image forming optical system according to claim 27, wherein
the aperture stop is disposed between the object-side lens component and the image-side lens component, and the following conditional expression (3) is satisfied:

$$L_{1e}/TL \leq 0.65 \qquad (3),$$

where,
$L_{1e}$ denotes a distance on the optical axis from the surface nearest to the object of the object-side lens component up to the surface nearest to the image of the image-side lens component, and
TL denotes a distance on the optical axis from the surface nearest to the object of the object-side lens component up to the image pickup surface.

29. The image forming optical system according to claim 27, wherein the surface nearest to the object of the object-side lens component is one of a flat surface and a surface having a concave shape toward the object side.

30. The image forming optical system according to claim 27, wherein the surface nearest to the object of the object-side lens component is a surface having a concave shape portion which is concave in shape toward the object side in a meridional direction, in at least an off-axis effective surface.

31. The image forming optical system according to claim 27, wherein the surface nearest to the image of the image-side lens component is convex in shape toward the image side.

32. The image forming optical system according to claim 27, wherein the surface nearest to the object of the object-side lens component is an aspheric surface.

33. An image pickup apparatus, comprising:
the image forming optical system according to claim 27; and
an image pickup unit having the image pickup surface curved to be concave toward the object side, which is disposed on the image side of the image forming optical system.

34. An image forming optical system, comprising:
a plurality of lens components; and
an aperture stop which limits an axial light beam, wherein:
each of the plurality of lens components is a lens having an object-side surface and an image-side surface that are in contact with air in an effective optical path,
the effective optical path is an optical path through which a light beam that contributes to image formation passes,
the plurality of lens components include, in order from an object side to an image side, an object-side lens component and an image-side lens component,
an image is formed on an image pickup surface which is curved to be concave toward the object side, and
the following conditional expression (6) is satisfied:

$$(EXP/f)/(\phi_e/\phi_1) < -1.3 \qquad (6),$$

where,
EXP denotes a distance along an optical axis from the image up to a paraxial exit pupil position of the image forming optical system, and is let to be negative when the paraxial exit pupil position is on the object side of the image,
f denotes a focal length of the image forming optical system,
$\phi_e$ denotes a maximum diameter of an area on the surface nearest to the object of the object-side lens component through which an effective light beam that contributes to image formation at a maximum image height position passes, when measured perpendicularly with respect to the optical axis, and
$\phi_1$ denotes a maximum diameter of an area on the surface nearest to the object of the object-side lens component through which an axial light beam of the image forming optical system passes, when measured perpendicularly with respect to the optical axis.

35. The image forming optical system according to claim 34, wherein the following conditional expression (3) is satisfied:

$$L_{1e}/TL \leq 0.65 \qquad (3),$$

where,
$L_{1e}$ denotes a distance on the optical axis from the surface nearest to the object of the object-side lens component up to the surface nearest to the image of the image-side lens component, and
TL denotes a distance on the optical axis from the surface nearest to the object of the object-side lens component up to the image pickup surface.

36. The image forming optical system according to claim 34, wherein the surface nearest to the object of the object-side lens component is one of a flat surface and a surface having a concave shape toward the object side.

37. The image forming optical system according to claim 34, wherein a surface nearest to an object of the object-side lens component is a surface having a concave shape portion which is concave in shape toward the object side in a meridional direction, in at least an off-axis effective surface.

38. The image pickup apparatus according to claim 34, wherein the surface nearest to the image of the image-side lens component is convex in shape toward the image side.

39. The image pickup apparatus according to claim 34, wherein the surface nearest to the object of the object-side lens component is an aspheric surface.

40. An image pickup apparatus, comprising:
the image forming optical system according to claim 34; and
an image pickup unit having the image pickup surface curved to be concave toward the object side, which is disposed on the image side of the image forming optical system.

41. The image pickup apparatus according to claim 14, further comprising:
an illumination unit; and
a cover portion which is disposed on the object side of the image forming optical system.

42. A capsule endoscope, comprising:
the image forming optical system according to claim 21;
an image pickup unit having the image pickup surface curved to be concave toward the object side, which is disposed on the image side of the image forming optical system; and
a cover portion having a dome shape, which is disposed on the object side of the image forming optical system.

43. An image forming optical system which forms an image curved to be concave toward an object side, comprising:
an object-side optical surface which is positioned nearest to an object; and
an image-side optical surface which is positioned nearest to the image,
wherein the following conditional expressions (B1), (B2), (B3), and (B4) are satisfied:

$$0 \leq |R_e/R_1| < 0.8 \tag{B1}$$

$$R_e/TL' < 0 \tag{B2}$$

$$EXP_{60}/f < 0 \tag{B3, and}$$

$$0 < Y_1 \times 2/f < 2 \tag{B4}$$

where,
$R_1$ denotes a paraxial radius of curvature of the object-side optical surface,
$R_e$ denotes a paraxial radius of curvature of the image-side optical surface,
TL' denotes a distance on an optical axis from the object-side optical surface up to the image,
$EXP_{60}$ denotes an exit-pupil position by a light ray incident on the image forming optical system at a half angle of view of 60 degrees,
f denotes a focal length of the image forming optical system, and
$Y_1$ denotes a maximum light ray height in a predetermined area, and here the predetermined area is an area on the object-side optical surface through which an effective light beam passes.

44. The image forming optical system according to claim 43, wherein the following conditional expression (B5) is satisfied:

$$L_{1e}'/TL' \leq 0.65 \tag{B5}$$

where,
$L_{1e}'$ denotes a distance on the optical axis from the object-side optical surface up to the image-side optical surface, and
TL' denotes the distance on the optical axis from the object-side optical surface up to the image.

45. The image forming optical system according to claim 43, wherein the object of the object-side lens component is an aspheric surface.

46. The image forming optical system according to claim 43, wherein the following conditional expression (B6) is satisfied:

$$0 < |R_e/R_{img}'| \leq 2.0 \tag{B6}$$

where,
$R_e$ denotes the paraxial radius of curvature of the image-side optical surface, and
$R_{img}'$ denotes a minimum value of a radius of curvature of a virtual spherical surface which includes an apex and a point at which a light ray incident on the image forming optical system at a half angle of view of 60 degrees intersects the image, letting a point of intersection of the optical axis and the image to be the apex.

47. The image forming optical system according to claim 43, wherein the following conditional expression (B7) is satisfied:

$$SAG_{11}'/f \leq 0 \tag{B7}$$

where,
$SAG_{11}'$ denotes a distance in a direction along the optical axis, from an apex of the object-side optical surface up to a point in which a most peripheral effective light ray incident at a maximum image height on the image forming optical system passes through the object-side optical surface, letting a direction in which a light ray travels to be a positive direction, and
f denotes the focal length of the image forming optical system.

48. The image forming optical system according to claim 43, comprising:
an aperture stop which limits an axial light beam, wherein the following conditional expression (5) is satisfied:

$$PS \times EXP < -0.7 \tag{5}$$

where,
PS denotes Petzval's sum for the image forming optical system, and here Petzval's sum PS is expressed by the following expression:

$$PS = \sum_{i=1}^{k} \frac{1}{n_i \times f_i}$$

where,
i denotes a order of lenses from the object side in the image forming optical system,
k denotes total number of lenses in the image forming optical system, $n_i$ denotes a refractive index for a d-line of an $i^{th}$ lens,
$f_i$ denotes a focal length of the $i^{th}$ lens, and
EXP denotes a distance along the optical axis from the image up to a paraxial exit pupil position of the image forming optical system, and is let to be negative when the paraxial exit pupil is on the object side of the image.

49. The image forming optical system according claim 43, wherein the following conditional expression (B9) is satisfied:

$$PS_{inv}/R_1 \leq 0 \qquad (B9),$$

where,
$R_1$ denotes the paraxial radius of curvature of the object-side optical surface, and
$PS_{inv}$ denotes an inverse number of Petzval's sum for the image forming optical system, and here
Petzval's sum PS is expressed by the following expression:

$$PS = \sum_{i=1}^{k} \frac{1}{n_i \times f_i}$$

where,
i denotes an order from the object side of lenses in the image forming optical system,
k denotes total number of lenses in the image forming optical system,
$n_i$ denotes a refractive index for a d-line of an $i^{th}$ lens, and
$f_i$ denotes a focal length of the $i^{th}$ lens.

50. The image forming optical system according to claim 43, further comprising:
an aperture stop which limits an axial light beam, wherein the following conditional expression (B10) is satisfied:

$$(EXP/f)/(\phi_e'/\phi_1') < -1.2 \qquad (B10),$$

where,
EXP denotes a distance along the optical axis from the image up to a paraxial exit pupil position of the image forming optical system, and is let to be negative when the paraxial exit pupil position is on the object side of the image,
f denotes the focal length of the image forming optical system,
$\phi_e'$ denotes a maximum diameter of an area on the object-side optical surface through which an effective light beam that contributes to image formation at the maximum image height position passes, when measured perpendicularly with respect to an optical axis, and
$\phi_1'$ denotes a maximum diameter of an area on the object-side optical surface through which an axial light beam of the image forming optical system passes, when measured perpendicularly with respect to the optical axis.

51. The image forming optical system according to claim 43, wherein, when the lens component is let to be a lens having an object-side surface and an image-side surface that are in contact with air in the effective optical path through which a light beam contributing to the image formation passes, the image forming optical system includes, in order from the object side to the image side, an object-side lens component and an image-side lens component.

52. An image pickup apparatus comprising:
the image forming optical system according to claim 43; and
an image pickup unit having an image pickup surface which is curved to be concave toward the object side.

53. An image forming optical system which forms an image curved to be concave toward an object side, wherein the following conditional expressions (7), (8) and (B3-3) are satisfied:

$$Fno < 4 \qquad (7),$$

$$0.7 < IH/f < 1.2 \qquad (8), \text{ and}$$

$$EXP_{60}/f < -1 \qquad (B3-3),$$

where,
Fno denotes F number of the image forming optical system,
IH denotes a maximum image height
f denotes a focal length of the image forming optical system, and
$EXP_{60}$ denotes an exit-pupil position by a light ray incident on the image forming optical system at a half angle of view of 60 degrees.

54. The image pickup apparatus according to claim 14, wherein a total number of lens elements of the object-side lens component is at most two.

55. The image forming optical system according to claim 21, wherein a total number of lens elements of the object-side lens component is at most two.

56. The image forming optical system according to claim 27, wherein a total number of lens elements of the object-side lens component is at most two.

57. The image forming optical system according to claim 34, wherein a total number of lens elements of the object-side lens component is at most two.

58. The image forming optical system according to claim 43, wherein a total number of lens elements of the object-side lens component is at most two.

59. The image pickup apparatus according to claim 1, further comprising an aperture stop which limits an axial light beam,
wherein the aperture stop is located between the object-side lens component and the image-side lens component.

60. The image pickup apparatus according to claim 14, further comprising an aperture stop which limits an axial light beam,
wherein the aperture stop is located between the object-side lens component and the image-side lens component.

61. The image forming optical system according to claim 20, further comprising an aperture stop which limits an axial light beam,
wherein the aperture stop is located between the object-side lens component and the image-side lens component.

62. The image forming optical system according to claim 21, further comprising an aperture stop which limits an axial light beam,
wherein the aperture stop is located between the object-side lens component and the image-side lens component.

63. The image forming optical system according to claim 27, wherein the aperture stop is located between the object-side lens component and the image-side lens component.

64. The image forming optical system according to claim 34, wherein the aperture stop is located between the object-side lens component and the image-side lens component.

65. The image forming optical system according to claim 43, further comprising an aperture stop which limits an axial light beam,
wherein the aperture stop is located between the object-side optical surface and the image-side optical surface.

* * * * *